(12) United States Patent
Bunnelle et al.

(10) Patent No.: US 8,148,408 B2
(45) Date of Patent: Apr. 3, 2012

(54) SELECTIVE SUBSTITUTED PYRIDINE LIGANDS FOR NEURONAL NICOTINIC RECEPTORS

(75) Inventors: William H. Bunnelle, Mundelein, IL (US); Lei Shi, Gurnee, IL (US); Marc J. C. Scanio, Lindenhurst, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 12/430,468

(22) Filed: Apr. 27, 2009

(65) Prior Publication Data

US 2009/0281118 A1 Nov. 12, 2009

Related U.S. Application Data

(60) Provisional application No. 61/051,778, filed on May 9, 2008.

(51) Int. Cl.
*A61K 31/44* (2006.01)
(52) U.S. Cl. ........ 514/338; 546/148; 546/187; 548/152; 548/453; 549/59
(58) Field of Classification Search .................. 514/338; 546/148, 187; 548/152, 453; 549/59
See application file for complete search history.

(56) References Cited

U.S. PATENT DOCUMENTS 6,809,105 B2 * 10/2004 Schrimpf et al. .............. 514/300
6,852,721 B2    2/2005 Miller et al.

FOREIGN PATENT DOCUMENTS

| WO | 00/44755 | 8/2000 |
|---|---|---|
| WO | 01/44243 | 6/2001 |
| WO | 01/81347 | 11/2001 |
| WO | 2005/028477 | 3/2005 |
| WO | 2007/090888 | 6/2007 |

OTHER PUBLICATIONS

Balbani, A. et al., Recent developments for smoking cessation and treatment of nicotine dependence, Expert Opin. Ther. Patents (2007), pp. 287-297, vol. 17(3).
Bunnelle, W. et al., Neuronal nicotinic acetylcholine receptor ligands as potential analgasics, Expert Opin. Ther. Patents (2003), pp. 1003-1021, vol. 13(7).
Decker, M.W. et al., The therapeutic potential of nicotinic acetylcholine receptor agonists for pain control, Expert Opin. Investig. Drugs (2001), pp. 1819-1830, vol. 10(10).
Foot, O.F. et al., Synthesis of O-alkylhydroxylamines by electrophilic amination of alkoxides, Chem. Commun. (2000), pp. 975-976.
Gotti, C. et al., Neuronal nicotinic receptors: from structure to pathology, Progress in Neurobiology (2004), pp. 363-396, vol. 74.
Greene, T.W., Protective Groups in Organic Synthesis, 3rd Edition, John Wiley & Sons, New York (1999) Table of Contents.
Gurwitz, David, The therapeutic potential of nicotine and nicotinic agonists for weight control, Expert Opin. Invest. Drugs (1999), pp. 747-760, vol. 8(6).
Hogg, R.C. et al., Nicotinic acetylcholine receptors: from structure to brain function, Rev. Physiol. Biochem. Pharmacol. (2003), pp. 1-46, vol. 147.
Imai, K. et al., Anticoccidials, VI. An Improved Synthesis of 1,6-Dihydro-6-oxo-2-pyrazinecarboxylic Acid 4-Oxide and Some Related Derivatives and Determination of Anticoccidial Activity, Chem. Pharm. Bull. (1981), pp. 88-97, vol. 29(1).
Ji, J. et al., Synthesis and Structure—Activity Relationship Studies of 3,6-Diazabicyclo[3.2.0]heptanes as Novel a4B2 Nicotinic Acetylcholine Receptor Selective Agonists, J. Med. Chem. (2007), pp. 5493-5508, vol. 50.
Levin, Edward D., Nicotinic Receptor Subtypes and Cognitive Function, J. Neurobiol. (2002), pp. 633-640, vol. 53.
Pabreza, L.A., et al., [3H]Cytisine Binding to Nicotinic Cholinergic Receptors in Brain, Mol. Pharm. (1991), pp. 9-12, vol. 39.
Padwa, A. et al., N-Benzyl-N-Methoxymethyl-N-(Trimethylsilyl) Methylamine as an Azomethine Ylide Equivalent: 2,6-Dioxo-1-Phenyl-4-Benzyl-1,4-Diazabicyclo[3.3.0] Octane, Organic Syntheses (1989) pp. 133-140, vol. 67.
Paterson, D. et al., Neuronal nicotinic receptors in the human brain, Progress in Neurobiology (2000), pp. 75-111, vol. 61.
Vincler, M. et al., Targeting the a9a10 nicotinic acetylcholine receptor to treat severe pain, Expert Opin. Ther. Targets (2007), pp. 891-897, vol. 11(7).
Vincler, M. et al., Neuronal nicotinic receptors as targets for novel analgesics, Expert Opin. Investig. Drugs (2005), pp. 1191-1198, vol. 14(10).
International Search Report dated Aug. 17, 2009.
March, Jerry, Advanced Organic Chemistry, 4th Edition, John Wiley & Sons, Inc. (1992), p. 145, Table 4.3.

* cited by examiner

*Primary Examiner* — James O Wilson
*Assistant Examiner* — Douglas M Willis
(74) *Attorney, Agent, or Firm* — Lisa V. Mueller; Michael Best & Friedrich LLP

(57) ABSTRACT

The present application describes selective ligands of formula (I)

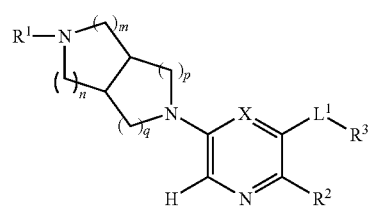

for neuronal nicotinic receptors (NNRs), more specifically for the α4β2 NNR subtype, compositions thereof, and methods of using the same, wherein X, $R^1$, X, $R^2$, $R^3$, $L^1$, m, n, p, and q are defined in the specification.

16 Claims, No Drawings

SELECTIVE SUBSTITUTED PYRIDINE LIGANDS FOR NEURONAL NICOTINIC RECEPTORS

This application claims priority to U.S. patent application Ser. No. 61/051,778, filed May 9, 2008 and is incorporated herein by reference.

BACKGROUND AND TECHNICAL FIELD

The present application describes selective ligands for neuronal nicotinic receptors (NNRs), more specifically for the α4β2 NNR subtype, compositions thereof, and methods of using the same.

Nicotinic acetylcholine receptors (nAChRs), belonging to the super family of ligand gated ion channels (LGIC), are widely distributed throughout the central nervous system (CNS) and the peripheral nervous system (PNS), and gate the flow of cations, controlled by acetylcholine (ACh). The nAChRs can be divided into nicotinic receptors of the muscular junction (NMJ) and neuronal nAChRs or neuronal nicotinic receptors (NNRs). The NNRs are understood to play an important role in regulating CNS function and the release of many neurotransmitters, including, but not necessarily limited to acetylcholine, norepinephrine, dopamine, serotonin and GABA. Consequently, nicotinic receptors mediate a very wide range of physiological effects, and have been targeted for therapeutic treatment of disorders relating to cognitive function, learning and memory, neurodegeneration, pain and inflammation, psychosis and sensory gating, mood and emotion, among others.

Typically, NNRs are ion channels that are constructed from a pentameric assembly of subunit proteins. Sixteen subunits of nAChRs have been reported to date, which are identified as α2-α10, β1-β4, γ, δ, and ε. Of these subunits, nine subunits, α2 through α7 and β2 through β4 prominently exist in the mammalian brain. Multiple functionally distinct NNRs complexes also exist, for example five α7 subunits can form a receptor as a homomeric functional pentamer or combinations of different subunits can complex together as in the case of α4β2 and α3β4 receptors (see for example, Vincler, M., Mcintosh, J. M., Targeting the α9α10 nicotinic acetylcholine receptor to treat severe pain, *Exp. Opin. Ther. Targets*, 2007, 11 (7): 891-897; Paterson, D. and Nordberg, A., Neuronal nicotinic receptors in the human brain, *Prog. Neurobiol.* 2000, 61: 75-111; Hogg, R. C., Raggenbass, M., Bertrand, D., Nicotinic acetylcholine receptors: from structure to brain function, *Rev. Physiol., Biochem. Pharmacol.*, 2003, 147: 1-46; Gotti, C., Clementi, F., Neuronal nicotinic receptors: from structure to pathology, *Prog. Neurobiol.*, 2004, 74: 363-396). These subunits provide for a great variety of homomeric and heteromeric combinations that account for the diverse receptor subtypes.

The NNRs, in general, are involved in various cognitive functions, such as learning, memory, attention, and therefore in CNS disorders, i.e., Alzheimer's disease (AD), Parkinson's disease (PD), attention deficit hyperactivity disorder (ADHD), Tourette's syndrome, schizophrenia, bipolar disorder, pain, and tobacco dependence. NNR ligands have been implicated in smoking cessation, weight control and as potential analgesics (see for example, Balbani, A. P. S., Montovani, J. C., Recent developments for smoking cessation and treatment of nicotine dependence, *Exp. Opin. Ther. Patents*, 2003, 13 (7): 287-297; Gurwitz, D., The therapeutic potential of nicotine and nicotinic agonists for weight control, *Exp. Opin. Invest. Drugs*, 1999, 8(6): 747-760; Vincler, M., Neuronal nicotinic receptors as targets for novel analgesics, *Exp. Opin. Invest. Drugs*, 2005, 14 (10): 1191-1198; Bunnelle, W. H., Decker, M. W., Neuronal nicotinic acetylcholine receptor ligands as potential analgesics, *Exp. Opin. Ther. Patents*, 2003, 13 (7): 1003-1021; Decker, M. W., Meyer, M. D., Sullivan, J. P., The therapeutic potential of nicotinic acetylcholine receptor agonists for pain control, *Exp. Opin. Invest Drugs*, 2001, 10 (10): 1819-1830; Vincler, M., McIntosh, J. M., Targeting the α9α10 nicotinic acetylcholine receptor to treat severe pain, *Exp. Opin. Ther. Targets*, 2007, 11 (7): 891-897).

The α4β2 receptor is one of the most abundant NNRs in the human brain, along with the homomeric α7 receptor. α4β2 NNRs have been shown to play a significant role in enhancing cognitive function, including aspects of learning, memory and attention (Levin, E. D., J. Neurobiol. 53: 633-640, 2002). Similarly, the α4β2 receptor subtype is implicated in epilepsy and pain control (Paterson, D. and Nordberg, A., Neuronal nicotinic receptors in the human brain, *Prog. Neurobiol.* 2000, 61: 75-111).

Certain compounds, like the plant alkaloid nicotine, interact with all known subtypes of the nAChRs, accounting for the profound physiological effects of this compound. Nicotine is known to provide enhanced attention and cognitive performance, reduced anxiety, enhanced sensory gating, and analgesia and neuroprotective effects when administered. Such effects are mediated by the non-selective effect of nicotine at a variety of nicotinic receptor subtypes. However, nicotine also produces adverse consequences, such as cardiovascular and gastrointestinal problems that interfere at therapeutic doses, and its addictive nature and acute toxicity are well-known. Accordingly, there is a need to identify subtype-selective compounds that evoke the beneficial effects of nicotine while eliminating or decreasing adverse effects.

The activity at the NNRs can be modified or regulated by the administration of subtype selective NNR ligands. The ligands can exhibit antagonist, agonist, or partial agonist properties and thus have potential in treatment of various cognitive disorders.

Although compounds that non-selectively demonstrate activity at a range of nicotinic receptor subtypes including the α4β2 and α7 NNRs are known, it would be beneficial to provide compounds that interact selectively with α4β2 NNRs.

SUMMARY

The principal embodiment of the present application provides compounds of formula (I)

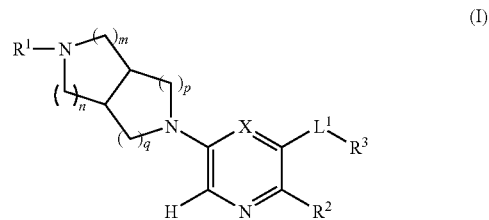

or a pharmaceutically acceptable salt, prodrug, salt of a prodrug, or a combination thereof, wherein X is N or CH;

$R^1$ is hydrogen, alkyl, alkenyl, or heteroarylalkyl; wherein the heteroaryl moiety of the heteroarylalkyl is optionally substituted with 1, 2, 3, 4, or 5 substituents as represented by $R^x$;

m and q are each independently 1 or 2;

n and p are each independently 0, 1, or 2;

$R^2$ is hydrogen, halogen, $C_{1-3}$ haloalkyl, $C_{1-3}$ alkyl, CN, $NO_2$, C(O)H, $C_{1-3}$ alkoxy, $C_{1-3}$ haloalkoxy, or $NH_2$;

$L^1$ is a bond, —C(=Y)N($R^a$)—, —N($R^a$)C(=Y)—, O, N($R^b$), S, S(O), S(O)$_2$, C(=Y), —C($R^c$)=N—O—, —C($R^c$)=N—N($R^{c'}$), or —C($R^c$)=N—N($R^{c''}$)C(O)—; wherein each occurrence of Y is independently O or S;

$R^3$ is —$C_{2-4}$ alkenylenyl-$G^1$, $G^2$, or —(C$R^dR^e$)$_t$-$G^3$; provided that when $R^3$ is $G^2$, then $L^1$ is other than a bond;

t is 1, 2, 3, or 4;

$R^d$ and $R^e$, at each occurrence, are independently hydrogen, alkyl, haloalkyl, halogen, O$R^f$, N($R^f$)($R^g$), —($C_{1-6}$ alkylenyl)-O$R^f$, or —($C_{1-6}$ alkylenyl)-N($R^f$)($R^g$);

$R^a$, $R^b$, $R^c$, $R^{c'}$, $R^{c''}$, $R^f$, and $R^g$, at each occurrence, are each independently hydrogen, alkyl, or haloalkyl;

$G^1$, $G^2$, and $G^3$, are each independently aryl, heteroaryl, heterocycle, cycloalkyl, or cycloalkenyl, wherein each ring as represented by $G^1$, $G^2$, and $G^3$, are each independently unsubstituted or substituted with 1, 2, 3, 4, or 5 substituents independently selected from the group consisting of alkyl, alkenyl, alkynyl, halogen, oxo, CN, $NO_2$, O($R^4$), S($R^4$), S(O)$R^5$, S(O)$_2R^5$, S(O)$_2$N($R^6$)($R^7$), OC(O)($R^4$), C(O)$R^4$, C(O)O($R^4$), C(O)N($R^6$)($R^7$), N($R^6$)($R^7$), N($R^6$)S(O)$_2$($R^5$), N($R^6$)C(O)O($R^4$), N($R^6$)C(O)N($R^6$)($R^7$), N($R^6$)S(O)$_2$N($R^6$)($R^7$), haloalkyl, —($C_{1-6}$ alkylenyl)-CN, —($C_{1-6}$ alkylenyl)-NO$_2$, —($C_{1-6}$ alkylenyl)-O($R^4$), —($C_{1-6}$ alkylenyl)-S($R^4$), —$C_{1-6}$ alkylenyl)-S(O)$R^5$, —($C_{1-6}$ alkylenyl)-S(O)$_2R^5$, —($C_{1-6}$ alkylenyl)-S(O)$_2$N($R^6$)($R^7$), —($C_{1-6}$ alkylenyl)-OC(O)($R^4$), —($C_{1-6}$ alkylenyl)-C(O)$R^4$, —($C_{1-6}$ alkylenyl)-C(O)O($R^4$), —($C_{1-6}$ alkylenyl)-C(O)N($R^6$)($R^7$), —($C_{1-6}$ alkylenyl)-N($R^6$)($R^7$), —($C_{1-6}$ alkylenyl)-N($R^6$)S(O)$_2$($R^5$), —($C_{1-6}$ alkylenyl)-N($R^6$)C(O)O($R^4$), —($C_{1-6}$ alkylenyl)-N($R^6$)C(O)N($R^6$)($R^7$), —($C_{1-6}$ alkylenyl)-N($R^6$)S(O)$_2$N($R^6$)($R^7$), $G^4$, or —($C_{1-6}$ alkylenyl)-$G^4$;

$R^4$ and $R^7$, at each occurrence, are each independently hydrogen, alkyl, haloalkyl, $G^5$, or —($C_{1-6}$ alkylenyl)-$G^5$;

$R^5$, at each occurrence, is independently alkyl, haloalkyl, $G^5$, or —($C_{1-6}$ alkylenyl)-$G^5$;

$R^6$, at each occurrence, is independently hydrogen, alkyl, or haloalkyl;

$G^4$ and $G^5$, are each independently aryl, heteroaryl, heterocycle, cycloalkyl or cycloalkenyl; each of which is independently unsubstituted or substituted by 1, 2, 3, 4, or 5 substituents as represented by $R^8$; and each occurrence of $R^8$ and $R^x$ are independently alkyl, alkenyl, alkynyl, halogen, oxo, CN, NO$_2$, O($R^9$), S($R^9$), S(O)$R^{10}$, S(O)$_2R^{10}$, S(O)$_2$N($R^{11}$)($R^{12}$), OC(O)($R^9$), C(O)$R^9$, C(O)O($R^9$), C(O)N($R^{11}$)($R^{12}$), N($R^{11}$)($R^{12}$), N($R^{11}$)S(O)$_2$($R^{10}$), N($R^{11}$)C(O)O($R^9$), N($R^{11}$)C(O)N($R^{11}$)($R^{12}$), N($R^{11}$)S(O)$_2$N($R^{11}$)($R^{12}$), haloalkyl, —($C_{1-6}$ alkylenyl)-CN, —($C_{1-6}$ alkylenyl)-NO$_2$, —($C_{1-6}$ alkylenyl)-O($R^9$), —($C_{1-6}$ alkylenyl)-S($R^9$), —($C_{1-6}$ alkylenyl)-S(O)$R^{10}$, —($C_{1-6}$ alkylenyl)-S(O)$_2R^{10}$, —($C_{1-6}$ alkylenyl)-S(O)$_2$N($R^{11}$)($R^{12}$), —($C_{1-6}$ alkylenyl)-OC(O)($R^9$), —($C_{1-6}$ alkylenyl)-C(O)$R^9$, —($C_{1-6}$ alkylenyl)-C(O)O($R^9$), —($C_{1-6}$ alkylenyl)-C(O)N($R^{11}$)($R^{12}$), —($C_{1-6}$ alkylenyl)-N($R^{11}$)($R^{12}$), —($C_{1-6}$ alkylenyl)-N($R^{11}$)S(O)$_2$($R^{10}$), —($C_{1-6}$ alkylenyl)-N($R^{11}$)C(O)O($R^9$), —($C_{1-6}$ alkylenyl)-N($R^{11}$)C(O)N($R^{11}$)($R^{12}$), or —($C_{1-6}$ alkylenyl)-N($R^{11}$)S(O)$_2$N($R^{11}$)($R^{12}$); wherein $R^9$, $R^{11}$, and $R^{12}$, at each occurrence, are each independently hydrogen, alkyl, or haloalkyl; and $R^{10}$, at each occurrence, is independently alkyl or haloalkyl.

Also comprised in the present application are pharmaceutical compositions comprising one or more therapeutically effective amounts of compounds described herein or pharmaceutically acceptable salts thereof in combination with one or more pharmaceutically acceptable carriers.

The present application also relates to methods of treating mild cognitive impairment, age-associated memory impairment (AAMI), senile dementia, AIDS dementia, Pick's Disease, dementia associated with Lewy bodies, dementia associated with Down's syndrome, amyotrophic lateral sclerosis, Huntington's disease, smoking cessation, schizoaffective disorder, bipolar and manic disorders, diminished CNS function associated with traumatic brain injury, acute pain, post-surgical pain, chronic pain, inflammatory pain, attention deficit disorder, attention deficit hyperactivity disorder (ADHD), Alzheimer's disease (AD), schizophrenia, or cognitive deficits associated with schizophrenia (CDS), in mammals in need of such treatment comprising administering to the mammals therapeutically effective amounts of one or more compounds described herein or pharmaceutically acceptable salts thereof, alone or in combination with one or more pharmaceutically acceptable carriers.

Further included are methods of treating a mammal having conditions or disorders where modulation of α4β2 NNR activity is of therapeutic benefit. Said methods comprising administering to subjects having or susceptible to said disorders with therapeutically effective amounts of one or more compounds described herein, or pharmaceutically acceptable salts thereof, alone or in combination with one or more pharmaceutically acceptable carriers.

A further aspect relates to the use of compounds described herein or pharmaceutically acceptable salt(s) thereof, in the manufacture of medicaments for the treatment of the disorders or conditions described above, alone or in combination with one or more pharmaceutically acceptable carrier(s).

The compounds, compositions comprising the compounds, and methods for treating or preventing conditions and disorders by administering the compounds are further described herein.

These and other objectives are described in the following paragraphs. These objectives should not be deemed to narrow the scope of the invention.

DETAILED DESCRIPTION

In various embodiments, compounds described herein may contain variables that occur more than one time in any substituent or in the compound described or any other formulae herein. Definition of a variable on each occurrence is independent of its definition at another occurrence. Further, combinations of variables or substituents are permissible only if such combinations result in stable compounds. Stable compounds are compounds, which can be isolated from a reaction mixture.

As used in the specification and the appended claims, unless specified to the contrary, following terms have the meaning indicated:

The term "alkenyl" as used herein, means a straight or branched hydrocarbon chain containing from 2 to 10 carbons and containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "$C_{2-4}$ alkenylenyl" denotes a divalent group derived from a straight or branched hydrocarbon chain of 2, 3, or 4 carbon atoms and contains one or two carbon-carbon double. Representative examples of alkenylenyl include, but are not limited to, —CH=CH— and —CH$_2$CH=CH—.

The term "alkoxy" as used herein, means an alkyl group, as defined herein, appended to the parent molecular moiety through an oxygen atom. The term "$C_{1-3}$ alkoxy" as used herein, means a $C_{1-3}$ alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkyl" as used herein, means a saturated, straight or branched hydrocarbon chain containing from 1 to 10 carbon atoms. The term "$C_{1-3}$ alkyl" as used herein, means a saturated, straight or branched hydrocarbon chain containing from 1 to 3 carbon atoms. The term "$C_{1-6}$ alkyl" as used herein, means a saturated, straight or branched hydrocarbon chain containing from 1 to 6 carbon atoms. Representative examples of alkyl include, but are not limited to, methyl, ethyl, n-propyl, isopropyl, n-butyl, sec-butyl, isobutyl, tert-butyl, n-pentyl, isopentyl, neopentyl, n-hexyl, 1-methylbutyl, 2-methylbutyl, 3-methylbutyl, 1,1-dimethylpropyl, 1,2-dimethylpropyl, 2,2-dimethylpropyl, 1-methylpropyl, 1-ethylpropyl, 1,2,2-trimethylpropyl, 3-methylhexyl, 2,2-dimethylpentyl, 2,3-dimethylpentyl, n-heptyl, n-octyl, n-nonyl, and n-decyl.

The term "$C_{1-6}$ alkylenyl" means a divalent group derived from a saturated, straight or branched hydrocarbon chain of from 1 to 6 carbon atoms. Representative examples of $C_{1-4}$ alkylenyl include, but are not limited to, —CH$_2$—, —CH(CH$_3$)—, —CH(C$_2$H$_5$), —CH(CH(CH$_3$)(C$_2$H$_5$))—, —C(H)(CH$_3$)CH$_2$CH$_2$—, —C(CH$_3$)$_2$—, —CH$_2$CH$_2$—, —CH$_2$CH$_2$CH$_2$—, —CH$_2$CH$_2$CH$_2$CH$_2$—, and —CH$_2$CH(CH$_3$)CH$_2$—.

The term "alkynyl" as used herein, means a straight or branched hydrocarbon chain containing from 2 to 10 carbon atoms and containing at least one carbon-carbon triple bond. Representative examples of alkynyl include, but are not limited, to acetylenyl, 1-propynyl, 2-propynyl, 1,1-dimethylprop-2-ynyl, 1-propyl-pent-3-ynyl, 3-butynyl, 2-pentynyl, and 1-butynyl.

The term "aryl" as used herein, means phenyl or a bicyclic aryl. The bicyclic aryl is naphthyl, or a phenyl fused to a monocyclic cycloalkyl, or a phenyl fused to a monocyclic cycloalkenyl. Representative examples of the aryl groups include, but are not limited to, dihydroindenyl (including 2,3-dihydro-1H-inden-1-yl), indenyl, naphthyl, dihydronaphthalenyl, and tetrahydronaphthalenyl. The bicyclic aryl is attached to the parent molecular moiety through any carbon atom contained within the bicyclic ring system. The aryl groups of the present invention can be unsubstituted or substituted.

The term "cycloalkyl" or "cycloalkane" as used herein, means a monocyclic, a bicyclic, or a tricyclic cycloalkyl. The monocyclic cycloalkyl is a carbocyclic ring system containing three to eight carbon atoms, zero heteroatoms and zero double bonds. Examples of monocyclic ring systems include cyclopropyl, cyclobutyl, cyclopentyl, cyclohexyl, cycloheptyl, and cyclooctyl. The bicyclic cycloalkyl is a monocyclic cycloalkyl fused to a monocyclic cycloalkyl ring. The monocyclic or bicyclic cycloalkyl ring may contain one or two alkylene bridges, each independently consisting of one, two, three, or four carbon atoms, each independently linking two non-adjacent carbon atoms of the ring system. Representative examples of such bridged ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, bicyclo[4.2.1]nonane, tricyclo[3.3.1.0$^{3,7}$]nonane (octahydro-2,5-methanopentalene or noradamantane), and tricyclo[3.3.1.1$^{3,7}$]decane (adamantane). The monocyclic and the bicyclic cycloalkyls can be unsubstituted or substituted, and are attached to the parent molecular moiety through any substitutable atom contained within the ring system.

The term "cycloalkenyl" or "cycloalkene" as used herein, means a monocyclic or a bicyclic hydrocarbon ring system. The monocyclic cycloalkenyl has four-, five-, six-, seven- or eight carbon atoms and zero heteroatoms. The four-membered ring systems have one double bond, the five- or six-membered ring systems have one or two double bonds, and the seven- or eight-membered ring systems have one, two or three double bonds. Representative examples of monocyclic cycloalkenyl groups include, but are not limited to, cyclobutenyl, cyclopentenyl, cyclohexenyl, cycloheptenyl and cyclooctenyl. The bicyclic cycloalkenyl is a monocyclic cycloalkenyl fused to a monocyclic cycloalkyl group, or a monocyclic cycloalkenyl fused to a monocyclic cycloalkenyl group. The monocyclic or bicyclic cycloalkenyl ring may contain one or two alkylene bridges, each consisting of one, two or three carbon atoms, each linking two non-adjacent carbon atoms of the ring system. Representative examples of the bicyclic cycloalkenyl groups include, but are not limited to, 4,5,6,7-tetrahydro-3aH-indene, octahydronaphthalenyl and 1,6-dihydro-pentalene. The monocyclic and bicyclic cycloalkenyl can be attached to the parent molecular moiety through any substitutable atom contained within the ring systems, and can be unsubstituted or substituted.

The term "halo" or "halogen," as used herein, means —Cl, —Br, —I or —F.

The term "haloalkoxy," as used herein, means an alkoxy group, as defined herein, in which one, two, three, four, five, or six hydrogen atoms are replaced by halogen. The term "$C_{1-3}$ haloalkoxy," as used herein, means a $C_{1-3}$ alkoxy group, as defined herein, in which one, two, three, four, five, or six hydrogen atoms are replaced by halogen. Representative examples of haloalkoxy include, but are not limited to, trifluoromethoxy, difluoromethoxy, 2,2,2-trifluoroethoxy, 2,2-difluoroethoxy, 2-fluoroethoxy, and pentafluoroethoxy.

The term "haloalkyl," as used herein, means an alkyl group, as defined herein, in which one, two, three, four, five, six, or seven hydrogen atoms are replaced by halogen. The term "$C_{1-3}$ haloalkyl," as used herein, means a $C_{1-3}$ alkyl group, as defined herein, in which one, two, three, four, five, six, or seven hydrogen atoms are replaced by halogen. Representative examples of haloalkyl include, but are not limited to, chloromethyl, 2-fluoroethyl, 2,2-difluoroethyl, trifluoromethyl, 2,2,2-trifluoroethyl, 2,2,2-trifluoro-1,1-dimethylethyl, difluoromethyl, 3,3,3-trifluoropropyl, pentafluoroethyl, 2-chloro-3-fluoropentyl, and 2-iodoethyl.

The term "heterocycle" or "heterocyclic" as used herein, means a monocyclic heterocycle or a bicyclic heterocycle. The monocyclic heterocycle is a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two or three heteroatoms selected from the group consisting of O, N and S. The six-membered ring contains zero, one or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydropyranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle. Representative examples of bicyclic heterocycles include, but are not limited to, benzopyranyl, benzothiopyranyl, 2,3-dihydrobenzofuranyl, 2,3-dihydrobenzothienyl, 2-azabicyclo[2.2.1]hept-2-yl, 1,2,3,4-tetrahydroisoquinolinyl, dihydroisoquinolinyl (including 3,4-dihydroisoquinolin-2(1H)-yl), and 2,3-dihydro-1H-indolyl. The monocyclic and the bicyclic heterocycle groups of the present invention may contain one or two alkenylene bridge of 2, 3, or 4 carbon atoms, or one or two alkylene bridges of 1, 2, 3, or 4 carbon atoms, wherein each bridge links two non-adjacent carbon atoms within the groups. Examples of such bridged heterocycles include, but are not limited to, 2-oxa-5-azabicyclo[2.2.1]heptane, 2-azabicyclo[2.2.1]heptane, oxaadamantane (2-oxatricyclo[3.3.1.1$^{3,7}$]decane), octahydro-2,5-epoxypentalene, hexahydro-2H-2,5-methanocyclopenta[b]furan, hexahydro-1H-1,4-methanocyclopenta[c]furan, oxabicyclo[2.2.1]heptane and 2,4-dioxabicyclo[4.2.1]nonane. The monocyclic and the bicyclic heterocycle groups are connected to the parent molecular moiety through any substitutable carbon atom or any substitutable nitrogen atom contained within the groups. Any oxidized form of nitrogen or sulfur, and the quarternized form of any basic nitrogen in the monocyclic and the bicyclic heterocycle groups are also contemplated.

The term "heteroaryl" as used herein, means a monocyclic heteroaryl or a bicyclic heteroaryl. The monocyclic heteroaryl is a five- or six-membered ring. The five-membered ring contains two double bonds. The five membered ring may contain one heteroatom selected from O or S; or one, two, three, or four nitrogen atoms and optionally one oxygen or sulfur atom. The six-membered ring contains three double bonds and one, two, three or four nitrogen atoms. Representative examples of monocyclic heteroaryl include, but are not limited to, furanyl, imidazolyl, isoxazolyl, isothiazolyl, oxadiazolyl, 1,3-oxazolyl, pyridinyl (e.g. pyridin-2-yl, pyridin-3-yl), pyridazinyl, pyrimidinyl, pyrazinyl, pyrazolyl, pyrrolyl, tetrazolyl, thiadiazolyl, 1,3-thiazolyl, thienyl (e.g. thien-2-yl), triazolyl, and triazinyl. The bicyclic heteroaryl consists of a monocyclic heteroaryl fused to a phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl, or a monocyclic heteroaryl fused to a monocyclic heterocycle. Representative examples of bicyclic heteroaryl groups include, but not limited to, benzofuranyl, benzothienyl, benzoxazolyl, benzimidazolyl, benzoxadiazolyl, benzothiazolyl (e.g. benzo[d]thiazol-6-yl), imidazo[1,2-a]pyridinyl, indazolyl, indolyl, isoindolyl, isoquinolinyl, naphthyridinyl, pyridoimidazolyl, quinolinyl, thiazolo[5,4-b]pyridin-2-yl, thiazolo[5,4-d]pyrimidin-2-yl, and 5,6,7,8-tetrahydroquinolin-5-yl. The monocyclic and bicyclic heteroaryl groups of the present invention can be substituted or unsubstituted and are connected to the parent molecular moiety through any carbon atom or any nitrogen atom contained within the ring systems.

The term "heteroarylalkyl" as used herein, means an heteroaryl group, as defined herein, appended to the parent molecular moiety through an alkylene group as defined herein. Examples include, but are not limited to, pyridin-2-ylmethyl, pyridin-3-ylmethyl.

Methods for Preparing Compounds

This invention is intended to encompass compounds of the invention when prepared by synthetic processes or by metabolic processes. Preparation of the compounds by metabolic processes includes those occurring in the human or animal body (in vivo) or processes occurring in vitro.

The compounds of the invention may be prepared by a variety of processes well known for the preparation of compounds of this class. For example, the compounds of the invention wherein the groups X, m, n, p, q, $R^1$, $R^2$, $R^3$, $L^1$, $R^a$, $R^b$, $R^c$, $R^{c'}$, $R^{c''}$, $G^1$, $G^2$, and $G^3$, have the meanings as set forth in the summary and the definition sections unless otherwise noted, can be synthesized as shown in Schemes 1-6.

As used in the descriptions of the schemes and the examples, certain abbreviations are intended to have the following meanings: Ac for acetyl; TEA for triethylamine; EtOH for ethanol; MeOH for methanol; TFA for trifluoroacetic acid;

EtOAc for ethyl acetate; Et$_2$O for diethyl ether; THF for tetrahydrofuran; DMAP for 4-(dimethylamino)pyridine; DMSO for dimethyl sulfoxide; DMF for N,N-dimethylformamide; HOBt for 1-hydroxybenzotriazole hydrate; EDCI for 1-ethyl-3-[3-(dimethylamino)propyl]-carbodiimide hydrochloride; mCPBA for m-chloroperbenzoic acid; DCM for dichloromethane; P(o-tolyl)$_3$ for tris(o-tolyl)phosphine), Pd$_2$(dba)$_3$ for tris(dibenzylideneacetone)dipalladium(0); and BINAP for 2,2'-bis(diphenylphosphino)-1,1'-binaphthyl.

Scheme 1

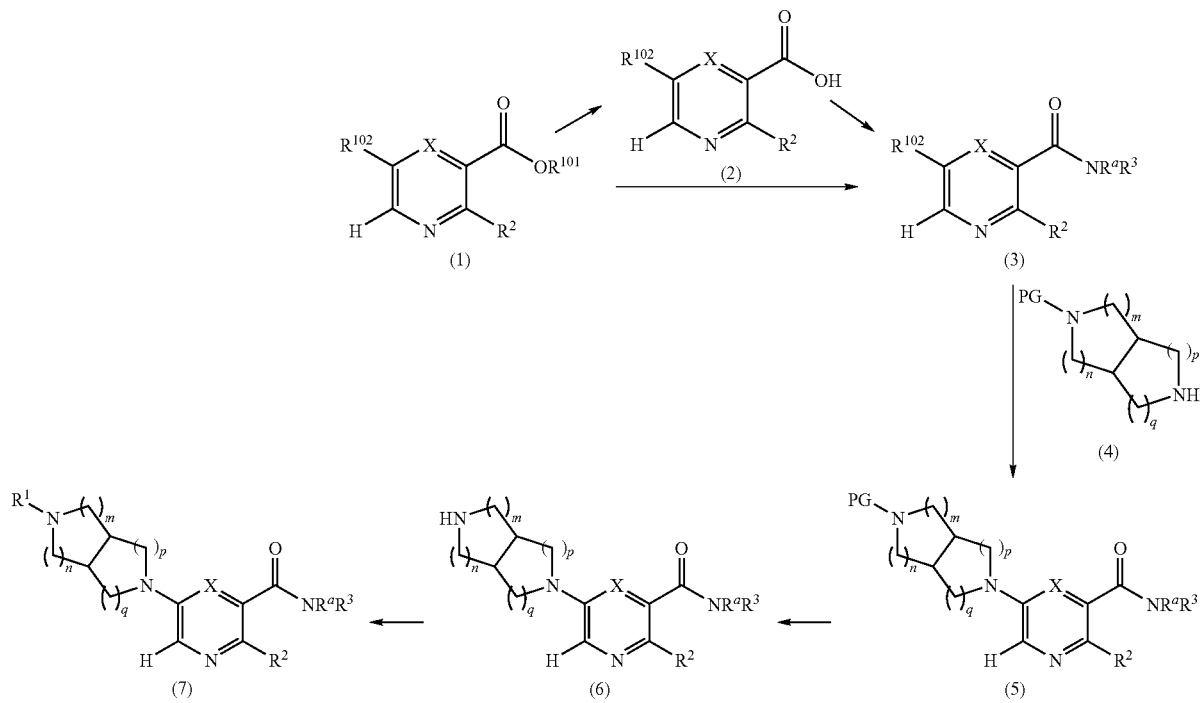

Compounds of general formula (I) wherein $L^1$ is —C(=O)N($R^a$)— may be prepared using general procedures as outlined in Scheme 1.

Compounds of formula (1) wherein $R^{101}$ is $C_{1-6}$ alkyl and $R^{102}$ is halogen, purchased or prepared using procedures known in the art (for example, Chem. Pharm. Bull. 1981, 29, 88-97) can be converted to the corresponding acids of formula (2), when subjected to basic hydrolysis using an inorganic base such as, but not limited to, NaOH, LiOH, or KOH. The reaction is generally performed at about room temperature and in a solvent such as, but not limited to, an alcohol (e.g. ethanol). Transformation of (2) to (3) can be achieved by treatment with amines of formula HN($R^a$)($R^3$) in the presence of a coupling agent, a base and optionally a coupling auxiliary. Examples of coupling reagents include, but are not limited to, 1-ethyl-3-[3-(dimethylamino)propyl]-carbodiimide hydrochloride (EDCI), bis(2-oxo-3-oxazolidinyl)phosphinic chloride (BOPCl), 1,3-dicyclohexylcarbodiimide (DCC), polymer supported 1,3-dicyclohexylcarbodiimide (PS-DCC), O-(7-azabenzotriazol-1-yl)-N,N,N',N'-tetramethyluronium hexafluorophosphate (HATU), and O-benzotriazol-1-yl-N,N,N',N'-tetramethyluronium tetrafluoroborate (TBTU). Examples of coupling auxiliaries include but are not limited to 1-hydroxy-7-azabenzotriazole (HOAT) and 1-hydroxybenzotriazole hydrate (HOBT). Examples of suitable bases include, but are not limited to, an organic base such as N-methyl morpholine, DMAP, triethylamine, or diisopropylethylamine, or an inorganic base such as sodium bicarbonate. The coupling reaction can be carried out in a solvent such as chloroform, dichloromethane, tetrahydrofuran, N,N-dimethylformamide, or mixtures thereof, at a temperature from about 0° C. to about 50° C.

Alternatively, acids of formula (2) can be converted to (3) by (a) treating with oxalyl chloride in the presence of catalytic amount of DMF, and (b) treating the acid chloride obtained from step (a) with amines of formula HN($R^a$)($R^3$) in the presence of an organic base such as, but not limited to, N-methyl morpholine, DMAP, triethylamine, or diisopropylethylamine. The acid chlorides may also be obtained by treating (2) with thionyl chloride.

Compounds of formula (1) wherein X is N can be directly converted to compounds of formula (3) wherein X is N by treatment with HN($R^a$)($R^3$) in the presence of magnesium chloride.

Treatment of compounds of formula (3) with protected bicyclic amines of formula (4) wherein PG is a nitrogen protecting group provide compounds of formula (5). Commonly used nitrogen-protecting groups are disclosed in T. W. Greene and P. G. M. Wuts, Protective Groups in Organic Synthesis, 3rd edition, John Wiley & Sons, New York (1999). Examples of PG include, but are not limited to, acetyl, benzoyl, benzyl, benzyloxycarbonyl (Cbz), formyl, phenylsulfonyl, tert-butoxycarbonyl (Boc), tert-butylacetyl, trifluoroacetyl, and triphenylmethyl (trityl).

The conversion may be accomplished by treatment of (4) and (3) wherein X is N, in the presence of a base at a temperature from about 20° C. to about 150° C., and in a solvent such as DMF or DMSO, to provide compounds of formula (5) wherein X is N. Examples of suitable bases for the transformation include, but are not limited to, sodium carbonate and diisopropylethylamine. Alternatively, the transformation of (3) to (5) wherein X is C or N can be achieved by treatment with (4) in the presence of a catalytic amount of a transition metal such as palladium or copper, a ligand, and a base, in a solvent (e.g. dioxane, toluene, etc.) and at a temperature ranging from about 20° C. to about 150° C. The transition metal used may be derived from a reagent such as, but not limited to, tris(dibenzylideneacetone)dipalladium(0). Non limiting examples of the suitable base include sodium tert-butoxide and cesium carbonate. Examples of suitable ligand include 2,2'-bis(diphenylphosphino)-1,1'-binaphthyl (BINAP) and Xantphos (9,9-Dimethyl-4,5-bis(diphenylphosphino)xanthene, Strem, CAS number 161265-03-8).

Removal of the nitrogen protecting group using reaction conditions as disclosed in T. W. Greene and P. G. M. Wuts, Protective Groups in Organic Synthesis, 3rd edition, John Wiley & Sons, New York (1999) provide amines of formula (6). For example, compounds of formula (5) wherein PG is Boc can be converted to (6) by treating with an acid such as, but not limited to, trifluoroacetic acid or hydrochloric acid.

Diamines of formula (4) can be prepared using reaction conditions analogous to those as described in the specific examples herein, or in U.S. Pat. No. 6,809,105.

Compounds of formula (7) wherein $R^1$ is other than hydrogen can be prepared from compounds of formula (1) using analogous synthesis known in the literature, for example, via reductive amination of (6) with appropriate aldehydes or ketones, or alkylation of (6). (6) may be treated with suitable aldehydes or ketones in the presence of a reducing agent such as, but not limited to, sodium triacetoxyborohydride in a solvent such as, but not limited to, methanol, to provide compounds of formula (7) wherein $R^1$ is other than hydrogen. Alternatively, (6) may be alkylated by treating with $R^1X^1$ wherein $R^1$ is other than hydrogen, and $X^1$ is halogen, in the presence of a base and in as solvent such as DMF.

Scheme 2

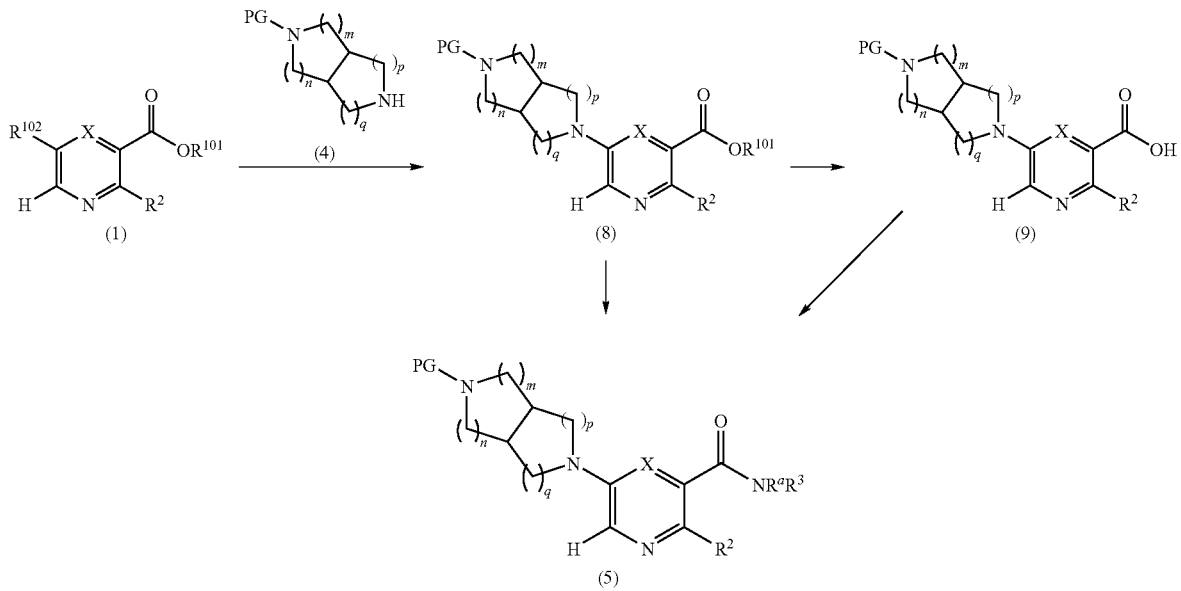

Alternatively, compounds of formula (5) may be prepared using general procedures as detailed in Scheme 2.

Treatment of protected diamines (4) with compounds of formula (1) wherein $R^{102}$ is halogen, utilizing reaction conditions as described in Scheme 1 for the transformation of (3) to (5), affords compounds of formula (8) wherein $R^{101}$ is $C_{1-6}$ alkyl. Compounds of formula (8), after base hydrolysis and treatment with amines of formula $HN(R^a)(R^3)$ using general reaction conditions as described in Scheme 1, provide compounds of formula (5). Alternatively, compounds of formula (5) wherein X is N may be prepared from compounds of formula (8) wherein X is N directly in the presence of magnesium chloride.

Scheme 3

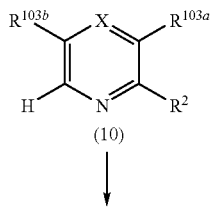

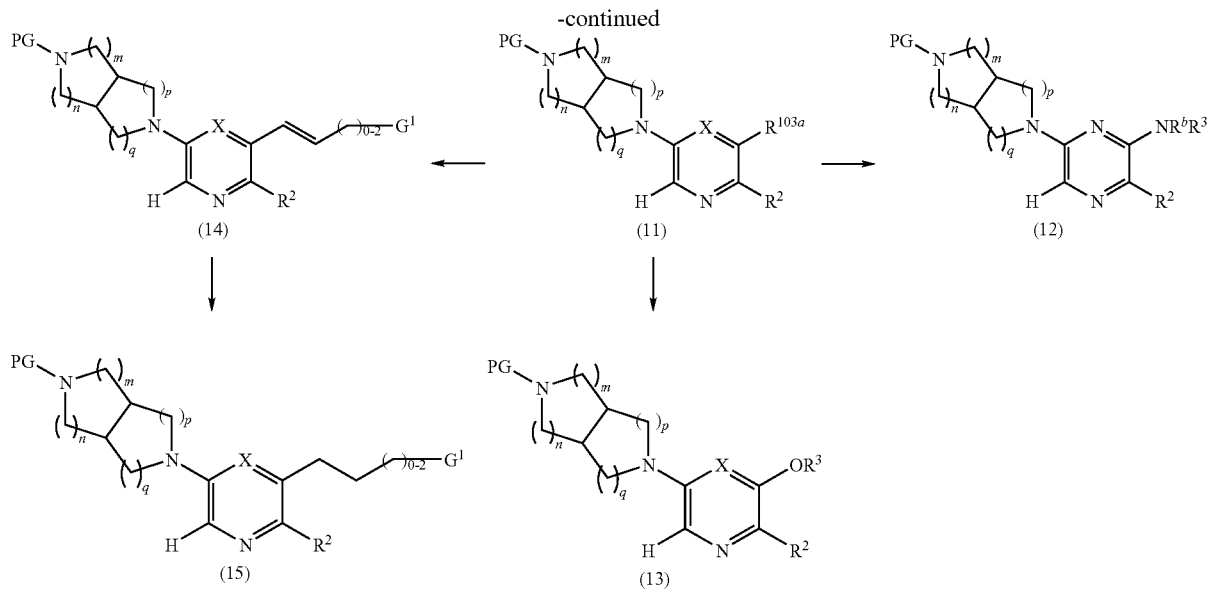

Compounds of general formula (I) wherein $L^1$ is O or $N(R^b)$, or $L^1$ is a bond and $R^3$ is —$C_{2-4}$ alkenylenyl-$G^1$ or —$(CH_2)_{2-4}$-$G^3$ may be prepared using general procedures as outlined in Scheme 3.

Compounds of formula (11) can be prepared from compounds of formula (10) wherein $R^{103a}$ and $R^{103b}$ are the same, and are each halogen, using reaction conditions for the conversion of (3) to (5) as described in Scheme 1.

Treatment of (11) wherein X is N with alcohols of formula $R^3$OH in the presence of a base (e.g. potassium tert-butoxide or sodium hydride) and a solvent (e.g. DMSO, DMF, and the like) provides ethers of formula (13) wherein X is N.

Treatment of (11) with amines of formula $HN(R^b)(R^3)$ using conditions for the transformation of (3) to (5) as depicted in Scheme 1 afford amines of formula (12).

Coupling of (11) with alkenes of formula $(H)_2C=C(H)-(CH_2)_{0-2}$-$G^1$ in the presence of a palladium catalyst (e.g. palladium(II) acetate), a ligand (e.g. triphenyl phosphine or tris(o-tolyl)phosphine), and a base (e.g. triethylamine or diisopropylethylamine, in a solvent such as, but not limited to, acetonitrile or acetone, and at elevated temperature, provides compounds of formula (14).

Catalytic hydrogenation of (14) using reaction conditions known to one skilled in the art lead to compounds of formula (15). For example, the reduction may be accomplished in the presence of a palladium catalyst (e.g. Pd/C) and hydrogen gas, in a solvent such as methanol or ethyl acetate, at ambient or elevated temperature.

Scheme 4

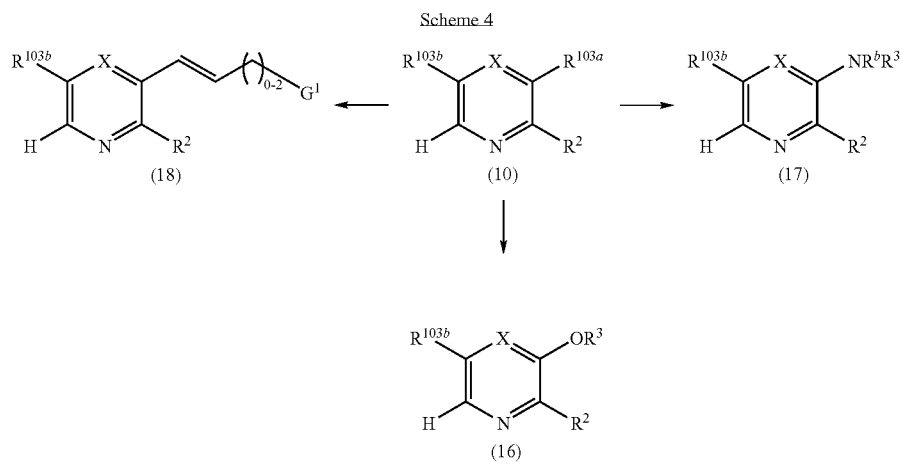

Alternatively, Compounds of general formula (I) wherein $L^1$ is O or $N(R^b)$, or $L^1$ is a bond and $R^3$ is —$C_{2-4}$ alkenylenyl-$G^1$ may be prepared using general procedures as outlined in Scheme 4, by first derivatizing (10) wherein $R^{103a}$ and $R^{103b}$ are as defined in Scheme 3, to the respective amines (17), ethers (16) and alkenes (18) as described in Scheme 3, followed by treatment with protected diamines (4) to compounds of formula (12), (13) and (14) respectively.

Scheme 5

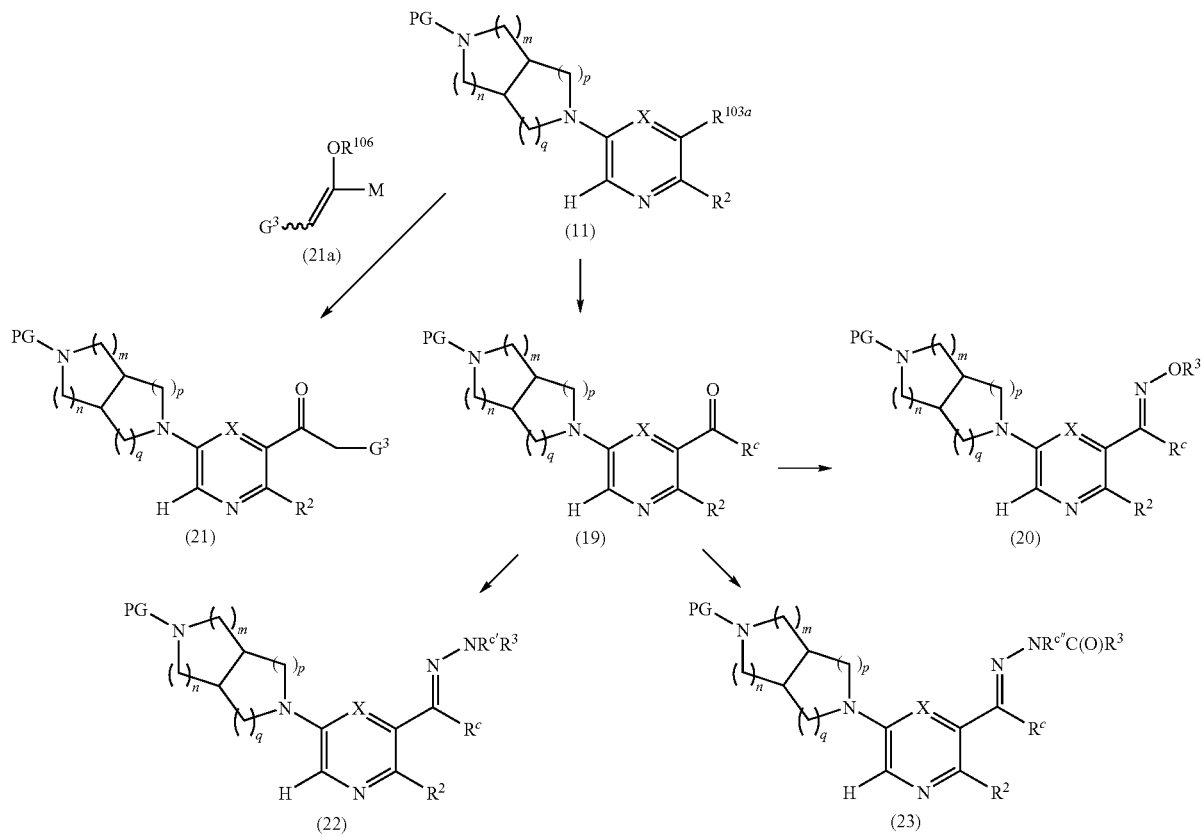

Scheme 5 illustrate general procedures that may be employed for the synthesis of compounds of general formula (I) wherein $L^1$ is —C($R^c$)=N—O—, —C($R^c$)=N—N($R^{c'}$)—, or —C($R^c$)=N—N($R^{c''}$)C(O)—.

For example, treatment of (11) with an organometallic reagent (e.g. tert-butyllithium) in a solvent such as THF containing approximately stoichiometric amounts of DMF at a temperature ranging from about −88° C. to about 20° C., provides aldehydes of formula (19) wherein $R^c$ is hydrogen. Metallation of (11) with an organometallic reagent (e.g. tert-butyllithium) followed by treatment with amides of formula $R^cC(O)N(R^{104a})(R^{104b})$ wherein $R^{104a}$ is methyl and $R^{104b}$ is methoxy, or $R^{104a}$ and $R^{104b}$ together with the nitrogen to which they are attached, is a morpholine, provides ketones of formula (19) wherein $R^c$ is alkyl. Ketones of formula (19) wherein $R^c$ is alkyl can also be obtained from aldehydes of formula (19) wherein $R^c$ is hydrogen by treatment of the aldehydes with a suitable organometallic agent (e.g an organolithium agent of formula $R^cLi$ or an organomagnesium reagent of formula $R^cMgR^{105}$ wherein $R^{105}$ is halogen), followed by oxidation of the resulting secondary alcohol. Oxidation of the secondary alcohols to the corresponding ketones can be achieved by reaction conditions that are well known in the art, for example, by treatment with Jones reagent or pyridinium chlorochromate, or via Swern oxidation conditions.

Condensation of ketones or aldehydes of formula (19) wherein $R^c$ is hydrogen or alkyl with hydroxyamine ethers of formula $H_2NOR^3$ provides compounds of formula (20).

Transition metal cross-coupling of halides of formula (19) wherein $R^c$ is alkyl with a metalated vinyl ether of formula (21a) wherein M is trialkyltin or B(Oalkyl)$_2$ in the presence of a palladium catalyst (e.g. tetrakis(triphenylphosphine)palladium(0), followed by acidic hydrolysis conditions provide ketones of formula (21).

Condensation of ketones or aldehydes of formula (19) wherein $R^c$ is hydrogen or alkyl with hydrazines or hydrazides having formula $H_2NN(R^{c'})(R^3)$ or $H_2NN(R^{c''})C(O)R^3$ respectively provides compounds of formula (22) and (23) respectively. The conversion is generally conducted in an alcoholic solvent such as ethanol at a pH of about 4-8.

Many hydroxyamine ethers and hydrazines are either commercially available or may be prepared using methodologies similar to those known in the art. For example, hydroxylamine ethers may be obtained from alcohols of formula $R^3OH$ using similar or modification of the procedures described in Chem. Commun., 2000, 975-976. Alternatively, hydroxyamine ethers may be prepared by (a) treatment of N-hydroxyphthalimide with boronic acids of formula $R^3B(OH)_2$ via a copper mediated cross-coupling reaction conditions, and (b) treating the resulting intermediates with hydrazine monohydrate in a solvent such as, but not limited to chloroform, methanol or mixtures thereof. Step (a) is generally conducted in the presence of a copper salt, a base and in a solvent such as, but not limited to, dichloromethane or 1,2-dichloroethane, or mixtures thereof, and optionally in the presence of molecular sieves. The reaction is generally conducted at temperatures ranging from about room temperature to about 150° C. Examples of copper salts include, but are not limited, to Cu(CO$_2$CH$_3$)$_2$, CuCl, and CuBr.S(CH$_3$)$_2$. Examples of bases include, but are not limited to pyridine, 4-dimethylaminopyridine, and triethylamine.

Aryl or heteroaryl hydrazines are well known and many are available form commercial sources. Alternatively, monosubstituted hydrazines of formula $G^2N(R^c)NH_2$ wherein $G^2$ is aryl or heteroaryl, and $R^{c'}$ is hydrogen, can be prepared from the corresponding aryl or heteroaryl amines by diazotization, followed by treatment of the diazonium salt with hydrazine monohydrate. 1,1-Disubstituted hydrazines of formula $G^2N(R^{c'})NH_2$ wherein $G^2$ is aryl or heteroaryl, and $R^{c'}$ is alkyl or haloalkyl can be prepared from the secondary amines of formula $G^2N(R^{c'})(H)$ wherein $R^{c'}$ is alkyl or haloalkyl, by nitrosation (for example, nitrous acid or isoamyl nitrite), followed by reduction of the nitrosamine (for example, using zinc and acetic acid).

Hydrazides of formula $H_2NN(R^{c''})C(O)R^3$ can be prepared using methodologies analogous to those known in the literature, for example, by acylating acid chlorides of formula $R^3C(O)Cl$ (prepared from the corresponding acids) with appropriate hydrazines of formula $H_2NN(R^{c''})(H)$. many hydrazines of formula $H_2NN(R^{c''})(H)$ are commercially available. Alternatively, hydrazines of formula hydrazines of formula $H_2NN(R^{c''})(H)$ wherein $R^{c''}$ is alkyl or haloalkyl may be synthesized from the reaction of $R^{c''}R^{107}$ wherein $R^{107}$ is halogen or a sulfonate ester with di-t-butyl azodicarboxylate and triphenylphosphine, followed by treatment with acid.

Scheme 6

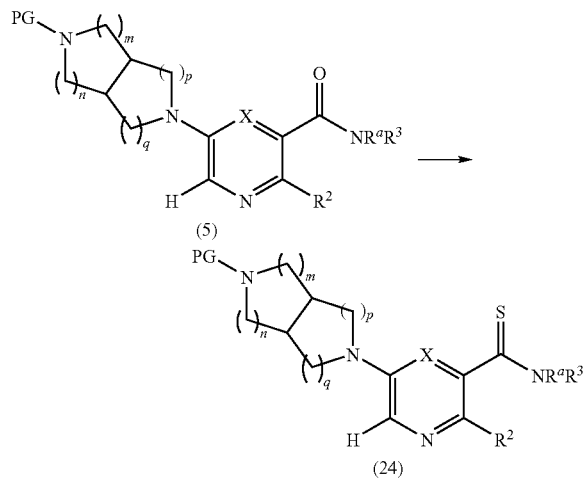

Compounds of general formula (I) wherein $L^1$ is —C(S)N($R^a$)— can be prepared by treating compounds of formula (5) with Lawesson's reagent in a solvent such as toluene.

Removal of the nitrogen protecting group of compounds of formula (12), (13), (14), (15), (20), (21), (22), (23), and (24) as described in Scheme 1, provides compounds of general formula (I).

$R^1$ group may also be introduced to the intermediates such as those of formula (4), (8), (9), (11), (12), (13), (14), (15), (19), (20), (21), (22), (23), and (24) using methods described in Scheme 1 after removal of the nitrogen protecting group.

It will be appreciated that the synthetic schemes and specific examples as illustrated in the Examples section are illustrative and are not to be read as limiting the scope of the invention as it is defined in the appended claims. All alternatives, modifications, and equivalents of the synthetic methods and specific examples are included within the scope of the claims.

Optimum reaction conditions and reaction times for each individual step may vary depending on the particular reactants employed and substituents present in the reactants used. Unless otherwise specified, solvents, temperatures and other reaction conditions may be readily selected by one of ordinary skill in the art. Specific procedures are provided in the Examples section. Reactions may be worked up in the convention manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or may be prepared by one skilled in the art from commercially available materials using methods described in the chemical literature.

Routine experimentations, including appropriate manipulation of the reaction conditions, reagents and sequence of the synthetic route, protection of any chemical functionality that may not be compatible with the reaction conditions, and deprotection at suitable point in the reaction sequence of the method are included in the scope of the invention. Suitable protecting groups and the methods for protecting and deprotecting different substituents using such suitable protecting groups are well known to those skilled in the art; examples of which may be found in T. Greene and P. Wuts, Protecting Groups in Chemical Synthesis ($3^{rd}$ ed.), John Wiley & Sons, NY (1999), which is incorporated herein by reference in its entirety. Synthesis of the compounds of the invention may be accomplished by methods analogous to those described in the synthetic schemes described above and in specific examples.

Starting materials, if not commercially available, may be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound of the invention is required, it may be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound of the invention is required, it may be obtained by carrying out one of the above procedures using a pure geometric isomer as a starting material, or by resolution of a mixture of the geometric isomers of the compound or intermediates using a standard procedure such as chromatographic separation.

EXAMPLES

The compounds and processes of the invention will be better understood by reference to the following examples and reference examples, which are intended as an illustration of and not a limitation upon the scope of the invention.

Example 1

N-(3,5-dimethylphenyl)-6-((3aR,6aS)-hexahydropyrrolo[3,4-c]pyrrol-2(1H)-yl)pyrazine-2-carboxamide Example 1A (3aR,6aS)-5-benzyltetrahydropyrrolo[3,4-c]pyrrole-1,3(2H,3aH)-dione A solution of N-benzyl-N-methoxymethyl-N-(trimethylsilylmethyl)amine (76.68 g, 0.29 mol, prepared as in Organic Syntheses (1989), 67, 133-140) in dichloromethane (130 mL) was added to an ice-cooled mixture of maleimide (25.53 g, 0.26 mol) and trifluoroacetic acid (2.2 mL, 0.028 mol) in dichloromethane (350 ml) over 40 min so that the reaction temperature remained between 0-5° C. The resulting bright yellow solution was allowed to warm gradually and stirred at room temperature for 27 h. The mixture was washed with saturated $NaHCO_{3(aq)}$ (80 mL) and the organic phase was dried ($MgSO_4$) and concentrated under vacuum. The residual oil was stirred with 10% EtOAc-heptane (300 mL) for 15 h, and the resulting precipitate was isolated by filtration, washed with 10% EtOAc-heptane (150 mL) and dried under vacuum at 50° C. to provide the crude, title compound as a white solid (54.25 g). This was stirred with methanol (500 mL) and 50% aqueous $H_2NOH$ (4.2 mL) at room temperature for 20 h. The mixture was concentrated under vacuum and the residue was taken up in EtOAc (500 mL) and filtered to remove some insoluble material. The filtrate was concentrated under vacuum to leave the pure, title compound as an off-white solid (49.9 g, 83% yield). $^1H$ NMR (300 MHz, $CD_3OD$) δ ppm 2.32-2.43 (m, 2H), 3.18 (d, J=9.8 Hz, 2H), 3.20-3.26 (m, 2H), 3.59 (s, 2H), 7.13-7.35 (m, 5H); MS (DCI/$NH_3$) m/z 231 $(M+H)^+$.

Example 1B (3aR,6aS)-tert-butyl 5-benzylhexahydropyrrolo[3,4-c]pyrrole-2(1H)-carboxylate A three-necked, 2 L flask with mechanical stirrer, thermometer, and addition funnel was charged with $LiAlH_4$ (16.9 g, 0.445 mol) and THF (200 mL). The slurry was cooled in ice under a nitrogen atmosphere as a solution of the product from Example 1A (49.0 g, 0.202 mol) in THF (250 mL) was added drop-wise over 20 min such that the temperature remained below 14° C. After the addition was completed, the reaction mixture was stirred for 40 min with ice cooling, then heated at reflux for 3 h. The mixture was again cooled in ice and quenched by cautious, successive addition of water (17 mL), 15% $NaOH_{(aq)}$ (17 mL), and water (51 mL). The resulting slurry was filtered, and the cake washed well with EtOAc (2×400 mL). The combined filtrate and wash was concentrated under vacuum to provide a colorless oil (43.5 g), which was dissolved in dichloromethane (200 mL). The solution was stirred with ice cooling as di-tert-butyl dicarbonate (46.3 g, 0.212 mol) was added gradually (gas evolution), and the resulting solution was allowed to warm to ambient temperature and stirred for 1 h. Aspartic acid (5.3 g, 0.04 mol) was added, and the mixture was stirred for 30 min, then transferred to a separatory funnel and washed with 1N NaOH(aq) (100 mL). The organic layer was dried ($Na_2SO_4$) and concentrated to provide the titled compound as a colorless oil, of sufficient purity for the next step (64.73 g, 108%). $^1H$ NMR (300 MHz, $CD_3OD$) δ ppm 1.45 (s, 9H), 2.34 (dd, J=9.3, 3.9 Hz, 2H), 2.69-2.78 (m, 2H), 2.78-2.88 (m, 2H), 3.20-3.30 (m, 2H), 3.39-3.50 (m, 2H), 3.59 (s, 2H), 7.15-7.39 (m, 5H); MS (DCI/$NH_3$) m/z 303 $(M+H)^+$.

Example 1C (3aR,6aS)-tert-butyl hexahydropyrrolo[3,4-c]pyrrole-2(1H)-carboxylate The crude product from Example 1B (64.70 g, 0.212 mol) from Example 1B was dissolved in methanol (250 mL). Pearlman's catalyst (Pd(OH)$_2$, 20% on C, 6.5 g) was added, and the mixture was agitated at 50° C. under hydrogen (60 psi) for 4 h. The mixture was cooled to room temperature, filtered under nitrogen to remove the catalyst, and the filtrate was concentrated under vacuum to a pale oil (46.55 g). This was dissolved in ether (150 mL), applied to a column of silica gel (300 g), and eluted with ether (1 L). The silica was then eluted with methanol (2 L) and the methanol fraction was concentrated under vacuum. The residue was taken up in EtOAc (500 mL), filtered to remove insoluble material, and concentrated under vacuum to provide the titled compound as an off-white solid (33.84 g, 75% for steps B and C), of sufficient purity for use in subsequent operations. $^1H$ NMR (300 MHz, $CD_3OD$) δ ppm 1.45 (s, 9H), 2.65 (dd, J=11.5, 4.4 Hz, 2H), 2.75-2.89 (m, 2H), 3.01-3.11 (m, 2H), 3.20 (dd, J=11.5, 3.7 Hz, 2H), 3.47-3.58 (m, 2H).

Example 1D

Methyl 4-oxy-2-pyrazinecarboxylate

Methyl 2-pyrazinecarboxylate (Pyrazine Specialists, 10.04 g, 72.2 mmol) was suspended in 1,2-dichloroethane (100 mL). To the reaction mixture was added mCPBA (32.35 g, 77%, 144 mmol). The reaction was stirred at 60° C. for 16 h. The reaction was then allowed to cool to ambient temperature and diluted with $CH_2Cl_2$ (300 mL). The precipitate was filtered off and washed with additional $CH_2Cl_2$ (3×35 mL). The filtrates were combined, dried over $K_2CO_3$, filtered and concentrated under vacuum. The residue was suspended in hexane (50 mL). The title compound was isolated by filtration, washed with additional hexane (2×50 mL) to afford a slightly yellow solid (7.22 g, 64%). $^1H$ NMR (DMSO-$d_6$, 300 MHz) δ ppm 3.91 (s, 3H), 8.54 (dd, J=4.07, 1.69 Hz, 1H), 8.64-8.67 (m, 2H). MS (DCI/$NH_3$) m/z 155 $(M+H)^+$.

Example 1E

Methyl 6-chloro-2-pyrazinecarboxylate

The product from Example 1D (7.18 g, 45.9 mmol) was dissolved in $SOCl_2$ (50 mL, 687 mmol). The reaction was heated to reflux for 8 h and then allowed to cool to ambient temperature. The $SOCl_2$ was removed under reduced pressure, and the residue was quenched with water (50 mL) at 0° C. The mixture was neutralized by the addition of 1M $K_2CO_3$ (aq) and extracted with $CH_2Cl_2$ (5×100 mL). The organic extracts were combined, washed with brine (100 mL), dried over $Na_2SO_4$, filtered and concentrated under vacuum. The residue was purified by silica gel chromatography (5% EtOAc in $CH_2Cl_2$, $R_f$=0.35) to afford the title compound as a thick oil that slowly solidified (7.16 g, 67%). $^1H$ NMR (DMSO-$d_6$, 300 MHz) δ ppm 3.94 (s, 3H), 9.07 (s, 1H), 9.19 (s, 1H). MS (DCI/$NH_3$) m/z 190 $(M+NH_4)^+$.

Example 1F (3aR,6aS)-tert-butyl 5-(6-(methoxycarbonyl)pyrazin-2-yl)hexahydropyrrolo[3,4-c]pyrrole-2(1H)-carboxylate The product from Example 1E (1.74 g, 10.08 mmol) was dissolved in DMSO (10 mL). The product from Example 1C (2.29 g, 10.79 mmol) and sodium carbonate (1.61 g, 15.19 mmol) were added to the reaction mixture. The reaction was stirred at 120° C. for 16 h. The reaction was then allowed to cool to ambient temperature, diluted with water (100 mL) and extracted with $CH_2Cl_2$ (4×100 mL). The organic extracts were combined and washed with water (100 mL) and brine (100 mL), dried over MgSO$_4$, filtered and concentrated under vacuum. The residue was purified by silica gel chromatography (EtOAc, R$_f$=0.36) to afford the title compound as a thick oil that slowly solidified (2.78 g, 78%). MS (DCI/NH$_3$) m/z 349 (M+H)$^+$.

Example 1G 6-((3aR,6aS)-5-(tert-butoxycarbonyl)hexahydropyrrolo[3,4-c]pyrrol-2(1H)-yl)pyrazine-2-carboxylic Acid The product from Example 1F (1.13 g, 3.24 mmol) was dissolved in EtOH (16 mL). 1M NaOH (16 mL) was added, and the reaction stirred at ambient temperature for 1 h. The reaction mixture was acidified to pH≈3 with 1 M HCl (aq). The mixture was then diluted with water (100 mL) and extracted with CH$_2$Cl$_2$ (3×100 mL). The organic extracts were combined, washed with brine (100 mL), dried over Na$_2$SO$_4$, filtered, and concentrated to provide the title compound as an amorphous solid (1.05 g, 97%). MS (DCI/NH$_3$) m/z 335 (M+H)$^+$.

Example 1H (3aR,6aS)-tert-butyl 5-(6-(3,5-dimethylphenylcarbamoyl)pyrazin-2-yl)hexahydropyrrolo[3,4-c]pyrrole-2(1H)-carboxylate The product from Example 1G (101.9 mg, 0.30 mmol) was dissolved in CH$_2$Cl$_2$ (3 mL). 3,5-dimethylaniline (110 μL, 0.88 mmol), HOBt (53.5 mg, 0.40 mmol), DMAP (10.4 mg, 0.085 mmol) and EDCI (94.3 mg, 0.49 mmol) were added to the reaction mixture. The reaction was stirred at ambient temperature for 5 h. The reaction mixture was concentrated under vacuum and the residue was purified by preparative HPLC on a Waters Nova-Pak® HR C18 6 μm 60 Å Prep-Pak® cartridge column (40 mm×100 mm) using a gradient of 10% to 100% acetonitrile in 10 mM aqueous ammonium acetate over 12 min at a flow rate of 70 mL/min to provide the title compound (109.0 mg, 83%). MS (DCI/NH$_3$) m/z 438 (M+H)$^+$.

Example 1I

N-(3,5-dimethylphenyl)-6-((3aR,6aS)-hexahydropyrrolo[3,4-c]pyrrol-2(1H)-yl)pyrazine-2-carboxamide The product from Example 1H (106.8 mg, 0.24 mmol) was dissolved in CH$_2$Cl$_2$ (5 mL). TFA (1 mL, 13 mmol) was added to the reaction mixture. The reaction was stirred at ambient temperature for 1 h then concentrated under vacuum. The residue was dissolved in a minimal amount of MeOH, then triturate by slow addition of 9:1 Et$_2$O/MeOH. The product was isolated by filtration, washed with additional Et$_2$O (5×1 mL) and dried in the vacuum oven overnight to afford the TFA salt of title compound as a white powder (74.6 mg, 69%). $^1$H NMR (CD$_3$OD, 400 MHz) δ ppm 2.32 (s, 6H), 3.29-3.35 (m, 4H), 3.63-3.68 (m, 2H), 3.74-3.84 (m, 4H), 6.83 (s, 1H), 7.34 (s, 2H), 8.17 (s, 1H), 8.53 (s, 1H); MS (DCI/NH$_3$) m/z 338 (M+H)$^+$.

Example 2

6-((3aR,6aS)-hexahydropyrrolo[3,4-c]pyrrol-2(1H)-yl)-N-(3-iodophenyl)pyrazine-2-carboxamide Example 2A (3aR,6aS)-tert-butyl 5-(6-(3-iodophenylcarbamoyl)pyrazin-2-yl)hexahydropyrrolo[3,4-c]pyrrole-2(1H)-carboxylate The product from Example 1G was reacted with 3-indoaniline, EDCI, HOBt and DMAP in CH$_2$Cl$_2$ as described in Example 1H to afford the title compound. MS (DCI/NH$_3$) m/z 536 (M+H)$^+$.

Example 2B 6-((3aR,6aS)-hexahydropyrrolo[3,4-c]pyrrol-2(1H)-yl-N-(3-iodophenyl)pyrazine-2-carboxamide The product from Example 2A was reacted with TFA in CH$_2$Cl$_2$ as described in example 1I to afford the title compound as the TFA salt. $^1$H NMR (CD$_3$OD, 300 MHz) δ ppm 3.26-3.38 (m, 4H), 3.63-3.69 (m, 2H), 3.76-3.87 (m, 4H), 7.15 (t, J=8.1 Hz, 1H), 7.51-7.54 (m, 1H), 7.76-7.79 (m, 1H), 8.20-8.21 (m, 2H), 8.55 (s, 1H); MS (DCI/NH$_3$) m/z 338 (M+H)$^+$.

Example 3

N-(4-chlorophenyl)-6-((3aR,6aS)-hexahydropyrrolo[3,4-c]pyrrol-2(1H)-yl)pyrazine-2-carboxamide Example 3A (3aR,6aS)-tert-butyl 5-(6-(4-chlorophenylcarbamoyl)pyrazin-2-yl)hexahydropyrrolo[3,4-c]pyrrole-2(1H)-carboxylate The product from Example 1G was reacted with 4-chloroaniline, EDCI, HOBt and DMAP in CH$_2$Cl$_2$ as described in example 1H to afford the title compound. MS (DCI/NH$_3$) m/z 444 (M+H)$^+$.

Example 3B

N-(4-chlorophenyl)-6-((3aR,6aS)-hexahydropyrrolo[3,4-c]pyrrol-2(1H)-yl)pyrazine-2-carboxamide The product from Example 3A was reacted with TFA in CH$_2$Cl$_2$ as described in Example 1I to afford the title compound as the TFA salt. $^1$H NMR (CD$_3$OD, 300 MHz) δ ppm 3.26-3.38 (m, 4H), 3.63-3.69 (m, 2H), 3.76-3.87 (m, 4H), 7.36-7.41 (m, 2H), 7.74-7.79 (m, 2H), 8.21 (s, 1H), 8.55 (s, 1H); MS (DCI/NH$_3$) m/z 344 (M+H)$^+$.

Example 4

N-(3,5-difluorophenyl)-6-((3aR,6aS)-hexahydropyrrolo[3,4-c]pyrrol-2(1H)-yl)pyrazine-2-carboxamide

Example 4A (3aR,6aS)-tert-butyl 5-(6-(3,5-difluorophenylcarbamoyl)pyrazin-2-yl)hexahydropyrrolo[3,4-c]pyrrole-2(1H)-carboxylate The product from Example 1G was reacted with 3,5-difluoraniline, EDCI, HOBt and DMAP in $CH_2Cl_2$ as described in Example 1H to afford the title compound. MS ($DCI/NH_3$) m/z 446 $(M+H)^+$.

Example 4B

N-(3,5-difluorophenyl)-6-((3aR,6aS)-hexahydropyrrolo[3,4-c]pyrrol-2(1H)-yl)pyrazine-2-carboxamide The product from Example 4A was reacted with TFA in $CH_2Cl_2$ as described in example 1I to afford the title compound as the TFA salt. $^1$H NMR ($CD_3OD$, 300 MHz) δ ppm 3.26-3.36 (m, 4H), 3.63-3.69 (m, 2H), 3.77-3.84 (m, 4H), 6.75 (tt, J=9.11, 2.25 Hz, 1H) 7.47-7.54 (m, 2H), 8.22 (s, 1H), 8.55 (s, 1H); MS ($DCI/NH_3$) m/z 346 $(M+H)^+$.

Example 5

N-(3,4-dichlorobenzyl)-6-((3aR,6aS)-hexahydropyrrolo[3,4-c]pyrrol-2(1H)-yl)pyrazine-2-carboxamide

Example 5A (3aR,6aS)-tert-butyl 5-(6-(3,4-dichlorobenzylcarbamoyl)pyrazin-2-yl)hexahydropyrrolo[3,4-c]pyrrole-2(1H)-carboxylate The product from Example 1G was reacted with 3,4-dichlorobenzylamine, EDCI, HOBt and DMAP in $CH_2Cl_2$ as described in Example 1H to afford the title compound. MS ($DCI/NH_3$) m/z 492 $(M+H)^+$.

Example 5B

N-(3,4-dichlorobenzyl)-6-((3aR,6aS)-hexahydropyrrolo[3,4-c]pyrrol-2(1H)-yl)pyrazine-2-carboxamide The product from Example 5A was reacted with TFA in $CH_2Cl_2$ as described in Example 1I to afford the title compound as the TFA salt. $^1$H NMR ($CD_3OD$, 300 MHz) δ ppm 3.21-3.34 (m, 4H), 3.59-3.66 (m, 2H), 3.70-3.80 (m, 4H), 4.58 (d, J=6.44 Hz, 2H), 7.28 (dd, J=8.14, 2.03 Hz, 1H), 7.46-7.50 (m, 2H), 8.17 (s, 1H), 8.48 (s, 1H), 9.11 (t, J=6.43); MS ($DCI/NH_3$) m/z 346 $(M+H)^+$.

Example 6

N-(3-chlorophenyl)-6-((3aR,6aS)-hexahydropyrrolo[3,4-c]pyrrol-2(1H)-yl)pyrazine-2-carboxamide

Example 6A (3aR,6aS)-tert-butyl 5-(6-(3-chlorophenylcarbamoyl)pyrazin-2-yl)hexahydropyrrolo[3,4-c]pyrrole-2(1H)-carboxylate The product from Example 1G was reacted with 3-chloroaniline, EDCI, HOBt and DMAP in $CH_2Cl_2$ as described in Example 1H to afford the title compound. MS ($DCI/NH_3$) m/z 444 $(M+H)^+$.

Example 6B

N-(3-chlorophenyl)-6-((3aR,6aS)-hexahydropyrrolo[3,4-c]pyrrol-2(1H)-yl)pyrazine-2-carboxamide The product from Example 6A was reacted with TFA in $CH_2Cl_2$ as described in Example 1I to afford the title compound as the TFA salt. $^1$H NMR ($CD_3OD$, 300 MHz) δ ppm 3.26-3.36 (m, 4H), 3.63-3.69 (m, 2H), 3.76-3.87 (m, 4H), 7.16-7.19 (m, 1H), 7.36 (t, J=8.14 Hz, 1H), 7.64-7.67 (m, 1H), 7.91-7.92 (m, 1H), 8.22 (s, 1H), 8.55 (s, 1H); MS ($DCI/NH_3$) m/z 344 $(M+H)^+$.

Example 7

6-((3aR,6aS)-hexahydropyrrolo[3,4-c]pyrrol-2(1H)-yl)-N-phenethylpyrazine-2-carboxamide

Example 7A (3aR,6aS)-tert-butyl 5-(6-(phenethylcarbamoyl)pyrazin-2-yl)hexahydropyrrolo[3,4-c]pyrrole-2(1H)-carboxylate The product from Example 1G was reacted with phenethylamine, EDCI, HOBt and DMAP in $CH_2Cl_2$ as described in Example 1H to afford the title compound. MS ($DCI/NH_3$) m/z 438 $(M+H)^+$.

Example 7B 6-((3aR,6aS)-hexahydropyrrolo[3,4-c]pyrrol-2(1H)-yl)-N-phenethylpyrazine-2-carboxamide The product from Example 7A was reacted with TFA in $CH_2Cl_2$ as described in Example 1I to afford the title compound as the TFA salt. $^1$H NMR ($CD_3OD$, 300 MHz) δ ppm 2.92 (t, J=2.92 Hz, 2H), 3.21-3.34 (m, 4H), 3.62-3.75 (m, 8H), 7.20-7.33 (m, 5H), 8.15 (s, 1H), 8.43 (s, 1H); MS ($DCI/NH_3$) m/z 338 $(M+H)^+$.

Example 8

6-((3aR,6aS)-hexahydropyrrolo[3,4-c]pyrrol-2(1H)-yl)-N-(3-isopropylphenyl)pyrazine-2-carboxamide

Example 8A (3aR,6aS)-tert-butyl 5-(6-(3-isopropylphenylcarbamoyl)pyrazin-2-yl)hexahydropyrrolo[3,4-c]pyrrole-2(1H)-carboxylate The product from Example 1G was reacted with 3-isopropylaniline, EDCI, HOBt and DMAP in $CH_2Cl_2$ as described in Example 1H to afford the title compound. MS (DCI/$NH_3$) m/z 452 (M+H)$^+$.

Example 8B 6-((3aR,6aS)-hexahydropyrrolo[3,4-c]pyrrol-2(1H)-yl)-N-(3-isopropylphenyl)pyrazine-2-carboxamide The product from Example 8A (71.7 mg, 0.16 mmol) was dissolved in $CH_2Cl_2$ (5 mL). TFA (0.5 mL, 6.5 mmol) was added to the reaction mixture. The reaction was stirred at ambient temperature for 1 h, and concentrated. The residue was partition between 1M NaOH (50 mL) and $CH_2Cl_2$ (3×35 mL). The combined organic layers were dried over $Na_2SO_4$ and concentrated under vacuum. The residue was dissolve in $Et_2O$/MeOH 9.1 (10 mL) and treated with fumaric acid to afford the title compound as fumaric acid salt. $^1$H NMR ($CD_3OD$, 300 MHz) δ ppm 1.28 (d, J=6.78, 6H), 2.93 (sept., J=6.88 Hz, 1H), 3.26-3.37 (m, 4H), 3.60-3.67 (m, 2H), 3.76-3.87 (m, 4H), 6.66 (s, 2H) 7.07 (d, J=7.46 Hz, 1H), 7.30 (t, J=7.97 Hz, 1H), 7.55-7.57 (m, 1H), 7.62 (t, J=1.86 Hz, 1H), 8.20 (s, 1H), 8.55 (s, 1H); MS (DCI/$NH_3$) m/z 352 (M+H)$^+$.

Example 9

N-benzyl-6-((3aR,6aS)-hexahydropyrrolo[3,4-c]pyrrol-2(1H)-yl)pyrazine-2-carboxamide

Example 9A (3aR,6aS)-tert-butyl 5-(6-(benzylcarbamoyl)pyrazin-2-yl)hexahydropyrrolo[3,4-c]pyrrole-2(1H)-carboxylate The product from Example 1F (201.4 mg, 0.58 mmol) and $MgCl_2$ (112.7 mg, 1.18 mmol) were suspended in THF (6 mL) and stirred at ambient temperature for 5 min. Benzylamine (150 μL, 1.37 mmol) was added and the reaction was stirred at 40° C. for 18 hours. The reaction mixture was then poured into water (50 mL) and extracted with $CH_2Cl_2$ (3×35 mL). The organic extracts were combined, dried over $Na_2SO_4$, filtered and concentrated under vacuum. The residue was purified by preparative HPLC on a Waters Nova-Pak® HR C18 Prep-Pak® cartridge column (40 mm×100 mm) using a gradient of 10% to 100% acetonitrile in 10 mM aqueous ammonium acetate over 12 min at a flow rate of 70 mL/min to provide the title compound (183.8 mg, 75%). MS (DCI/$NH_3$) m/z 424 (M+H)$^+$.

Example 9B

N-benzyl-6-((3aR,6aS)-hexahydropyrrolo[3,4-c]pyrrol-2(1H)-yl)pyrazine-2-carboxamide The product from 9A was reacted with TFA in $CH_2Cl_2$ as described in example 1I to afford the title compound as the TFA salt. $^1$H NMR ($CD_3OD$, 300 MHz) δ ppm 3.21-3.34 (m, 4H), 3.58-3.64 (m, 2H), 3.69-3.78 (m, 4H), 4.61 (s, 2H), 7.24-7.36 (m, 5H), 8.16 (s, 1H), 8.48 (s, 1H); MS (DCI/$NH_3$) m/z 324 (M+H)$^+$.

Example 10

6-((3aR,6aS)-hexahydropyrrolo[3,4-c]pyrrol-2(1H)-yl)-N-(1-phenylethyl)pyrazine-2-carboxamide

Example 10A (3aR,6aS)-tert-butyl 5-(6-(1-phenylethylcarbamoyl)pyrazin-2-yl)hexahydropyrrolo[3,4-c]pyrrole-2(1H)-carboxylate The product from Example 1F was reacted with α-methylbenzylamine and $MgCl_2$ in THF as describe in example 9A to afford the title compound. MS (DCI/$NH_3$) m/z 438 (M+H)$^+$.

Example 10B 6-((3aR,6aS)-hexahydropyrrolo[3,4-c]pyrrol-2(1H)-yl)-N-(1-phenylethyl)pyrazine-2-carboxamide The product from Example 10A was reacted with TFA in $CH_2Cl_2$ as described in Example 1I to afford the title compound as the TFA salt. $^1$H NMR ($CD_3OD$, 300 MHz) δ ppm 1.60 (d, J=7.12 Hz, 6H), 3.23-3.33 (m, 4H), 3.60-3.82 (m, 6H), 5.19-5.29 (m, 1H), 7.23-7.41 (m, 5H), 8.17 (s, 1H), 8.44 (s, 1H), 8.51 (d, J=8.45 Hz, 1H); MS (DCI/$NH_3$) m/z 338 (M+H)$^+$.

Example 11

N-benzyl-6-((3aR,6aS)-hexahydropyrrolo[3,4-c]pyrrol-2(1H)-yl)-N-methylpyrazine-2-carboxamide

Example 11A (3aR,6aS)-tert-butyl 5-(6-(benzyl(methyl)carbamoyl)pyrazin-2-yl)hexahydropyrrolo[3,4-c]pyrrole-2(1H)-carboxylate The product from Example 1F was reacted with N-benzylmethylamine and $MgCl_2$ in THF as describe in Example 9A to afford the title compound. MS (DCI/$NH_3$) m/z 438 (M+H)$^+$.

Example 11B

N-benzyl-6-((3aR,6aS)-hexahydropyrrolo[3,4-c]pyrrol-2(1H)-yl)-N-methylpyrazine-2-carboxamide The product from Example 11A was reacted with TFA in $CH_2Cl_2$ and processed as described in example 8B to afford the title compound as the fumaric acid salt. $^1$H NMR ($CD_3OD$, 300 MHz) δ ppm 3.01 (d, J=5.09 Hz, 3H), 3.07-3.74 (m, 10H), 4.67-4.75 (m, 2H), 6.68 (s, 2H), 7.29-7.39 (m, 5H), 8.01-8.07 (m, 2H); MS (DCI/$NH_3$) m/z 338 (M+H)$^+$.

Example 12

6-((3aR,6aS)-hexahydropyrrolo[3,4-c]pyrrol-2(1H)-yl)-N-(2-methylbenzyl)pyrazine-2-carboxamide

Example 12A

6-Chloro-pyrazine-2-carboxylic Acid 2-methyl-benzylamide

The product from Example 1E (1.00 g, 5.79 mmol) and MgCl$_2$ (1.11 g, 11.7 mmol) were suspended in THF (25 mL) and stirred at ambient temperature for 5 min. 2-Methylbenzylamine (1.8 mL, 14.5 mmol) was added, and the reaction was stirred at ambient temperature for 16 h. The reaction mixture was diluted with water (150 mL) and extracted with CH$_2$Cl$_2$ (4×100 mL). The organic extracts were combined and washed with 0.25M HCl (aq) (100 mL) and brine (100 mL), dried over Na$_2$SO$_4$, filtered and concentrated under vacuum. The residue was purified by silica gel chromatography to afford the title compound as a white solid (1.35 g, 89%). $^1$H NMR (DMSO-d$_6$, 300 MHz) δ ppm 2.33 (s, 3H), 4.48 (d, J=6.10 Hz, 2H), 7.12-7.26 (m, 4H), 9.02 (s, 1H), 9.15 (s, 1H) 9.33 (t, J=5.76, 1H). MS (DCI/NH$_3$) m/z 262 (M+H)$^+$.

Example 12B (3aR,6aS)-tert-butyl 5-(6-(2-methylbenzylcarbamoyl)pyrazin-2-yl)hexahydropyrrolo[3,4-c]pyrrole-2(1H)-carboxylate The product from Example 12A was reacted with the product from Example 1C and sodium carbonate in DMSO as described in Example 1F to afford the title compound. MS (DCI/NH$_3$) m/z 438 (M+H)$^+$.

Example 12C 6-((3aR,6aS)-hexahydropyrrolo[3,4-c]pyrrol-2(1H)-yl)-N-(2-methylbenzyl)pyrazine-2-carboxamide The product from Example 12B was reacted with TFA in CH$_2$Cl$_2$ as described in example 1I to afford the title compound as the TFA salt. $^1$H NMR (DMSO-d$_6$, 300 MHz) δ ppm 2.33 (s, 3H), 3.09-3.16 (m, 4H), 3.46-3.49 (m, 2H), 3.59-3.64 (m, 2H), 3.68-3.75 (m, 2H), 4.49 (d, J=6.10 Hz, 2H), 7.13-7.21 (m, 4H), 8.21 (s, 1H), 8.39 (s, 1H), 8.86-8.93 (m, 2H); MS (DCI/NH$_3$) m/z 338 (M+H)$^+$.

Example 13

6-((3aS,6aS)-hexahydropyrrolo[3,4-b]pyrrol-5(1H)-yl)-N-(2-methylbenzyl)pyrazine-2-carboxamide

Example 13A (3aS,6aS)-tert-butyl 5-(6-(2-methylbenzylcarbamoyl)pyrazin-2-yl)hexahydropyrrolo[3,4-b]pyrrole-1(2H)-carboxylate The product from Example 12A was reacted with (3aS,6aS)-tert-butyl hexahydropyrrolo[3,4-b]pyrrole-1(2H)-carboxylate (prepared as described in WO2001081347) and sodium carbonate in DMSO as described in Example 1F to afford the title compound. MS (DCI/NH$_3$) m/z 438 (M+H)$^+$.

Example 13B 6-((3aS,6aS)-hexahydropyrrolo[3,4-b]pyrrol-5(1H)-yl)-N-(2-methylbenzyl)pyrazine-2-carboxamide The product from Example 13A was reacted with TFA in CH$_2$Cl$_2$ as described in Example 1I to afford the title compound as the TFA salt. $^1$H NMR (DMSO-d$_6$, 300 MHz) δ ppm 1.87-1.95 (m, 1H), 2.14-2.26 (m, 1H), 2.33 (s, 3H), 3.18-3.57 (m, 4H), 3.71-3.78 (m, 2H), 4.01-4.05 (m, 1H), 4.32-4.36 (m, 1H), 4.43-4.57 (m, 2H), 7.13-7.21 (m, 4H), 8.26 (s, 1H), 8.43 (s, 1H), 8.86-8.96 (m, 2H); MS (DCI/NH$_3$) m/z 338 (M+H)$^+$.

Example 14

6-((3aR,6aR)-hexahydropyrrolo[3,4-b]pyrrol-1(2H)-yl)-N-(2-methylbenzyl)pyrazine-2-carboxamide

Example 14A (3aR,6aR)-tert-butyl 1-(6-(2-methylbenzylcarbamoyl)pyrazin-2-yl)hexahydropyrrolo[3,4-b]pyrrole-5(1H)-carboxylate The product from Example 12A was reacted with (3aR,6aR)-tert-butyl hexahydropyrrolo[3,4-b]pyrrole-5(1H)-carboxylate (prepared as described in WO2001081347) and sodium carbonate in DMSO as described in Example 1F to afford the title compound. MS (DCI/NH$_3$) m/z 438 (M+H)$^+$.

Example 14B 6-((3aR,6aR)-hexahydropyrrolo[3,4-b]pyrrol-1(2H)-yl)-N-(2-methylbenzyl)pyrazine-2-carboxamide The product from Example 14A was reacted with TFA in CH$_2$Cl$_2$ as described in Example 1I to afford the title compound as the TFA salt. $^1$H NMR (DMSO-d$_6$, 300 MHz) δ ppm 1.96-2.01 (m, 1H), 2.13-2.20 (m, 1H), 2.34 (s, 3H), 3.15-3.19 (m, 2H), 3.35-3.72 (m, 5H), 4.50 (d, J=6.10 Hz, 2H), 7.13-7.20 (m, 4H), 8.28 (s, 1H), 8.42 (s, 1H), 8.94 (t, J=6.44 Hz, 1H); MS (DCI/NH$_3$) m/z 338 (M+H)$^+$.

Example 15

6-((3aR,6aS)-hexahydropyrrolo[3,4-c]pyrrol-2(1H)-yl)-N-m-tolylpyrazine-2-carboxamide

Example 15A 6-chloropyrazine-2-carboxylic Acid

The product from Example 1E (1.78 g, 10.3 mmol) was dissolved in EtOH (25 mL). 1M NaOH (25 mL) was added, and the reaction stirred at ambient temperature for 2 h. The reaction mixture was acidified to pH≈3 with 1M HCl (aq). The mixture was then diluted with water (150 mL) and extracted with EtOAc (4×100 mL). The organic extracts were combined, washed with brine (100 mL), dried over Na$_2$SO$_4$, filtered and concentrated under vacuum to provide the title compound as a white solid (1.54 g, 94%). MS (DCI/NH$_3$) m/z 176 (M+NH$_4$)$^+$.

Example 15B 6-chloropyrazine-2-carbonyl Chloride

The product from Example 15A (1.47 g, 9.27 mmol) was suspended in CH$_2$Cl$_2$ (50 mL). Oxalyl chloride (1.40 mL, 16.0 mmol) and DMF (35 μL, 0.45 mmol) were added, and the reaction stirred at ambient temperature for 3 h. The reaction mixture was concentrated under vacuum and placed on a high vacuum line to provide the crude product (1.62 g, 99%) as a dark oil, which was used without addition purification.

Example 15C 6-chloro-N-m-tolylpyrazine-2-carboxamide

The product from Example 15B (950 mg, 5.37 mmol) was dissolved in $CH_2Cl_2$ (20 mL). Triethylamine (1.10 mL, 7.89 mmol) and m-toluidine (0.70 mL, 6.46 mmol) were added, and the reaction stirred at ambient temperature for 2 h. The reaction mixture was diluted with 0.1M HCl (100 mL) and extracted with $CH_2Cl_2$ (3×50 mL). The organic extracts were combined, washed with brine (50 mL), dried over $MgSO_4$, filtered and concentrated under vacuum. The residue was purified by silica gel chromatography (2.5% EtOAc in $CH_2Cl_2$, $R_f$=0.39) to afford the title compound as a white solid (1.11 g, 83%). MS ($DCI/NH_3$) m/z 248 $(M+H)^+$.

Example 15D (3aR,6aS)-tert-butyl 5-(6-(m-tolylcarbamoyl)pyrazin-2-yl)hexahydropyrrolo[3,4-c]pyrrole-2(1H)-carboxylate The product from Example 15C was reacted with the product from Example 1C and sodium carbonate in DMSO as described in Example 1F to afford the title compound. MS ($DCI/NH_3$) m/z 424 $(M+H)^+$.

Example 15E 6-((3aR,6aS)-hexahydropyrrolo[3,4-c]pyrrol-2(1H)-yl)-N-m-tolylpyrazine-2-carboxamide The product from Example 15D was reacted with TFA in $CH_2Cl_2$ as described in Example 1I to afford the title compound as the TFA salt. $^1$H NMR ($CD_3OD$, 300 MHz) δ ppm 2.37 (s, 3H), 3.27-3.38 (m, 4H), 3.62-3.69 (m, 2H), 3.79-3.87 (m, 4H), 7.01 (d, J=7.46 Hz, 1H), 7.23-7.29 (m, 1H), 7.54 (s, 2H), 8.20 (s, 1H), 8.55 (s, 1H), 9.90 (br s, 1H); MS ($DCI/NH_3$) m/z 324 $(M+H)^+$.

Example 16

6-((3aS,6aS)-hexahydropyrrolo[3,4-b]pyrrol-5(1H)-yl)-N-m-tolylpyrazine-2-carboxamide

Example 16A (3aS,6aS)-tert-butyl 5-(6-(m-tolylcarbamoyl)pyrazin-2-yl)hexahydropyrrolo[3,4-b]pyrrole-1(2H)-carboxylate The product from Example 15C was reacted with (3aS,6aS)-tert-butyl hexahydropyrrolo[3,4-b]pyrrole-1(2H)-carboxylate (prepared as described in WO2001081347) and sodium carbonate in DMSO as described in Example 1F to afford the title compound. MS ($DCI/NH_3$) m/z 424 $(M+H)^+$.

Example 16B 6-((3aS,6aS)-hexahydropyrrolo[3,4-b]pyrrol-5(1H)-yl)-N-m-tolylpyrazine-2-carboxamide The product from Example 16A was reacted with TFA in $CH_2Cl_2$ as described in Example 1I to afford the title compound as the TFA salt. $^1$H NMR ($CD_3OD$, 300 MHz) δ ppm 2.09-2.17 (m, 1H), 2.34-2.47 (m, 4H), 3.39-3.46 (m, 3H), 3.71-3.91 (m, 3H), 4.21 (dd, J=13.22, 1.70 Hz, 1H), 4.46-4.51 (m, 1H), 7.01 (d, J=8.14 Hz, 1H), 7.24-7.30 (m, 1H), 7.53-7.55 (m, 2H), 8.25 (s, 1H), 8.60 (s, 1H), 9.91 (br s, 1H); MS ($DCI/NH_3$) m/z 324 $(M+H)^+$.

Example 17

N-(3,5-dimethoxyphenyl)-6-((3aR,6aS)-hexahydropyrrolo[3,4-c]pyrrol-2(1H-yl)pyrazine-2-carboxamide

Example 17A 6-chloro-N-(3,5-dimethoxyphenyl)pyrazine-2-carboxamide

The product from Example 15B was reacted with 3,5-dimethoxyaniline and TEA in $CH_2Cl_2$ as described in Example 15C to afford the title compound. MS ($DCI/NH_3$) m/z 294 $(M+H)^+$.

Example 17B (3aR,6aS)-tert-butyl 5-(6-(3,5-dimethoxyphenylcarbamoyl)pyrazin-2-yl)hexahydropyrrolo[3,4-c]pyrrole-2(1H)-carboxylate The product from Example 17A was reacted with the product from Example 1C and sodium carbonate in DMSO as described in Example 1F to afford the title compound. MS ($DCI/NH_3$) m/z 470 $(M+H)^+$.

Example 17C

N-(3,5-dimethoxyphenyl)-6-((3aR,6aS)-hexahydropyrrolo[3,4-c]pyrrol-2(1H-yl)pyrazine-2-carboxamide The product from Example 17B was reacted with TFA in $CH_2Cl_2$ as described in Example 1I to afford the title compound as the TFA salt. $^1$H NMR ($CD_3OD$, 300 MHz) δ ppm 3.26-3.38 (m, 4H), 3.62-3.69 (m, 2H), 3.76-3.87 (m, 10H), 6.33 (t, J=2.2 Hz, 1H), 7.00 (d, J=2.3 Hz, 2H), 8.21 (s, 1H), 8.55 (s, 1H); MS ($DCI/NH_3$) m/z 370 $(M+H)^+$.

Example 18

6-((3aR,6aS)-hexahydropyrrolo[3,4-c]pyrrol-2(1H)-yl)-N-(3-isopropoxyphenyl)pyrazine-2-carboxamide

Example 18A 6-chloro-N-(3-isopropoxyphenyl)pyrazine-2-carboxamide

The product from Example 15B was reacted with 3-isopropoxyaniline and TEA in $CH_2Cl_2$ as described in Example 15C to afford the title compound. MS ($DCI/NH_3$) m/z 309 $(M+H)^+$.

Example 18B (3aR,6aS)-tert-butyl 5-(6-(3-isopropoxyphenylcarbamoyl)pyrazin-2-yl)hexahydropyrrolo[3,4-c]pyrrole-2(1H)-carboxylate The product from Example 18A was reacted with the product from Example 1C and sodium carbonate in DMSO as described in Example 1F to afford the title compound. MS (DCI/NH$_3$) m/z 468 (M+H)$^+$.

Example 18C 6-((3aR,6aS)-hexahydropyrrolo[3,4-c]pyrrol-2(1H)-yl)-N-(3-isopropoxyphenyl)pyrazine-2-carboxamide The product from Example 18B was reacted with TFA in CH$_2$Cl$_2$ and processed as described in Example 8B to afford the title compound as the fumaric acid salt. $^1$H NMR (CD$_3$OD, 300 MHz) δ ppm 1.33 (d, J=6.1 Hz, 6H), 3.26-3.38 (m, 4H), 3.63-3.67 (m, 2H), 3.76-3.85 (m, 4H), 4.62 (sept., J=6.1 Hz, 1H), 6.66 (s, 2H), 6.71-6.75 (m, 1H), 7.19-7.29 (m, 2H), 7.46 (t, J=2.2 Hz, 1H), 8.20 (s, 1H), 8.54 (s, 1H); MS (DCI/NH$_3$) m/z 368 (M+H)$^+$.

Example 19

(3aR,6aS)-2-(6-(3,5-difluorobenzyloxy)pyrazin-2-yl)octahydropyrrolo[3,4-c]pyrrole

Example 19A (3aR,6aS)-tert-butyl 5-(6-chloropyrazin-2-yl)hexahydropyrrolo[3,4-c]pyrrole-2(1H)-carboxylate 2,6-dichloropyrazine (1.02 g, 6.85 mmol) was dissolved in DMSO (7 mL). The product from Example 1C (1.61 g, 7.58 mmol) and N,N-diisopropylethylamine (1.5 mL, 8.61 mmol) were added to the reaction mixture. The reaction was stirred at ambient temperature for 23 h. The reaction was diluted with water (200 mL) and extracted with CH$_2$Cl$_2$ (4×100 mL). The organic extracts were combined and washed with and brine (150 mL), dried over MgSO$_4$, filtered and concentrated under vacuum. The residue was purified by silica gel chromatography (EtOAc, R$_f$=0.38) to afford the title compound as a white solid (1.99 g, 89%). MS (DCI/NH$_3$) m/z 325 (M+H)$^+$.

Example 19B (3aR,6aS)-tert-butyl 5-(6-(3,5-difluorobenzyloxy)pyrazin-2-yl)hexahydropyrrolo[3,4-c]pyrrole-2(1H)-carboxylate 3,5-difluorobenzylalcohol (200 μL, 1.77 mmol) and potassium tert-butoxide (90 mg, 0.80 mmol) in anhydrous DMSO (1 mL) were stirred at room temperature for 1 h. The product from Example 19A (101.3 mg, 0.31 mmol) was added and the reaction mixture was stirred at room temperature overnight (17H). The reaction mixture was diluted with MeOH (1 mL) and purified by preparative HPLC on a Waters Nova-Pak® HR C18 6 μm 60 Å Prep-Pak® cartridge column (40 mm×100 mm) using a gradient of 10% to 100% acetonitrile in 10 mM aqueous ammonium acetate over 12 min at a flow rate of 70 mL/min to provide the desired compound. MS (DCI/NH$_3$) m/z 433 (M+H)$^+$.

Example 19C (3aR,6aS)-2-(6-(3,5-difluorobenzyloxy)pyrazin-2-yl)octahydropyrrolo[3,4-c]pyrrole The product from Example 19B was reacted with TFA in CH$_2$Cl$_2$ and processed as described in Example 8B to afford the title compound as the fumaric acid salt. $^1$H NMR (CD$_3$OD, 300 MHz) δ ppm 3.18-3.33 (m, 4H), 3.55-3.67 (m, 6H), 5.39 (s, 2H), 6.67 (s, 2H), 6.87 (tt, J=9.2, 2.4 Hz, 1H), 7.01-7.07 (m, 2H), 7.47 (s, 1H), 7.52 (s, 1H); MS (DCI/NH$_3$) m/z 333 (M+H)$^+$.

Example 20

(3aR,6aS)-2-(6-(4-fluorophenethoxy)pyrazin-2-yl)octahydropyrrolo[3,4-c]pyrrole

Example 20A (3aR,6aS)-tert-butyl 5-(6-(4-fluorophenethoxy)pyrazin-2-yl)hexahydropyrrolo[3,4-c]pyrrole-2(1H)-carboxylate 4-Fluorophenethylalcohol (125 μL, 1.00 mmol) and potassium tert-butoxide (67.5 mg, 0.60 mmol) in anhydrous DMSO (1 mL) were reacted with the product from Example 19A (96.2 mg, 0.30 mmol) as described in Example 19B to afford the title compound. MS (DCI/NH$_3$) m/z 429 (M+H)$^+$.

Example 20B (3aR,6aS)-2-(6-(4-fluorophenethoxy)pyrazin-2-yl)octahydropyrrolo[3,4-c]pyrrole The product from Example 20A was reacted with TFA in CH$_2$Cl$_2$ as described in example 11 to afford the title compound as the TFA salt. $^1$H NMR (CD$_3$OD, 300 MHz) δ ppm 3.06 (t, J=7.0 Hz, 1H), 3.20-3.34 (m, 4H), 3.56-3.70 (m, 6H), 4.50 (t, J=7.0 Hz, 1H), 6.98-7.05 (m, 2H), 7.25-7.31 (m, 2H), 7.41 (s, 1H), 7.44 (s, 1H); MS (DCI/NH$_3$) m/z 329 (M+H)$^+$.

Example 21

(3aR,6aS)-2-(6-(2,2,2-trifluoro-1-phenylethoxy)pyrazin-2-yl)octahydropyrrolo[3,4-c]pyrrole

Example 21A (3aR,6aS)-tert-butyl 5-(6-(2,2,2-trifluoro-1-phenylethoxy)pyrazin-2-yl)hexahydropyrrolo[3,4-c]pyrrole-2(1H)-carboxylate α-(Trifluoromethyl)benzylalcohol (200 μL, 1.47 mmol) and potassium tert-butoxide (107.5 mg, 0.96 mmol) in anhydrous DMSO (1 mL) were reacted with the product from Example 19A as described in Example 19B to afford the title compound. MS (DCI/NH$_3$) m/z 465 (M+H)$^+$.

Example 21B (3aR,6aS)-2-(6-(2,2,2-trifluoro-1-phenylethoxy)pyrazin-2-yl)octahydropyrrolo[3,4-c]pyrrole The product from Example 21A was reacted with TFA in CH$_2$Cl$_2$ as described in Example 1I to afford the title compound as the TFA salt. $^1$H NMR (CD$_3$OD, 300 MHz) δ ppm 3.12-3.25 (m, 4H), 3.43-3.68 (m, 6H), 6.50 (q, J=7.0 Hz, 1H), 7.39-7.41 (m, 3H), 7.51 (s, 1H), 7.55-7.58 (m, 2H), 7.61 (s, 1H); MS (DCI/NH$_3$) m/z 365 (M+H)$^+$.

Example 22

(3aR,6aS)-2-(6-(benzyloxy)pyrazin-2-yl)octahydro-pyrrolo[3,4-c]pyrrole

Example 22A 2-(benzyloxy)-6-chloropyrazine

Benzylalcohol (500 µL, 7.83 mmol) and potassium tert-butoxide (222.4 mg, 1.82 mmol) in anhydrous DMSO (1 mL) were reacted with 2,6-dichloropyrazine (149.7 mg, 1.00 mmol) as described in Example 19B to afford the title compound. MS (DCI/NH$_3$) m/z 221 (M+H)$^+$.

Example 22B (3aR,6aS)-tert-butyl 5-(6-(benzyloxy)pyrazin-2-yl)hexahydropyrrolo[3,4-c]pyrrole-2(1H)-carboxylate The product from Example 22A (80.2 g, 0.36 mmol) was reacted with the product from Example 1C (129 mg, 0.61 mmol) and N,N-diisopropylethylamine (100 µL) in DMSO as described in Example 19A to afford the title compound. MS (DCI/NH$_3$) m/z 397 (M+H)$^+$.

Example 22C (3aR,6aS)-2-(6-(benzyloxy)pyrazin-2-yl)octahydro-pyrrolo[3,4-c]pyrrole The product from Example 22B was reacted with TFA in CH$_2$Cl$_2$ and processed as described in Example 8B to afford the title compound as the fumaric acid salt. $^1$H NMR (CD$_3$OD, 300 MHz) δ ppm 3.19-3.35 (m, 4H), 3.57-3.69 (m, 6H), 5.38 (s, 2H), 6.67 (s, 2H), 7.26-7.41 (m, 5H), 7.43 (s, 1H), 7.47 (s, 1H); MS (DCI/NH$_3$) m/z 297 (M+H)$^+$.

Example 23

(3aR,6aS)-2-(6-(4-fluorobenzyloxy)pyrazin-2-yl)octahydropyrrolo[3,4-c]pyrrole

Example 23A 2-chloro-6-(4-fluorobenzyloxy)pyrazine

4-Fluorobenzylalcohol (200 µL, 1.85 mmol) and potassium tert-butoxide (122.1 mg, 1.00 mmol) in anhydrous DMSO (1 mL) were reacted with 2,6-dichloropyrazine (156.8 mg, 1.05 mmol) as described in Example 19B to afford the title compound. MS (DCI/NH$_3$) m/z 239 (M+H)$^+$.

Example 23B (3aR,6aS)-tert-butyl 5-(6-(4-fluorobenzyloxy)pyrazin-2-yl)hexahydropyrrolo[3,4-c]pyrrole-2(1H)-carboxylate The product from Example 23A (127.9 mg, 0.54 mmol) was reacted with the product from Example 1C (147.5 mg, 0.69 mmol) and N,N-diisopropylethylamine (100 µL) in DMSO as described in Example 19A to afford the title compound. MS (DCI/NH$_3$) m/z 415 (M+H)$^+$.

Example 23C (3aR,6aS)-2-(6-(4-fluorobenzyloxy)pyrazin-2-yl)octahydropyrrolo[3,4-c]pyrrole The product from Example 23B was reacted with TFA in CH$_2$Cl$_2$ and processed as described in example 8B to afford the title compound as the fumaric acid salt. $^1$H NMR (CD$_3$OD, 300 MHz) δ ppm 3.20-3.35 (m, 4H), 3.57-3.69 (m, 6H), 5.35 (s, 2H), 6.67 (s, 2H), 7.05-7.11 (m, 2H), 7.44-7.48 (m, 4H); MS (DCI/NH$_3$) m/z 315 (M+H)$^+$; Anal. (C$_{12}$H$_{19}$FN$_4$O.1.05 C$_4$H$_4$O$_4$) C, H, N.

Example 24

N-(6-((3aR,6aS)-hexahydropyrrolo[3,4-c]pyrrol-2(1H)-yl)pyrazin-2-yl)-3-methylbenzamide Example 24A N-(6-chloropyrazin-2-yl)-3-methylbenzamide 2-Amino-6-chloropyrazine (496.0 mg, 3.83 mmol) was dissolved in pyridine (15 mL). 3-Methylbenzoyl chloride (760 µL, 5.77 mmol) was added to the reaction mixture. The reaction was heated to 100° C. for 16 h then concentrated under vacuum. The residue was partitioned between 1M K$_2$CO$_3$ (50 mL) and CH$_2$Cl$_2$ (4×50 mL). The organic extracts were combined, washed with and brine (50 mL), dried over Na$_2$SO$_4$, filtered and concentrated under vacuum. The residue was purified by silica gel chromatography (5% EtOAc in CH$_2$Cl$_2$, R$_f$=0.39) to afford the title compound as a white solid (919.0 mg, 97%). MS m/z 248 (M+H)$^+$.

Example 24B (3aR,6aS)-tert-butyl 5-(6-(3-methylbenzamido)pyrazin-2-yl)hexahydropyrrolo[3,4-c]pyrrole-2(1H)-carboxylate The product from Example 24A (130.5 mg, 0.53 mmol) was reacted with the product from Example 1C (149.6 mg, 0.70 mmol) and N,N-diisopropylethylamine (110 µL) in DMSO as described in Example 19A, except that the mixture was heated to 110° C. overnight, to afford the title compound. MS (DCI/NH$_3$) m/z 424 (M+H)$^+$.

Example 24C

N-(6-((3aR,6aS)-hexahydropyrrolo[3,4-c]pyrrol-2(1H)-yl)pyrazin-2-yl)-3-methylbenzamide The product from Example 24B (175.3 mg, 0.41 mmol) was reacted with TFA in CH$_2$Cl$_2$ as described in Example 11 to afford the title compound as the TFA salt. $^1$H NMR (CD$_3$OD, 300 MHz) δ ppm 2.44 (s, 3H), 3.22-3.28 (m, 4H), 3.59-3.69 (m, 6H), 7.38-7.42 (m, 2H), 7.72-7.77 (m, 3H), 8.74 (s, 1H); MS (DCI/NH$_3$) m/z 324 (M+H)$^+$.

Example 25

N-benzyl-5-((3aR,6aS)-hexahydropyrrolo[3,4-c]
pyrrol-2(1H)-yl)pyridin-3-amine

Example 25A

N-benzyl-5-bromopyridin-3-amine 3,5-Dibromopyridine (20.0 g, 84.4 mmol) and benzylamine (9.23 mL, 84.4 mmol) were dissolved in toluene (100 mL). $Pd_2(dba)_3$ (1.55 g, 1.69 mmol), BINAP (2.10 g, 3.38 mmol) and sodium tert-butoxide (12.2 g, 127 mmol) were added to the reaction mixture. The reaction was heated to 80° C. for 16 h, then allowed to cool to ambient temperature, diluted with ether (400 mL) and washed with brine (3×100 mL). The organic layer was dried over $MgSO_4$, filtered and concentrated under vacuum. The residue was purified by silica gel chromatography (25% EtOAc in hexanes) to afford the title compound as a slightly yellow solid (14.75 g, 66%). MS ($DCI/NH_3$) m/z 263 $(M+H)^+$.

Example 25B (3aR,6aS)-tert-butyl 5-(5-(benzylamino)pyridin-3-yl)
hexahydropyrrolo[3,4-c]pyrrole-2(1H)-carboxylate The product from Example 25A (201.7 mg, 0.77 mmol) was dissolved in toluene (7.7 mL). To the reaction mixture was added the product from Example 1C (204.6 mg, 0.96 mmol), $Pd_2(dba)_3$ (27.0 mg, 0.029 mmol), BINAP (60.7 mg, 0.097 mg) and sodium tert-butoxide (105.3 mg, 1.10 mmol). The reaction was heated to 90° C. overnight (18 h), then allowed to cool to ambient temperature, diluted with water (100 mL) and extracted with $CH_2Cl_2$ (3×50 mL). The organic extracts were combined and washed with brine (50 mL), dried over $Na_2SO_4$, filtered and concentrated under vacuum. The residue was purified by preparative HPLC on a Waters Nova-Pak® HR C18 6 μm 60 Å Prep-Pak® cartridge column (40 mm×100 mm) using a gradient of 10% to 100% acetonitrile in 10 mM aqueous ammonium acetate over 12 min at a flow rate of 70 mL/min to provide the title compound MS ($DCI/NH_3$) m/z 395 $(M+H)^+$.

Example 25C

N-benzyl-5-((3aR,6aS)-hexahydropyrrolo[3,4-c]
pyrrol-2(1H)-yl)pyridin-3-amine

The product from Example 25B (86.6 mg, 0.41 mmol) was reacted with TFA in $CH_2Cl_2$ as described in Example 1I to afford the title compound as the TFA salt. $^1H$ NMR ($CD_3OD$, 300 MHz) δ ppm 3.21-3.28 (m, 4H), 3.38-3.51 (m, 4H), 3.57-3.63 (m, 2H), 4.43 (s, 2H), 6.66 (t, J=2.2 Hz, 1H), 7.24-7.40 (m, 7H); MS ($DCI/NH_3$) m/z 295 $(M+H)^+$.

Example 26

(3aR,6aS)-2-(5-styrylpyridin-3-yl)octahydropyrrolo
[3,4-c]pyrrole

Example 26A (3aR,6aS)-tert-butyl 5-(5-bromopyridin-3-yl)hexahydropyrrolo[3,4-c]pyrrole-2(1H)-carboxylate The product from Example 1C (1.01 g, 4.76 mmol) and 3,5-dibromopyridine (1.22 g, 5.15 mmol) were dissolved in toluene (20 mL). $Pd_2(dba)_3$ (86.8 mg, 0.095 mmol), BINAP (175.0 mg, 0.28 mmol) and sodium tert-butoxide (665.4 mg, 1.460 mmol) were added to the reaction mixture. The reaction was heated to 80° C. for 22 h, then allowed to cool to ambient temperature, diluted with water (100 mL) and extracted with $CH_2Cl_2$ (3×100 mL). The organic extracts were combined and washed with brine (50 mL), dried over $MgSO_4$, filtered, and concentrated under vacuum. The residue was purified by silica gel chromatography (EtOAc, $R^r$=0.33) to afford the title compound as a white solid (1.17 g, 67%). MS ($DCI/NH_3$) m/z 370 $(M+H)^+$.

Example 26B (3aR,6aS)-tert-butyl 5-(5-styrylpyridin-3-yl)hexahydropyrrolo[3,4-c]pyrrole-2(1H)-carboxylate The product from Example 26A (762.8 mg, 2.07 mmol) and styrene (460 μL, 4.00 mmol) were dissolved in acetonitrile (6 mL) and triethylamine (5 mL). $Pd(OAc)_2$ (43.4 mg, 0.19 mmol) and $P(o-tolyl)_3$ (256.7 mg, 0.84 mmol) were added to the reaction mixture. The reaction was refluxed overnight (20 h), then allowed to cool to ambient temperature, diluted with saturated $NaHCO_3$ (aq) (100 mL) and extracted with $CH_2Cl_2$ (3×100 mL). The organic extracts were combined and washed with brine (100 mL), dried over $MgSO_4$, filtered and concentrated under vacuum. The residue was purified by silica gel chromatography (40% acetone in $CH_2Cl_2$, $R_f$=0.30) to afford the title compound as a white solid (773.2 mg, 95%). MS ($DCI/NH_3$) m/z 392 $(M+H)^+$.

Example 26C (3aR,6aS)-2-(5-styrylpyridin-3-yl)octahydropyrrolo
[3,4-c]pyrrole The product from Example 26B was reacted with TFA in $CH_2Cl_2$ and processed as described in Example 8B to afford the title compound as the fumaric acid salt. $^1H$ NMR ($CD_3OD$, 300 MHz) δ ppm 3.20-3.35 (m, 4H), 3.39-3.45 (m, 2H), 3.53-3.64 (m, 4H), 6.66 (s, 2H), 7.15 (d, J=16.3 Hz, 1H), 7.25-7.39 (m, 5H), 7.57-7.59 (m, 2H), 7.91 (d, J=2.7 Hz, 1H), 8.11 (d, J=1.7 Hz, 1H); MS ($DCI/NH_3$) m/z 292 $(M+H)^+$.

Example 27

(3aR,6aS)-2-(5-(4-fluorostyryl)pyridin-3-yl)octahydropyrrolo[3,4-c]pyrrole

Example 27A (3aR,6aS)-tert-butyl 5-(5-(4-fluorostyryl)pyridin-3-yl)hexahydropyrrolo[3,4-c]pyrrole-2(1H)-carboxylate The product from Example 26A (369.1 mg, 1.00 mmol) and 4-fluorostyrene (240 μL, 2.00 mmol) in acetonitrile (3 mL) and triethylamine (2.5 mL) were reacted as described in Example 26B using $Pd(OAc)_2$ (23.8 mg, 0.11 mmol) and $P(o-tolyl)_3$ (121.2 mg, 0.40 mmol) to afford the title compound. MS ($DCI/NH_3$) m/z 410 $(M+H)^+$.

Example 27B (3aR,6aS)-2-(5-(4-fluorostyryl)pyridin-3-yl)octahydropyrrolo[3,4-c]pyrrole The product from Example 27A was reacted with TFA in $CH_2Cl_2$ and processed as described in Example 8B to afford the title compound as the fumaric acid salt. $^1$H NMR (CD$_3$OD, 300 MHz) δ ppm 3.15-3.27 (m, 4H), 3.39-3.45 (m, 2H), 3.50-3.59 (m, 4H), 6.65 (s, 1H), 7.06-7.13 (m, 3H), 7.26-7.32 (m, 2H), 7.58-7.63 (m, 2H), 7.90 (d, J=2.7 Hz, 1H), 8.09 (d, J=1.4 Hz, 1H); MS (DCI/NH$_3$) m/z 310 (M+H)$^+$.

Example 28

(3aR,6aS)-2-(6-styrylpyrazin-2-yl)octahydropyrrolo[3,4-c]pyrrole

Example 28A (3aR,6aS)-tert-butyl 5-(6-styrylpyrazin-2-yl)hexahydropyrrolo[3,4-c]pyrrole-2(1H)-carboxylate The product from Example 19A (473.1 mg, 1.46 mmol) and styrene (350 μL, 3.04 mmol) in acetonitrile (6 mL) and triethylamine (5 mL) were reacted as described in Example 26B using Pd(OAc)$_2$ (36.3 mg, 0.16 mmol) and P(o-tolyl)$_3$ (193.9 mg, 0.64 mmol) to afford the title compound. MS (DCI/NH$_3$) m/z 393 (M+H)$^+$.

Example 28B (3aR,6aS)-2-(6-styrylpyrazin-2-yl)octahydropyrrolo[3,4-c]pyrrole

The product from Example 28A was reacted with TFA in CH$_2$Cl$_2$ and processed as described in Example 8B to afford the title compound as the fumaric acid salt. $^1$H NMR (DMSO-d$_6$, 300 MHz) δ ppm 3.24-3.30 (m, 4H), 3.59-3.66 (m, 2H), 3.73-3.75 (m, 4H), 6.68 (s, 2H), 7.14 (d, J=15.9 Hz, 1H), 7.28-7.40 (m, 3H), 7.58-7.61 (m, 2H), 7.73 (d, J=15.9 Hz, 1H), 7.83 (s, 1H), 7.90 (s, 1H); MS (DCI/NH$_3$) m/z 293 (M+H)$^+$.

Example 29

(3aR,6aS)-2-(5-phenethylpyridin-3-yl)octahydropyrrolo[3,4-c]pyrrole

Example 29A (3aR,6aS)-tert-butyl 5-(5-phenethylpyridin-3-yl)hexahydropyrrolo[3,4-c]pyrrole-2(1H)-carboxylate The product from 26B (200 mg, 0.51 mmol) was dissolved in MeOH (10 mL). Pd/C (10 wt %, 20 mg) was added to the reaction mixture and an atmosphere of hydrogen gas was introduced via balloon. The reaction was stirred at ambient temperature for 16 h. The reaction was filtered and concentrated under vacuum. The residue was purified by preparative HPLC on a Waters Nova-Pak® HR C18 6 μm 60 Å Prep-Pak® cartridge column (40 mm×100 mm) using a gradient of 10% to 100% acetonitrile in 10 mM aqueous ammonium acetate over 12 min at a flow rate of 70 mL/min to provide the title compound MS (DCI/NH$_3$) m/z 394 (M+H)$^+$.

Example 29B (3aR,6aS)-2-(5-phenethylpyridin-3-yl)octahydropyrrolo[3,4-c]pyrrole

The product from Example 29A was reacted with TFA in CH$_2$Cl$_2$ and processed as described in Example 8B to afford the title compound as the fumaric acid salt. $^1$H NMR (CD$_3$OD, 300 MHz) δ ppm 2.89-2.93 (m, 4H), 3.10-3.25 (m, 4H), 3.38-3.42 (m, 2H), 3.50-3.56 (m, 4H), 6.65 (s, 1H), 6.89-6.90 (m, 1H), 7.13-7.17 (m, 3H), 7.21-7.26 (m, 2H), 7.70 (d, J=1.7 Hz, 1H), 7.81 (d, J=2.7 Hz, 1H); MS (DCI/NH$_3$) m/z 294 (M+H)$^+$; Anal. (C$_{19}$H$_{23}$N$_3$.0.5 C$_4$H$_4$O$_4$) C, H, N.

Example 30

(3aR,6aS)-2-(5-(4-fluorophenethyl)pyridin-3-yl)octahydropyrrolo[3,4-c]pyrrole

Example 30A (3aR,6aS)-tert-butyl 5-(5-(4-fluorophenethyl)pyridin-3-yl)hexahydropyrrolo[3,4-c]pyrrole-2(1H)-carboxylate The product from Example 27A (169.8 mg, 0.41 mmol) was reacted with Pd/C and hydrogen in MeOH as described in Example 29A to provide the title compound MS (DCI/NH$_3$) m/z 412 (M+H)$^+$.

Example 30B (3aR,6aS)-2-(5-(4-fluorophenethyl)pyridin-3-yl)octahydropyrrolo[3,4-c]pyrrole The product from Example 30A was reacted with TFA in CH$_2$Cl$_2$ and processed as described in Example 8B to afford the title compound as the fumaric acid salt. $^1$H NMR (CD$_3$OD, 300 MHz) δ ppm 2.89-2.93 (m, 4H), 3.13-3.22 (m, 4H), 3.28-3.34 (m, 2H), 3.40-3.44 (m, 2H), 3.52-3.57 (m, 2H), 6.65 (s, 2H), 6.90-7.00 (m, 3H), 7.11-7.17 (m, 2H) 7.70 (d, J=1.7 Hz, 1H), 7.82 (d, J=2.7 Hz, 1H); MS (DCI/NH$_3$) m/z 312 (M+H)$^+$.

Example 31

5-((3aR,6aS)-hexahydropyrrolo[3,4-c]pyrrol-2(1H)-yl)-N-(2-methylbenzyl)nicotinamide Example 31A 5-bromo-N-(2-methylbenzyl)nicotinamide Prepared from 5-bromonicotinic acid and 2-methylbenzylamine using procedures as described in Example 1H. MS (APCI) m/z 305, 307 (M+H)$^+$.

Example 31B (3aR,6aS)-tert-butyl 5-(5-(2-methylbenzylcarbamoyl)pyridin-3-yl)hexahydropyrrolo[3,4-c]pyrrole-2(1H)-carboxylate The product from Example 1C (80 mg, 0.38 mmol), the product from Example 31A (155 mg, 0.51 mmol), (R)-(+)-2,2'-bis(diphenylphosphino)-1,1'-binaphthyl (34 mg, 0.034 mmol), tris(dibenzylideneacetone)dipalladium(0) (10.4 mg, 0.011 mmol), and sodium tert-butoxide (54.2 mg, 0.054 mmol) were combined with toluene (5 mL). The suspension was evacuated and purged with nitrogen. The mixture was heated at 95° C. under nitrogen for 4 h. The residue was partitioned between saturated sodium bicarbonate solution$_{(aq)}$ (100 mL) and EtOAc (2×50 mL). The combined organic extract was washed with brine (100 mL), dried ($Na_2SO_4$) and concentrated under vacuum. The residue was purified by flash chromatography (eluted with EtOAc) on silica to provide the title compound (150 mg, 91%). MS (APCI) m/z 437 (M+H)$^+$.

Example 31C 5-3aR,6aS)-hexahydropyrrolo[3,4-c]pyrrol-2(1H)-yl-N-(2-methylbenzyl)nicotinamide The product from Example 31B (150 mg, 0.34 mmol) was dissolved in $CH_2Cl_2$ (5 mL). TFA (10 mL) was added. The reaction mixture was stirred at ambient temperature for 1 h and then concentrated under vacuum. The residue was taken up with 1.0 M $Na_2CO_{3(aq)}$ (100 mL) and extracted with $CHCl_3$-isopropanol (4:1, 2×50 mL). The combined organic extract was dried ($Na_2SO_4$) and concentrated under vacuum. The residue was purified on a silica flash chromatography column and eluted with $NH_4OH$—$CH_3CN$ (10:90 to 20:80). The product fractions were combined and concentrated to dryness. The residue was dissolved in a minimal amount of methanol. A solution of fumaric acid (80 mg, 0.69 mmol) in ether-methanol (10:1, 8.0 mL) was slowly added. After stirring for 1 h, the precipitate was collected by filtration, rinsed with ether, and dried to afford the title compound as the fumaric acid salt (129 mg, 86%). $^1$H NMR (300 MHz, $CD_3OD$) δ ppm 2.37 (s, 3H), 3.20-3.28 (m, 3H), 3.38-3.73 (m, 7H), 4.59 (s, 2H), 6.70 (s, 2H; $C_4H_4O_4$), 7.11-7.21 (m, 3H), 7.24-7.32 (m, 1H), 7.50-7.57 (m, 1H), 8.14 (d, J=2.7 Hz, 1H), 8.37 (d, J=1.7 Hz, 1H); MS (ESI) m/z 337 (M+H)$^+$; Anal. ($C_{20}H_{24}N_4O.1.3C_4H_4.0.5H_2O$)

Example 32

5-((3aS,6aS)-hexahydropyrrolo[3,4-b]pyrrol-1(2H)-yl)-N-(2-methylbenzyl)nicotinamide

Example 32A (3aS,6aS)-tert-butyl 1-(5-(2-methylbenzylcarbamoyl)pyridin-3-yl)hexahydropyrrolo[3,4-b]pyrrole-5(1H)-carboxylate Prepared from (3aS,6aS)-tert-butyl hexahydropyrrolo[3,4-b]pyrrole-5(1H)-carboxylate (prepared as described in WO2001081347) and the product from Example 31A using the procedure as described in Example 31B. MS (APCI) m/z 437 (M+H)$^+$.

Example 32B 5-((3aS,6aS)-hexahydropyrrolo[3,4-b]pyrrol-1(2H)-yl-N-(2-methylbenzyl)nicotinamide The product from Example 32A was processed as described in Example 31C to provide the title compound as the fumaric acid salt. $^1$H NMR (300 MHz, $CD_3OD$) δ ppm 1.95-2.11 (m, 1H), 2.24-2.37 (m, 1H), 2.38 (s, 3H), 3.27-3.38 (m, 2H), 3.40-3.63 (m, 4H), 3.68-3.80 (m, 1H), 4.48 (ddd, J=7.5, 5.5, 2.0 Hz, 1H), 4.59 (s, 2H), 6.69 (s, 2H; $C_4H_4O_4$), 7.11-7.21 (m, 3H), 7.24-7.34 (m, 1H), 7.45 (dd, J=2.9, 1.9 Hz, 1H), 8.10 (d, J=2.7 Hz, 1H), 8.39 (d, J=2.0 Hz, 1H); MS (ESI) m/z 337 (M+H)$^+$.

Example 33

5-((3aR,6aS)-hexahydropyrrolo[3,4-c]pyrrol-2(1H)-yl)-N-(2-(trifluoromethyl)benzyl)nicotinamide

Example 33A (3aR,6aS)-tert-butyl 5-(5-(ethoxycarbonyl)pyridin-3-yl)hexahydropyrrolo[3,4-c]pyrrole-2(1H)-carboxylate A suspension of the product from Example 1C (2.00 g, 9.42 mmol), ethyl 5-bromonicotinate (2.80 g, 12.0 mmol), tris(dibenzylideneacetone)dipalladium(0) (259 mg, 0.283 mmol), 4,5-bis(diphenylphosphino)-9,9-dimethylxanthene (491 mg, 0.848 mmol) and cesium carbonate (4.91 g, 15.1 mmol) in anhydrous dioxane (50 mL) were heated at 90° C. for 72 hours. The reaction mixture was cooled and filtered through a glass frit. The filtrate was concentrated and the residue was purified by silica gel chromatography (eluted with 50% EtOAc in hexane) to afford the title compound (3.2 g, 94%). MS (APCI) m/z 362 (M+H)$^+$.

Example 33B 5-((3aR,6aS)-5-(tert-butoxycarbonyl)hexahydropyrrolo[3,4-c]pyrrol-2(1H)-yl)nicotinic Acid The product from Example 33A (3.20 g, 8.90 mmol) was dissolved in a solvent mixture of ethanol (40 mL) and water (20 mL). Sodium hydroxide (2.0 M, 13 mL) was added, and the reaction mixture was stirred at ambient temperature for 1 hour. The mixture was then diluted with ethyl acetate (100 mL) and partitioned between ethyl acetate (250 mL) and water (30 mL). The aqueous layer was acidified to pH 4 and repartitioned between dichloromethane (200 mL) and water (250 mL). The organic layer was dried ($Na_2SO_4$) and concentrated under vacuum to afford the title compound (3.0 g, 102%). $^1$H NMR (400 MHz, $CD_3OD$) δ ppm 1.45 (s, 9H), 3.06-3.14 (br s, 2H), 3.27-3.34 (m, 4H), 3.61 (dd, J=10.0, 7.5 Hz, 2H), 3.64-3.71 (m, 2H), 7.57 (dd, J=2.8, 1.8 Hz, 1H), 8.04 (d, J=1.5 Hz, 1H), 8.39 (s, 1H). MS (APCI) m/z 334 (M+H)$^+$.

Example 33C (3aR,6aS)-tert-butyl 5-(5-(2-(trifluoromethyl)benzylcarbamoyl)pyridin-3-yl)hexahydropyrrolo[3,4-c]pyrrole-2(1H)-carboxylate A suspension of the product from Example 33B (52.5 mg, 0.16 mmol), 2-trifluoromethylbenzylamine (33.3 mg, 0.19 mmol), 1-hydroxybenzotriazole (30.1 mg, 0.20 mmol), 4-dimethylaminopyridine (4 mg, 0.03 mmol) and N-(3-dimethylaminopropyl)-N'-ethylcarbodiimide hydrochloride (34.3 mg, 0.24 mmol) in pyridine (7.0 mL) were stirred at 33° C. for 18 h. The reaction mixture was filtered through a glass microfiber frit and rinsed with methanol. The filtrate was concentrated and the residue was purified by silica gel chromatography (EtOAc, $R_f$=0.2) to afford the title compound. MS (APCI) m/z 491 (M+H)$^+$.

Example 33D 5-((3aR,6aS)-hexahydropyrrolo[3,4-c]pyrrol-2(1H)-yl)-N-(2-(trifluoromethyl)benzyl)nicotinamide The product from Example 33C was processed as described in Example 3° C. to provide the title compound as the fumaric acid salt. $^1$H NMR (300 MHz, CD$_3$OD) δ ppm 2.37 (s, 3H), 3.20-3.28 (m, 3H), 3.38-3.73 (m, 7H), 4.59 (s, 2), 6.70 (s, 2H; C$_4$H$_4$O$_4$), 7.11-7.21 (m, 3H), 7.24-7.32 (m, 1H), 7.50-7.57 (m, 1H), 8.14 (d, J=2.7 Hz, 1H), 8.37 (d, J=1.7 Hz, 1H); MS (ESI) m/z 337 (M+H)$^+$.

Example 34

N-(2-fluorophenethyl)-5-((3aR,6aS)-hexahydropyrrolo[3,4-c]pyrrol-2(1H)-yl)nicotinamide Example 34A (3aR,6aS)-tert-butyl 5-(5-(2-fluorophenethylcarbamoyl)pyridin-3-yl)hexahydropyrrolo[3,4-c]pyrrole-2(1H)-carboxylate The product from Example 33B and 2-(2-fluorophenyl)ethanamine were processed as described in Example 33C to provide the title compound. MS (ESI) m/z 455 (M+H)$^+$.

Example 34B

N-(2-fluorophenethyl)-5-((3aR,6aS)-hexahydropyrrolo[3,4-c]pyrrol-2(1H)-yl)nicotinamide The product from Example 34A was processed as described in Example 11 to provide the title compound as the TFA salt. $^1$H NMR (300 MHz, DMSO-d$_6$) δ ppm 2.89 (t, J=7.1 Hz, 2H), 3.04-3.24 (m, 4H), 3.33-3.48 (m, 9H), 7.08-7.21 (m, 2H), 7.22-7.36 (m, 2H), 7.38-7.45 (m, 1H), 8.14 (d, J=3.1 Hz, 1H), 8.33 (d, J=1.7 Hz, 1H), 8.74 (t, J=5.8 Hz, 1H), 8.82 (br s, 2H; TFA); MS (ESI) m/z 355 (M+H)$^+$.

Example 35

N-(3,5-dimethoxyphenyl)-5-((3aR,6aS)-hexahydropyrrolo[3,4-c]pyrrol-2(1H)-yl)nicotinamide Example 35A (3aR,6aS)-tert-butyl 5-(5-(3,5-dimethoxyphenylcarbamoyl)pyridin-3-yl)hexahydropyrrolo[3,4-c]pyrrole-2(1H)-carboxylate The product from Example 33B and 3,5-dimethoxyaniline were processed as described in Example 33C to provide the title compound. MS (APCI) m/z 469 (M+H)$^+$.

Example 35B

N-(3,5-dimethoxyphenyl)-5-((3aR,6aS)-hexahydropyrrolo[3,4-c]pyrrol-2(1H)-yl)nicotinamide The product from Example 35A was processed as described in Example 31C to provide the title compound as the fumaric acid salt. $^1$H NMR (300 MHz, CD$_3$OD) δ ppm 3.20-3.29 (m, 4H), 3.42-3.68 (m, 6H), 3.79 (s, 6H), 6.32 (t, J=1.9 Hz, 1H), 6.66 (s, 2H; C$_4$H$_4$O$_4$), 6.97 (d, J=2.0 Hz, 2H), 7.55-7.60 (m, 1H), 8.17 (d, J=2.7 Hz, 1H), 8.43 (s, 1H); MS (APCI) m/z 369 (M+H)$^+$; Anal. (C$_{20}$H$_{24}$N$_4$O$_3$·1.5C$_4$H$_4$O$_4$) C, H, N.

Example 36

5-((3aR,6aS)-hexahydropyrrolo[3,4-c]pyrrol-2(1H)-yl)-N-(2-methoxybenzyl)nicotinamide Example 36A (3aR,6aS)-tert-butyl 5-(5-(2-methoxybenzylcarbamoyl)pyridin-3-yl)hexahydropyrrolo[3,4-c]pyrrole-2(1H)-carboxylate The product from Example 33B and 2-methoxybenzylamine were processed as described in Example 33C to provide the title compound. MS (APCI) m/z 453 (M+H)$^+$.

Example 36B 5-((3aR,6aS)-hexahydropyrrolo[3,4-c]pyrrol-2(1H)-yl)-N-(2-methoxybenzyl)nicotinamide The product from Example 36A was processed as described in Example 31C to provide the title compound as the fumaric acid salt. $^1$H NMR (300 MHz, CD$_3$OD) δ ppm 3.13-3.35 (m, 4H), 3.40-3.66 (m, 6H), 3.87 (s, 3H), 4.58 (s, 2H), 6.66 (s, 2H; C$_4$H$_4$O$_4$), 6.90 (td, J=7.5, 1.0 Hz, 1H), 6.95-7.01 (m, 1H), 7.16-7.34 (m, 2H), 7.51 (dd, J=2.9, 1.9 Hz, 1H), 8.13 (d, J=2.7 Hz, 1H), 8.35 (d, J=2.0 Hz, 1H). MS (ESI) m/z 353 (M+H)$^+$.

Example 37

5-((3aR,6aS)-hexahydropyrrolo[3,4-c]pyrrol-2(1H)-yl)-N—((R)-1-phenylethyl)nicotinamide Example 37A (3aR,6aS)-tert-butyl 5-(5-((R)-1-phenylethylcarbamoyl)pyridin-3-yl)hexahydropyrrolo[3,4-c]pyrrole-2(1H)-carboxylate The product from Example 33B and (R)-1-phenylethanamine were processed as described in Example 33C to provide the title compound. MS (APCI) m/z 437 (M+H)$^+$.

Example 37B 5-((3aR,6aS)-hexahydropyrrolo[3,4-c]pyrrol-2(1H-yl)-N—((R)-1-phenylethyl)nicotinamide The product from Example 37A was processed as described in Example 31C to provide the title compound as the fumaric acid salt. $^1$H NMR (300 MHz, CD$_3$OD) δ ppm 1.57 (d, J=6.8 Hz, 3H), 3.17-3.28 (m, 4H), 3.39-3.66 (m, 6H), 5.24 (q, J=7.0 Hz, 1H), 6.66 (s, 2H; C$_4$H$_4$O$_4$), 7.20-7.27 (m, 1H), 7.29-7.42 (m, 4H), 7.48 (dd, J=2.9, 1.9 Hz, 1H), 8.12 (d, J=2.7 Hz, 1H), 8.36 (d, J=1.7 Hz, 1H); MS (ESI) m/z 337

(M+H)+; [α]D=+11.7° (25° C., c=0.105); Anal. (C$_{20}$H$_{24}$N$_4$O.1.1 C$_4$H$_4$O$_4$.0.2H$_2$O) C, H, N.

Example 38

5-((3aR,6aS)-hexahydropyrrolo[3,4-c]pyrrol-2(1H)-yl)-N—((S)-1-phenylethyl)nicotinamide

Example 38A (3aR,6aS)-tert-butyl 5-(5-((S)-1-phenylethylcarbamoyl)pyridin-3-yl)hexahydropyrrolo[3,4-c]pyrrole-2(1H)-carboxylate The product from Example 33B and (S)-1-phenylethanamine were processed as described in Example 33C to provide the title compound. MS (APCI) m/z 437 (M+H)+.

Example 38B 5-((3aR,6aS)-hexahydropyrrolo[3,4-c]pyrrol-2(1H)-yl)-N—((S)-1-phenylethyl)nicotinamide The product from Example 38A was processed as described in Example 31C to provide the title compound as the fumaric acid salt. $^1$H NMR (300 MHz, CD$_3$OD) δ ppm 1.57 (d, J=6.8 Hz, 3H), 3.16-3.28 (m, 4H), 3.39-3.65 (m, 6H), 5.24 (q, J=7.0 Hz, 1H), 6.66 (s, 2H; C$_4$H$_4$O$_4$), 7.20-7.27 (m, 1H), 7.29-7.42 (m, 4H), 7.48 (dd, J=2.9, 1.9 Hz, 1H), 8.12 (d, J=2.7 Hz, 1H), 8.36 (d, J=1.7 Hz, 1H); MS (ESI) m/z 337 (M+H)+; [α]D=-11.2° (25° C., c=0.10); Anal. (C$_{20}$H$_{24}$N$_4$O.1.5 C$_4$H$_4$O$_4$.0.1H$_2$O) C, H, N.

Example 39

5-((3aR,6aS)-hexahydropyrrolo[3,4-c]pyrrol-2(1H)-yl)-N-m-tolylnicotinamide

Example 39A (3aR,6aS)-tert-butyl 5-(5-(m-tolylcarbamoyl)pyridin-3-yl)hexahydropyrrolo[3,4-c]pyrrole-2(1H)-carboxylate The product from Example 33B and m-toluidine were processed as described in Example 33C to provide the title compound. MS (APCI) m/z 423 (M+H)+.

Example 39B 5-((3aR,6aS)-hexahydropyrrolo[3,4-c]pyrrol-2(1H)-yl)-N-m-tolylnicotinamide The product from Example 39A was processed as described in Example 31C to provide the title compound as the fumaric acid salt. $^1$H NMR (300 MHz, CD$_3$OD) δ ppm 2.36 (s, 3H), 3.21-3.35 (m, 4H), 3.43-3.53 (m, 2H), 3.54-3.68 (m, 4H), 6.69 (s, 2H; C$_4$H$_4$O$_4$), 6.95-7.03 (m, 1H), 7.25 (t, J=7.8 Hz, 1H), 7.45-7.53 (m, 2H), 7.59 (dd, J=2.9, 1.9 Hz, 1H), 8.18 (d, J=2.7 Hz, 1H), 8.45 (d, J=2.0 Hz, 1H); MS (DCI/NH$_3$) m/z 323 (M+H)+; Anal. (C$_{20}$H$_{24}$N$_4$O 0.95 C$_4$H$_4$O$_4$) C, H, N.

Example 40

N-(3,5-dimethylphenyl-5-((3aR,6aS)-hexahydropyrrolo[3,4-c]pyrrol-2(1H)-yl)nicotinamide

Example 40A (3aR,6aS)-tert-butyl 5-(5-(3,5-dimethylphenylcarbamoyl)pyridin-3-yl)hexahydropyrrolo[3,4-c]pyrrole-2(1H)-carboxylate The product from Example 33B and 3,5-dimethylaniline were processed as described in Example 33C to provide the title compound. MS (APCI) m/z 337 (M+H)+.

Example 40B

N-(3,5-dimethylphenyl)-5-((3aR,6aS)-hexahydropyrrolo[3,4-c]pyrrol-2(1H)-yl)nicotinamide The product from Example 40A was processed as described in Example 31C to provide the title compound as the fumaric acid salt. $^1$H NMR (300 MHz, CD$_3$OD) δ ppm 2.31 (s, 6H), 3.22-3.36 (m, 4H), 3.44-3.69 (m, 6H), 6.69 (s, 2H; C$_4$H$_4$O$_4$), 6.83 (s, 1H), 7.31 (s, 2H), 7.58 (dd, J=2.7, 2.0 Hz, 1H), 8.17 (d, J=3.1 Hz, 1H), 8.44 (d, J=1.7 Hz, 1H); MS (DCI/NH$_3$) m/z 337 (M+H)+; Anal. (C$_{20}$H$_{24}$N$_4$O.1.5 C$_4$H$_4$O$_4$) C, H, N.

Example 41

5-((3aR,6aS)-hexahydropyrrolo[3,4-c]pyrrol-2(1H)-yl)-N-(2-(thiophen-2-yl)ethyl)nicotinamide

Example 41A (3aR,6aS)-tert-butyl 5-(5-(2-(thiophen-2-yl)ethylcarbamoyl)pyridin-3-yl)hexahydropyrrolo[3,4-c]pyrrole-2(1H)-carboxylate The product from Example 33B and thiophene-2-ethylamine were processed as described in Example 33C to provide the title compound. MS (APCI) m/z 443 (M+H)+.

Example 41B 5-((3aR,6aS)-hexahydropyrrolo[3,4-c]pyrrol-2(1H)-yl)-N-(2-(thiophen-2-yl)ethyl)nicotinamide The product from Example 41A was processed as described in Example 31C to provide the title compound as the fumaric acid salt. $^1$H NMR (300 MHz, CD$_3$OD) δ ppm 3.15 (t, J=7.0 Hz, 2H), 3.20-3.35 (m, 4H), 3.40-3.67 (m, 8H), 6.69 (s, 2H; C$_4$H$_4$O$_4$), 6.87-6.91 (m, 1H), 6.91-6.96 (m, 1H), 7.21 (dd, J=4.9, 1.2 Hz, 1H), 7.47 (dd, J=2.7, 1.7 Hz, 1H), 8.13 (d, J=3.1 Hz, 1H), 8.29 (d, J=1.7 Hz, 1H); MS (ESI) m/z 343 (M+H)⁺; Anal. (C₁₈H₂₂N₄OS. 1.55 C₄H₄O₄) C, H, N.

Example 42

N-(3,5-difluorophenyl)-5-((3aR,6aS)-hexahydropyrrolo[3,4-c]pyrrol-2(1H)-yl)nicotinamide Example 42A (3aR,6aS)-tert-butyl 5-(5-(3,5-difluorophenylcarbamoyl)pyridin-3-yl)hexahydropyrrolo[3,4-c]pyrrole-2(1H)-carboxylate The product from Example 33B and 3,5-difluoroaniline were processed as described in Example 33C to provide the title compound. MS (APCI) m/z 445 (M+H)⁺.

Example 42B

N-(3,5-difluorophenyl)-5-((3aR,6aS)-hexahydropyrrolo[3,4-c]pyrrol-2(1H)-yl)nicotinamide The product from Example 42A was processed as described in Example 31C to provide the title compound as the fumaric acid salt. ¹H NMR (300 MHz, CD₃OD) δ ppm 3.23-3.26 (m, 1H), 3.28-3.35 (m, 3H), 3.44-3.68 (m, 6H), 6.68 (s, 2H; C₄H₄O₄), 6.75 (tt, J=9.2, 2.4 Hz, 1H), 7.36-7.50 (m, 2H), 7.59 (dd, J=2.9, 1.9 Hz, 1H), 8.19 (d, J=2.7 Hz, 1H), 8.45 (d, J=1.7 Hz, 1H), 8.29 (d, J=1.7 Hz, 1H); MS (DCI/NH₃) m/z 345 (M+H)⁺.

Example 43

N-(2,3-dihydro-1H-inden-1-yl)-5-((3aR,6aS)-hexahydropyrrolo[3,4-c]pyrrol-2(1H)-yl)nicotinamide Example 43A (3aR,6aS)-tert-butyl 5-(5-(2,3-dihydro-1H-inden-1-ylcarbamoyl)pyridin-3-yl)hexahydropyrrolo[3,4-c]pyrrole-2(1H)-carboxylate The product from Example 33B and 1-aminoindane were processed as described in Example 33C to provide the title compound. MS (APCI) m/z 449 (M+H)⁺.

Example 43B

N-(2,3-dihydro-1H-inden-1-yl)-5-((3aR,6aS)-hexahydropyrrolo[3,4-c]pyrrol-2(1H)-yl)nicotinamide The product from Example 43A was processed as described in Example 31C to provide the title compound as the fumaric acid salt. ¹H NMR (300 MHz, CD₃OD) δ ppm 1.93-2.12 (m, 1H), 2.52-2.66 (m, 1H), 2.85-2.99 (m, 1H), 3.01-3.13 (m, 1H), 3.20-3.35 (m, 4H), 3.41-3.66 (m, 6H), 5.65 (t, J=7.8 Hz, 1H), 6.67 (s, 2H; C₄H₄O₄), 7.15-7.32 (m, 4H), 7.55 (dd, J=2.9, 1.9 Hz, 1H), 8.13 (d, J=3.1 Hz, 1H), 8.37 (d, J=2.0 Hz, 1H); MS (ESI) m/z 349 (M+H)⁺.

Example 44

5-((3aR,6aS)-hexahydropyrrolo[3,4-c]pyrrol-2(1H)-yl)-N-(3-isopropoxyphenyl)nicotinamide Example 44A (3aR,6aS)-tert-butyl 5-(5-(3-isopropoxyphenylcarbamoyl)pyridin-3-yl)hexahydropyrrolo[3,4-c]pyrrole-2(1H)-carboxylate The product from Example 33B and 3-isopropoxyaniline were processed as described in Example 33C to provide the title compound. MS (APCI) m/z 467 (M+H)⁺.

Example 44B 5-((3aR,6aS)-hexahydropyrrolo[3,4-c]pyrrol-2(1H)-yl)-N-(3-isopropoxyphenyl)nicotinamide The product from Example 44A was processed as described in Example 31C to provide the title compound as the fumaric acid salt. ¹H NMR (300 MHz, CD₃OD) δ ppm 1.33 (d, J=6.1 Hz, 6H), 3.19-3.37 (m, 4H), 3.42-3.69 (m, 6H), 4.60 (hept, J=6.1 Hz, 1H), 6.66 (s, 2H; C₄H₄O₄), 6.72 (td, J=4.6, 2.4 Hz, 1H), 7.16-7.29 (m, 2H), 7.38 (t, J=1.9 Hz, 1H), 7.58 (dd, J=2.7, 2.0 Hz, 1H), 8.17 (d, J=2.7 Hz, 1H), 8.44 (d, J=1.7 Hz, 1H); MS (ESI) m/z 367 (M+H)⁺; Anal. (C₂₁H₂₆N₄O₂.1.1 C₄H₄O₄.0.1H₂O)C, H, N.

Example 45

5-((3aR,6aS)-hexahydropyrrolo[3,4-c]pyrrol-2(1H)-yl-N-(3-iodophenyl)nicotinamide Example 45A (3aR,6aS)-tert-butyl 5-(5-(3-iodophenylcarbamoyl)pyridin-3-yl)hexahydropyrrolo[3,4-c]pyrrole-2(1H)-carboxylate The product from Example 33B and 3-iodoaniline were processed as described in Example 33C to provide the title compound. MS (APCI) m/z 535 (M+H)⁺.

Example 45B 5-((3aR,6aS)-hexahydropyrrolo[3,4-c]pyrrol-2(1H)-yl)-N-(3-iodophenyl)nicotinamide The product from Example 45A was processed as described in Example 31C to provide the title compound as the fumaric acid salt. ¹H NMR (300 MHz, CD₃OD) δ ppm 3.23-3.35 (m, 4H), 3.42-3.68 (m, 6H), 6.69 (s, 2H; C₄H₄O₄), 7.13 (t, J=8.1 Hz, 1H), 7.52 (ddd, J=7.9, 1.6, 1.0 Hz, 1H), 7.59 (dd, J=2.7, 2.0 Hz, 1H), 7.69 (ddd, J=8.1, 2.0, 1.0 Hz, 1H), 8.15-8.25 (m, 2H), 8.44 (d, J=2.0 Hz, 1H); MS (ESI) m/z 435 (M+H)⁺.

Example 46

N-benzyl-5-((3aR,6aS)-hexahydropyrrolo[3,4-c]pyrrol-2(1H)-yl)-N-methylnicotinamide

Example 46A

(3aR,6aS)-tert-butyl 5-(5-(benzyl(methyl)carbamoyl)pyridin-3-yl)hexahydropyrrolo[3,4-c]pyrrole-2(1H)-carboxylate The product from Example 33B and N-methylbenzylamine were processed as described in Example 33C to provide the title compound. MS (APCI) m/z 437 (M+H)$^+$.

Example 46B

N-benzyl-5-((3aR,6aS)-hexahydropyrrolo[3,4-c]pyrrol-2(1H)-yl)-N-methylnicotinamide The product from Example 46A was processed as described in Example 31C to provide the title compound as the fumaric acid salt. $^1$H NMR (300 MHz, CD$_3$OD) δ ppm 2.92, 3.07 (s, s, 3H; rotamers), 3.20-3.33 (m, 4H), 3.36-3.67 (m, 6H), 4.55, 4.76 (s, s, 2H; rotamers), 6.70 (s, 3H; C$_4$H$_4$O$_4$), 7.07-7.24 (m, 2H), 7.27-7.42 (m, 4H), 7.99 (s, 1H), 8.04-8.14 (m, J=10.9, 1.7 Hz, 1H); MS (ESI) m/z 337 (M+H)$^+$.

Example 47

N-(benzo[d]thiazol-6-yl)-5-((3aR,6aS)-hexahydropyrrolo[3,4-c]pyrrol-2(1H)-yl)nicotinamide

Example 47A

(3aR,6aS)-tert-butyl 5-(5-(benzo[d]thiazol-6-ylcarbamoyl)pyridin-3-yl)hexahydropyrrolo[3,4-c]pyrrole-2(1H)-carboxylate The product from Example 33B and 6-aminobenzothiazole were processed as described in Example 33C to provide the title compound. MS (APCI) m/z 466 (M+H)$^+$.

Example 47B

N-(benzo[d]thiazol-6-yl)-5-((3aR,6aS)-hexahydropyrrolo[3,4-c]pyrrol-2(1H)-yl)nicotinamide The product from Example 47A was processed as described in Example 31C to provide the title compound as the hemifumaric acid salt. $^1$H NMR (300 MHz, CD$_3$OD) δ ppm 3.20-3.35 (m, 4H), 3.42-3.66 (m, 6H), 6.61 (s, 1H; C$_4$H$_4$O$_4$), 7.62 (dd, J=2.7, 1.7 Hz, 1H), 7.78 (dd, J=8.8, 2.0 Hz, 1H), 8.04 (d, J=8.8 Hz, 1H), 8.17 (d, J=2.7 Hz, 1H), 8.47 (d, J=1.7 Hz, 1H), 8.61 (d, J=1.7 Hz, 1H), 9.18 (s, 1H); MS (DCI/NH$_3$) m/z 366 (M+H)$^+$.

Example 48

N-(3,5-bis(trifluoromethyl)phenyl)-5-((3aR,6aS)-hexahydropyrrolo[3,4-c]pyrrol-2(1H)-yl)nicotinamide

Example 48A

(3aR,6aS)-tert-butyl 5-(5-(3,5-bis(trifluoromethyl)phenylcarbamoyl)pyridin-3-yl)hexahydropyrrolo[3,4-c]pyrrole-2(1H)-carboxylate The product from Example 33B and 3,5-bis(trifluoromethyl)aniline were processed as described in Example 33C to provide the title compound. MS (APCI) m/z 545 (M+H)$^+$.

Example 48B

N-(3,5-bis(trifluoromethyl)phenyl)-5-((3aR,6aS)-hexahydropyrrolo[3,4-c]pyrrol-2(1H)-yl)nicotinamide The product from Example 48A was processed as described in Example 31C to provide the title compound as the fumaric acid salt. $^1$H NMR (300 MHz, CD$_3$OD) δ ppm 3.23-3.35 (m, 4H), 3.45-3.67 (m, 6H), 6.75 (s, 2H; C$_4$H$_4$O$_4$), 7.65 (dd, J=2.7, 2.0 Hz, 1H), 7.71-7.74 (m, 1H), 8.22 (d, J=3.1 Hz, 1H), 8.41 (br s, 2H), 8.51 (d, J=1.7 Hz, 1H); MS (ESI) m/z 445 (M+H)$^+$.

Example 49

N-(4-chlorophenyl)-5-((3aR,6aS)-hexahydropyrrolo[3,4-c]pyrrol-2(1H)-yl)nicotinamide

Example 49A

(3aR,6aS)-tert-butyl 5-(5-(4-chlorophenylcarbamoyl)pyridin-3-yl)hexahydropyrrolo[3,4-c]pyrrole-2(1H)-carboxylate The product from Example 33B and 4-chloroaniline were processed as described in Example 33C to provide the title compound. MS (APCI) m/z 443 (M+H)$^+$.

Example 49B

N-(4-chlorophenyl)-5-((3aR,6aS)-hexahydropyrrolo[3,4-c]pyrrol-2(1H)-yl)nicotinamide The product from Example 49A was processed as described in Example 31C to provide the title compound as the fumaric acid salt. $^1$H NMR (300 MHz, CD$_3$OD) δ ppm 3.22-3.35 (m, 4H), 3.43-3.68 (m, 6H), 6.70 (s, 3H; C$_4$H$_4$O$_4$), 7.33-7.41 (m, 2H), 7.59 (dd, J=2.7, 2.0 Hz, 1H), 7.67-7.80 (m, 2H), 8.18 (d, J=2.7 Hz, 1H), 8.45 (d, J=1.7 Hz, 1H); MS (ESI) m/z 343 (M+H)$^+$.

Example 50

5-((3aR,6aS)-hexahydropyrrolo[3,4-c]pyrrol-2(1H)-yl)-N-(4-phenoxyphenyl)nicotinamide

Example 50A

(3aR,6aS)-tert-butyl 5-(5-(4-phenoxyphenylcarbamoyl)pyridin-3-yl)hexahydropyrrolo[3,4-c]pyrrole-2(1H)-carboxylate The product from Example 33B and 4-phenoxyaniline were processed as described in Example 33C to provide the title compound. MS (APCI) m/z 501 (M+H)$^+$.

Example 50B

5-((3aR,6aS)-hexahydropyrrolo[3,4-c]pyrrol-2(1H)-yl-N-(4-phenoxyphenyl)nicotinamide The product from Example 50A was processed as described in Example 31C to provide the title compound as a free base. $^1$H NMR (300 MHz, CD$_3$OD) δ ppm 2.89 (dd, J=11.5, 3.7 Hz, 2H), 3.03-3.13 (m, 2H), 3.20-3.35 (m, 2H), 3.36-3.44 (m, 2H), 3.47-3.56 (m, 2H), 6.95-7.04 (m, 4H), 7.10 (tt, J=7.4, 1.1 Hz, 1H), 7.29-7.40 (m, 2H), 7.55 (dd, J=2.7, 2.0 Hz, 1H), 7.63-7.72 (m, 2H), 8.13 (d, J=2.7 Hz, 1H), 8.39 (d, J=1.7 Hz, 1H); MS (DCI/NH$_3$) m/z 401 (M+H)$^+$; Anal. (C$_{24}$H$_{24}$N$_4$O$_2$.0.5H$_2$O) C, H, N.

Example 51

N-(3,4-dichlorophenethyl)-5-((3aR,6aS)-hexahydropyrrolo[3,4-c]pyrrol-2(1H)-yl)nicotinamide

Example 51A

(3aR,6aS)-tert-butyl 5-(5-(3,4-dichlorophenethylcarbamoyl)pyridin-3-yl)hexahydropyrrolo[3,4-c]pyrrole-2(1H)-carboxylate The product from Example 33B and 3,4-dichlorophenethylamine were processed as described in Example 33C to provide the title compound. MS (APCI) m/z 505 (M+H)$^+$.

Example 51B

N-(3,4-dichlorophenethyl)-5-((3aR,6aS)-hexahydropyrrolo[3,4-c]pyrrol-2(1H)-yl)nicotinamide The product from Example 51B was processed as described in Example 31C to provide the title compound as the fumaric acid salt. $^1$H NMR (300 MHz, CD$_3$OD) δ ppm 2.91 (t, J=7.0 Hz, 2H), 3.21-3.35 (m, 4H), 3.40-3.67 (m, 8H), 6.69 (s, 2H; C$_4$H$_4$O$_4$), 7.19 (dd, J=8.5, 2.0 Hz, 1H), 7.41 (dd, J=2.7, 1.7 Hz, 1H), 7.41-7.45 (m, 2H), 8.12 (d, J=2.7 Hz, 1H), 8.25 (d, J=1.7 Hz, 1H); MS (DCI/NH$_3$) m/z 405 (M+H)$^+$.

Example 52

N-(3-fluoro-5-(trifluoromethyl)benzyl)-5-((3aR,6aS)-hexahydropyrrolo[3,4-c]pyrrol-2(1H)-yl)nicotinamide

Example 52A

(3aR,6aS)-tert-butyl 5-(5-(3-fluoro-5-(trifluoromethyl)benzylcarbamoyl)pyridin-3-yl)hexahydropyrrolo[3,4-c]pyrrole-2(1H)-carboxylate The product from Example 33B and 3-fluoro-5-trifluoromethylbenzylamine were processed as described in Example 33C to provide the title compound. MS (APCI) m/z 509 (M+H)$^+$.

Example 52B

N-3-fluoro-5-(trifluoromethyl)benzyl)-5-((3aR,6aS)-hexahydropyrrolo[3,4-c]-2(1H)-yl)nicotinamide The product from Example 52A was processed as described in Example 31C to provide the title compound as the fumaric acid salt. $^1$H NMR (300 MHz, CD$_3$OD) δ ppm 3.20-3.35 (m, 4H), 3.41-3.67 (m, 6H), 4.65 (s, 2H), 6.68 (s, 3H; C$_4$H$_4$O$_4$), 7.33-7.43 (m, 2H), 7.51 (brs, 1H), 7.54 (dd, J=2.7, 2.0 Hz, 1H), 8.16 (d, J=2.7 Hz, 1H), 8.38 (d, J=2.0 Hz, 1H); MS (ESI) m/z 409 (M+H)$^+$; Anal. (C$_{20}$H$_{20}$F$_4$N$_4$O.1.55 C$_4$H$_4$O$_4$) C, H, N.

Example 53

N-(3,5-difluorophenyl)-5-((3aR,6aR)-hexahydropyrrolo[3,4-b]pyrrol-1(2H)-yl)nicotinamide

Example 53A

5-bromo-N-(3,5-difluorophenyl)nicotinamide

Oxalyl chloride (1.2 mL) and DMF (25 μL) were added to 5-bromonicotinic acid (1.0 g, 4.95 mmol) suspended in CH$_2$Cl$_2$ (30 mL). The resulting mixture was stirred at room temperature for 12 min. It was then concentrated to dryness and azeotroped with toluene. The residual was then dissolved in toluene (30 mL). 3,5-Difluoroaniline (1.0 g, 7.8 mmol) was added followed by triethylamine (1.1 mL, 7.5 mmol). The resulting suspension was stirred at room temperature for 10 min. The reaction mixture was taken in 5% acetic acid$_{(aq)}$ (300 mL) and extracted with ethyl acetate (2×200 mL). The combined organic extract was washed with 1.0 M Na$_2$CO$_{3(aq)}$ (2×100 mL) and brine. The organic layers were combined, dried (Na$_2$SO$_4$) and concentrated to dryness to provide the title compound (1.4 g, 93%). MS (APCI) m/z 313, 315 (M+H)$^+$.

Example 53B

(3aR,6aR)-tert-butyl 1-(5-(3,5-difluorophenylcarbamoyl)pyridin-3-yl)hexahydropyrrolo[3,2-c]pyrrole-5(1H)-carboxylate A suspension of (3aR,6aR)-tert-butyl hexahydropyrrolo[3,4-b]pyrrole-5(1H)-carboxylate (85 mg, 0.40 mmol, prepared as described in WO2001081347), the product from Example 53A (97 mg, 0.37 mmol), tris(dibenzylideneacetone)dipalladium(0) (13.4 mg, 0.015 mmol), 4,5-bis(diphenylphosphino)-9,9-dimethylxanthene (25 mg, 0.044 mmol) and cesium carbonate (190 mg, 0.58 mmol) in anhydrous dioxane (4 mL) was heated at 90° C. for 18 hours. The reaction mixture was cooled and filtered through a glass frit. The filtrate was concentrated and the residue was purified by silica gel chromatography (EtOAc, $R_f$=0.4) to afford the title compound. MS (APCI) m/z=445 (M+H)$^+$.

Example 53C

N-(3,5-difluorophenyl)-5-((3aR,6aR)-hexahydropyrrolo[3,4-b]pyrrol-1(2H)-yl)nicotinamide The product from Example 53B was processed as described in Example 31C to provide the title compound as the fumaric acid salt. $^1$H NMR (300 MHz, CD$_3$OD) δ ppm 1.95-2.11 (m, 1H), 2.23-2.46 (m, 1H), 3.25-3.37 (m, 2H), 3.38-3.61 (m, 4H), 3.76 (dt, J=9.6, 6.9 Hz, 1H), 4.45-4.54 (m, 1H), 6.66 (s, 2H; C$_4$H$_4$O$_4$), 6.73 (tt, J=9.2, 2.4 Hz, 1H), 7.39-7.49 (m, 2H), 7.52 (dd, J=2.7, 2.0 Hz, 1H), 8.15 (d, J=3.1 Hz, 1H), 8.45 (d, J=1.7 Hz, 1H); MS (DCI/NH$_3$) m/z 345 (M+H)$^+$; Anal. (C$_{18}$H$_{18}$F$_2$N$_4$O.1 C$_4$H$_4$O$_4$.0.65H$_2$O) C, H, N.

Example 54

N-(3,5-difluorophenyl)-5-((3aS,6aS)-hexahydropyrrolo[3,4-b]pyrrol-1(2H)-yl)nicotinamide

Example 54A (3aS,6aS)-tert-butyl 1-(5-(3,5-difluorophenylcarbamoyl)pyridin-3-yl)hexahydropyrrolo[3,2-c]pyrrole-5(1H)-carboxylate The product from Example 53A and (3aS,6aS)-tert-butyl hexahydropyrrolo[3,4-b]pyrrole-5(1H)-carboxylate (prepared as described in WO2001081347) were processed as described in Example 53B to provide the title compound. MS (APCI) m/z=445 (M+H)$^+$.

Example 54B

N-(3,5-difluorophenyl)-5-((3aS,6aS)-hexahydropyrrolo[3,4-b]pyrrol-1(2H)-yl)nicotinamide The product from Example 54A was processed as described in Example 31C to provide the title compound as the fumaric acid salt. $^1$H NMR (300 MHz, CD$_3$OD) δ ppm 1.97-2.13 (m, 1H), 2.28-2.43 (m, 1H), 3.27-3.39 (m, 2H), 3.40-3.66 (m, 4H), 3.72-3.83 (m, 1H), 4.47-4.55 (m, 1H), 6.74 (tt, J=9.2, 2.4 Hz, 1H), 6.74 (s, 2H; C$_4$H$_4$O$_4$), 7.38-7.49 (m, 2H), 7.53 (dd, J=3.1, 1.7 Hz, 1H), 8.16 (d, J=3.1 Hz, 1H), 8.48 (d, J=1.7 Hz, 1H); MS (ESI) m/z 345 (M+H)$^+$.

Example 55

N-(3,5-difluorophenyl)-5-((3aS,6aS)-hexahydropyrrolo[3,4-b]pyrrol-5(1H)-yl)nicotinamide

Example 55A (3aS,6aS)-tert-butyl 5-(5-(3,5-difluorophenylcarbamoyl)pyridin-3-yl)hexahydropyrrolo[2,3-c]pyrrole-1(2H)-carboxylate The product from Example 53A and (3aS,6aS)-tert-butyl hexahydropyrrolo[3,4-b]pyrrole-1(2H)-carboxylate (prepared as described in WO2001081347) were processed as described in Example 53B to provide the title compound. MS (APCI) m/z=445 (M+H)$^+$.

Example 55B

N-(3,5-difluorophenyl)-5-((3aS,6aS)-hexahydropyrrolo[3,4-b]pyrrol-5(1H)-yl)nicotinamide The product from Example 55A was processed as described in Example 31C to provide the title compound as the fumaric acid salt. $^1$H NMR (300 MHz, CD$_3$OD) δ ppm 2.00-2.14 (m, 1H), 2.36 (ddd, J=15.4, 13.4, 7.8 Hz, 1H), 3.25-3.39 (m, 2H), 3.42-3.59 (m, 4H), 3.92 (dd, J=11.9, 1.7 Hz, 1H), 4.41 (ddd, J=7.5, 6.1, 1.4 Hz, 1H), 6.64 (s, 2H; C$_4$H$_4$O$_4$), 6.73 (tt, J=9.2, 2.4 Hz, 1H), 7.38-7.51 (m, 2H), 7.62 (dd, J=2.9, 1.9 Hz, 1H), 8.21 (d, J=3.1 Hz, 1H), 8.47 (d, J=2.0 Hz, 1H); MS (ESI) m/z 345 (M+H)$^+$; Anal. (C$_{18}$H$_{18}$F$_2$N$_4$O.1.05 C$_4$H$_4$O$_4$.0.4H$_2$O) C, H, N.

Example 56

(3,4-dihydroisoquinolin-2(1H)-yl)(5-((3aR,6aS)-hexahydropyrrolo[3,4-c]pyrrol-2(1H)-yl)pyridin-3-yl)methanone

Example 56A (3aR,6aS)-tert-butyl 5-(5-(1,2,3,4-tetrahydroisoquinoline-2-carbonyl)pyridin-3-yl)hexahydropyrrolo[3,4-c]pyrrole-2(1H)-carboxylate The product from Example 33B and 1,2,3,4-tetrahydroisoquinoline were processed as described in Example 33C to provide the title compound: MS (APCI) m/z 449 (M+H)$^+$.

Example 56B (3,4-dihydroisoquinolin-2(1H)-yl)(5-((3aR,6aS)-hexahydropyrrolo[3,4-c]pyrrol-2(1H)-yl)pyridin-3-yl)methanone The product from Example 56A was processed as described in Example 31C to provide the title compound as the fumaric acid salt. $^1$H NMR (300 MHz, CD$_3$OD) δ ppm 2.86-3.02 (m, 2H), 3.19-3.29 (m, 4H), 3.39-3.72 (m, 8H), 3.91-4.05 (m, 1H), 4.61 (br s, 1H), 6.68 (s, 2H; C$_4$H$_4$O$_4$), 7.04-7.25 (m, 5H), 8.00 (br s, 1H), 8.12 (d, J=2.7 Hz, 1H); MS (APCI) m/z 349 (M+H)$^+$; Anal. (C$_2$, H$_{24}$N$_4$O.1.4 C$_4$H$_4$O$_4$) C, H, N.

Example 57

N-(3,5-difluorophenyl)-5-((3aR,6aS)-5-(pyridin-3-ylmethyl)hexahydropyrrolo[3,4-c]pyrrol-2(1H)-yl)nicotinamide The product from Example 42B (40 mg, 0.087 mmol) was dissolved in MeOH (10 mL). Sodium triacetoxyborohydride (123 mg, 0.58 mmol) and nicotinaldehyde (64 mg, 0.58 mmol) was added and the reaction mixture was stirred at ambient temperature for 1 h. It was then concentrated under reduced pressure, and the resulting material was purified by preparative HPLC [Waters® XTerra RP18 column, 5 μm, 30×100 mm, flow rate 40 mL/minute, 5-95% gradient of acetonitrile in buffer (0.1 M aqueous ammonium bicarbonate, adjusted to pH 10 with ammonium hydroxide)] to afford the product as its free base. This was dissolved in ether/methanol (10:1) and treated with fumaric acid to afford the title compound as the fumaric acid salt. $^1$H NMR (300 MHz, CD$_3$OD) δ ppm 3.02-3.12 (m, 2H), 3.21-3.35 (m, 2H), 3.36-3.45 (m, 2H), 3.47-3.61 (m, 4H), 4.25-4.27 (m, 2H), 6.69-6.80 (m, 1H), 6.74 (s, 2H; C$_4$H$_4$O$_4$), 7.39-7.49 (m, 2H), 7.53 (dd, J=8.0, 4.9 Hz, 1H), 7.58-7.64 (m, 1H), 7.98 (ddd, J=8.0, 1.9, 1.7 Hz, 1H), 8.21 (d, J=2.7 Hz, 1H), 8.45 (d, J=1.7 Hz, 1H), 8.60 (dd, J=4.9, 1.2 Hz, 1H), 8.65 (d, J=2.0 Hz, 1H); MS (DCI/NH$_3$) m/z 436 (M+H)$^+$.

Example 58

(3aS,6aS)-1-(5-(benzyloxy)pyridin-3-yl)octahydro-pyrrolo[3,4-b]pyrrole

Example 58A (3aS,6aS)-tert-butyl 1-(5-(benzyloxy)pyridin-3-yl)hexahydropyrrolo[3,4-b]pyrrole-5(1H)-carboxylate 3-(Benzyloxy)-5-bromopyridine and (3aS,6aS)-tert-butyl hexahydropyrrolo[3,4-b]pyrrole-5(1H)-carboxylate (prepared as described in WO2001081347) were processed as described in Example 53B to provide the title compound. MS (ESI) m/z 396 (M+H)$^+$.

Example 58B (3aS,6aS)-1-(5-(benzyloxy) pyridin-3-yl)octahydropyrrolo[3,4-b]pyrrole The product from Example 58A was processed as described in Example 31C to provide the title compound as the fumaric acid salt. $^1$H NMR (300 MHz, CD$_3$OD) δ ppm 1.91-2.05 (m, 1H), 2.22-2.38 (m, 1H), 3.22-3.37 (m, 4H), 3.40-3.51 (m, 2H), 3.66 (ddd, J=9.2, 7.1, 6.8 Hz, 1H), 4.33-4.43 (m, 1H), 5.17 (s, 2H), 6.65 (t, J=2.4 Hz, 1H), 6.68 (s, 2H; C$_4$H$_4$O$_4$), 7.28-7.41 (m, 3H), 7.42-7.47 (m, 2H), 7.57 (d, J=2.4 Hz, 1H), 7.73 (d, J=2.4 Hz, 1H); MS (DCI/NH$_3$) m/z 296 (M+H)$^+$.

Example 59

(3aR,6aS)-2-(5-(benzyloxy)pyridin-3-yl)octahydro-pyrrolo[3,4-c]pyrrole

Example 59A (3aR,6aS)-tert-butyl 5-(5-(benzyloxy)pyridin-3-yl)hexahydropyrrolo[3,4-c]pyrrole-2(1H)-carboxylate 3-(Benzyloxy)-5-bromopyridine and the product from Example 1C were processed as described in Example 53B to provide the title compound. MS (ESI) m/z 396 (M+H)$^+$.

Example 59B (3aR,6aS)-2-(5-(benzyloxy)pyridin-3-yl)octahydro-pyrrolo[3,4-c]pyrrole The product from Example 59A was processed as described in Example 31C to provide the title compound as the fumaric acid salt. $^1$H NMR (300 MHz, CD$_3$OD) δ ppm 3.17-3.39 (m, 6H), 3.43-3.66 (m, 4H), 5.15 (s, 2H), 6.68 (s, 2H; C$_4$H$_4$O$_4$), 6.76 (t, J=2.4 Hz, 1H), 7.31-7.46 (m, 3H), 7.64 (d, J=2.4 Hz, 1H), 7.72 (d, J=2.4 Hz, 1H); MS (ESI) m/z 296 (M+H)$^+$.

Example 60

(3aR,6aS)-2-(5-(benzyloxy)pyridin-3-yl)-5-methyloctahydropyrrolo[3,4-c]pyrrole

The product from Example 59B was reacted with sodium triacetoxyborohydride and formaldehyde (37% aqueous solution) as described in Example 57 to provide the title compound as the fumaric acid salt. $^1$H NMR (300 MHz, CD$_3$OD) δ ppm 2.89 (s, 3H), 3.21-3.35 (m, 6H), 3.48-3.56 (m, 2H), 3.56-3.66 (m, 2H), 5.15 (s, 2H), 6.69 (s, 3H; C$_4$H$_4$O$_4$), 6.80 (t, J=2.4 Hz, 1H), 7.28-7.46 (m, 5H), 7.68 (d, J=2.4 Hz, 1H), 7.74 (d, J=2.4 Hz, 1H); MS (ESI) m/z 310 (M+H)$^+$; Anal. (C$_{19}$H$_{23}$N$_3$O.1.7 C$_4$H$_4$O$_4$) C, H, N.

Example 61

(3aR,6aS)-2-(5-(benzyloxy)pyridin-3-yl)-5-(pyridin-2-ylmethyl)octahydropyrrolo[3,4-c]pyrrole The product from Example 59B was reacted with sodium triacetoxyborohydride and 2-pyridinecarboxaldehyde as described in Example 57 to provide the title compound as the fumaric acid salt. $^1$H NMR (300 MHz, CD$_3$OD) δ ppm 3.07-3.16 (m, 2H), 3.19-3.35 (m, 6H), 3.45-3.51 (m, 2H), 3.55-3.67 (m, 2H), 4.37 (s, 2H), 5.15 (s, 2H), 6.71 (s, 3H; C$_4$H$_4$O$_4$), 6.79 (t, J=2.4 Hz, 1H), 7.30-7.50 (m, 7H), 7.66 (d, J=2.4 Hz, 1H), 7.72 (d, J=2.4 Hz, 1H), 7.86 (td, J=7.7, 1.9 Hz, 1H), 8.61 (ddd, J=4.9, 1.7, 0.8 Hz, 1H); MS (DCI/NH$_3$) m/z 387 (M+H)$^+$.

Example 62

(3aR,6aS)-2-(5-(benzyloxy)pyridin-3-yl)-5-(pyridin-3-ylmethyl)octahydropyrrolo[3,4-c]pyrrole The product from Example 59B was reacted with sodium triacetoxyborohydride and nicotinaldehyde as described in Example 57 to provide the title compound as the fumaric acid salt. $^1$H NMR (300 MHz, CD$_3$OD) δ ppm 2.89 (dd, J=10.5, 5.1 Hz, 2H), 3.08-3.21 (m, 2H), 3.24-3.35 (m, 4H), 3.37-3.44 (m, 2H), 4.08 (s, 2H), 5.15 (s, 2H), 6.72 (s, 3H; C$_4$H$_4$O$_4$), 6.78 (t, J=2.4 Hz, 1H), 7.29-7.52 (m, 6H), 7.64 (d, J=1.4 Hz, 1H), 7.70 (d, J=1.7 Hz, 1H), 7.92 (dt, J=7.9, 2.0 Hz, 1H), 8.55 (dd, J=4.7, 1.4 Hz, 1H), 8.60 (d, J=1.4 Hz, 1H); MS (ESI) m/z 387 (M+H)$^+$.

Example 63

N-(3,5-difluorophenyl)-5-((3aR,6aS)-hexahydropyrrolo[3,4-c]pyrrol-2(1H)-yl)pyridine-3-carbothioamide Example 63A (3aR,6aS)-tert-butyl 5-(5-(3,5-difluorophenylcarbamothioyl)pyridin-3-yl)hexahydropyrrolo[3,4-c]pyrrole-2(1H)-carboxylate The product from Example 42A (60 mg, 0.14 mmol) and Lawesson's reagent (27 mg, 0.068 mmol) were combined with toluene (3 mL) and stirred at 110° C. for 18 h. After cooling to room temperature, the reaction mixture was concentrated under reduced pressure and purified by silica gel flash chromatography (EtOAc, $R_f$=0.35) to provide the title compound (60 mg, 97%). MS (APCI) m/z 387 (M+H)$^+$.

Example 63B

N-(3,5-difluorophenyl)-5-((3aR,6aS)-hexahydropyrrolo[3,4-c]pyrrol-2(1H)-yl)pyridine-3-carbothioamide The product from Example 63A was processed as described in Example 31C to provide the title compound as the fumaric acid salt. $^1$H NMR (300 MHz, CD$_3$OD) δ ppm 3.22-3.34 (m, 4H), 3.43-3.51 (m, 2H), 3.52-3.68 (m, 4H), 6.72-6.78 (m, 3H), 6.88 (tt, J=9.0, 2.4 Hz, 1H), 7.50-7.58 (m, 1H), 7.60-7.73 (m, 2H), 8.11 (d, J=2.7 Hz, 1H), 8.27 (s, 1H); MS (ESI) m/z 361 (M+H)$^+$.

Example 64

(3aR,6aS)-5-(5-(4-Chlorophenoxyimino)methyl)pyridin-3-yl)hexahydropyrrolo[3,4-c]pyrrole Example 64A (3aR,6aS)-tert-Butyl 5-(5-bromopyridin-3-yl)hexahydropyrrolo[3,4-c]pyrrole-2(1H-carboxylate The product from example 1C (541 mg, 2.55 mmol) and 3,5-dibromopyridine (724 mg, 3.06 mmol) were combined in a 100 mL flask with toluene (14 mL). The solution was stirred at room temperature as sodium t-butoxide (367 mg, 3.82 mmol) was added as a solid. In a test tube, racemic-2,2'-bis(diphenylphosphino-1,1'-binaphthyl) (31 mg, 0.05 mmol) and tris(dibenzylideneacetone)dipalladium (0) (22 mg, 0.024 mmol) were combined with toluene (2 mL) and the mixture was heated at 70° C. for 5 min, then cooled to room temperature. This mixture was rinsed into the 100 mL flask with toluene (2 mL), and the reaction flask was evacuated and purged with nitrogen (3 cycles). The mixture was heated at 80° C. for 20 h, then cooled to room temperature and loaded onto a column of silica gel (45 g) and eluted with hexanes-EtOAc (1:1) to provide the titled compound as an off-white solid (0.51 g, 54%). $^1$H NMR (300 MHz, CD$_3$OD) δ ppm 1.45 (s, 9H), 3.00-3.14 (m, 2H), 3.20-3.28 (m, 2H), 3.26-3.31 (m, 2H), 3.50-3.59 (m, 2H), 3.59-3.71 (m, 2H), 7.14-7.19 (m, 1H), 7.79-7.90 (m, 2H).

Example 64B

O-(4-Chlorophenyl)hydroxylamine Hydrochloride

A mixture of N-hydroxyphthalimide (664 mg, 4.07 mmol), 4-chlorophenylboronic acid (635 mg, 4.06 mmol) and powdered 4 Å molecular sieves (1.02 g) in dichloromethane (20 mL) was stirred open to the air. Pyridine (0.37 mL, 4.6 mmol) and Cu(OAc)$_2$-H$_2$O (812 mg, 4.07 mmol) were added, and stirring was continued for 18 h. Silica gel (10 g) was added, and the mixture was concentrated to dryness. The residue was added to the top of a silica gel chromatography column, and eluted with hexanes-EtOAc (4:1) to provide 24-chlorophenoxy)phthalimide as a white solid (820 mg). This was dissolved in chloroform (37 mL) and methanol (4 mL) and hydrazine hydrate (0.56 mL, 12 mmol) was added. The solution was stirred at room temperature for 24 h. Silica gel (10 g) was added, and the slurry was concentrated to dryness. The solid was added to the top of a silica gel chromatography column, and eluted with hexanes-EtOAc (4:1) to provide O-(4-chlorophenyl)hydroxylamine as a yellow oil (416 mg). This was dissolved in ethanol (5 mL) and treated with HCl/dioxane (4N, 1 mL), followed by gradual addition of EtOAc (50 mL) to precipitate the product. The mixture was filtered and dried under vacuum to provide the titled salt as an off-white crystalline solid (442 mg, 60%). $^1$H NMR (300 MHz, CD$_3$OD) δ ppm 7.15-7.22 (m, 2H), 7.42-7.49 (m, 2H).

Example 64C (3aR,6aS)-tert-Butyl 5-(5-(4-chlorophenoxyimino)methyl)pyridin-3-yl)hexahydropyrrolo[3,4-c]pyrrole-2(1H)-carboxylate A solution of the product from Example 64A (115 mg, 0.31 mmol) in dry THF (8 mL) was cooled to −70° C. under nitrogen. tert-Butyllithium (1.18 M in pentane, 0.61 mL, 0.72 mmol) was added dropwise over 5 min, and the resulting amber-colored solution was stirred for 20 min at −70° C. N,N-Dimethylformamide (0.1 mL) was added, and the mixture was allowed to warm to room temperature. A solution of the product from Example 64B (42 mg, 0.23 mmol) in methanol (1 mL) was added, and the mixture was stirred at ambient temperature for 2 h, then concentrated under vacuum. The residue was purified by flash chromatography (silica gel, eluted with hexanes-EtOAc 4:1) to provide the titled compound as a colorless gum (32 mg, 23%). $^1$H NMR (300 MHz, CD$_3$OD) δ ppm 1.46 (s, 9H), 3.01-3.16 (m, 2H), 3.03-3.17 (m, 4H), 3.25-3.31 (m, 2H), 3.55-3.76 (m, 4H), 7.20-7.26 (m, 2H), 7.30-7.36 (m, 2H), 7.95-8.01 (m, 2H), 8.13-8.18 (m, 1H), 8.52 (s, 1H); MS (DCI/NH$_3$) m/z 443 (M+H)$^+$.

Example 64D (3aR,6aS)-5-(5-(4-Chlorophenoxyimino)methyl)pyridin-3-yl)hexahydropyrrolo[3,4-c]pyrrole A solution of HCl/dioxane (4N, 1 mL) was added to a solution of the product from Example 64C (32 mg) in dichloromethane (10 mL), and stirred at room temperature for 40 h. The mixture was concentrated under vacuum, and the residue was crystallized from EtOAc-EtOH (5:1) to provide the hydrochloride salt of the title compound as an off-white solid (16 mg, 12% yield). $^1$H NMR (300 MHz, CD$_3$OD) δ ppm 3.10-3.24 (m, 2H), 3.34-3.53 (m, 4H), 3.60-3.78 (m, 4H), 7.26-7.32 (m, 2H), 7.31-7.40 (m, 2H), 7.83-7.96 (m, 1H), 8.07 (d, J=2.7 Hz, 1H), 8.38 (s, 1H), 8.66 (s, 1H); MS (DCI/NH$_3$) m/z 343 (M+H)$^+$.

Example 65

(3aR,6aS)-5-(5-(4-Benzyloxyimino)methyl)pyridin-3-yl)hexahydropyrrolo[3,4-c]pyrrole Prepared in 15% yield from the product from Example 64A according to the procedures of Examples 64C and 64D, but substituting O-benzylhydroxylamine hydrochloride for O-(4-chlorophenyl)hydroxylamine hydrochloride. The hydrochloride salt of the title compound was obtained as a white solid. $^1$H NMR (300 MHz, CD$_3$OD) δ ppm 3.25-3.38 (m, 4H), 3.52-3.60 (m, 2H), 3.59-3.70 (m, 4H), 5.27 (s, 2H), 7.29-7.43 (m, 5H), 7.81-7.85 (m, 1H), 8.08 (d, J=2.7 Hz, 1H), 8.28 (s, 1H), 8.31 (s, 1H); MS (DCI/NH$_3$) m/z 323 (M+H)$^+$.

Example 66

1-(5-((3aR,6aS)-hexahydropyrrolo[3,4-c]pyrrol-2(1H)-yl)pyridin-3-yl)ethanone O-4-chlorophenyl Oxime

Example 66A

((3aR,6aS)-tert-Butyl 5-(5-(1-ethoxyvinyl)pyridin-3-yl)hexahydropyrrolo[3,4-c]pyrrole-2(1H)-carboxylate The product from Example 64A (107 mg, 0.29 mmol) and tributyl-(1-ethoxyvinyl)stannane (157 mg, 0.43 mmol) were combined in a 100 mL conical flask with toluene (4 mL). Tetrakis(triphenylphosphine)palladium(0) (19.7 mg, 0.017 mmol) was added, and the mixture was heated under nitrogen at 90° C. for 22 h. The black mixture was cooled to room temperature, applied to a column of silica gel and eluted with hexanes-EtOAc (1:1) to provide the titled compound as an amber gum (contaminated with triphenyl phosphine oxide, 47 mg, 47% pure, 21% yield). MS (DCI/NH$_3$) m/z 360 (M+H)$^+$.

Example 66B

1-(5-((3aR,6aS)-hexahydropyrrolo[3,4-c]pyrrol-2(1H)-yl)pyridin-3-yl)ethanone O-4-chlorophenyl oxime The product from Example 66A (47 mg, 0.06 mmol) was dissolved in ethanol (2 mL) and water (0.5 mL). O-(4-Chlorophenyl)hydroxylamine hydrochloride (14 mg, 0.08 mmol) was added, and the solution was stirred at ambient temperature for 21 h. The solvent was removed under vacuum, and the residue was taken up in dichloromethane (5 mL) and stirred at ambient temperature as trifluoroacetic acid (0.5 mL) was added. After 10 min, the solution was concentrated under vacuum and the residue was purified by flash chromatography (silica gel, eluted with dichloromethane-methanol-ammonium hydroxide (90:10:1) to provide the free base of the titled compound (15 mg). This was dissolved in ether-MeOH (9:1, 3 mL) and a solution of fumaric acid (5.7 mg) in the same solvent (1 mL) was added with stirring. A precipitate began to form after 30 seconds, and the mixture was stirred for 2 h to complete crystallization. The solid was filtered, washed with ether-MeOH (9:1) and dried under vacuum at 50° C. to provide the titled salt as a hemifumarate (12.5 mg, 49%). $^1$H NMR (300 MHz, CD$_3$OD) δ ppm 2.47 (s, 3H), 3.04-3.19 (m, 2H), 3.31-3.37 (m, 4H), 3.43-3.56 (m, 4H), 6.67 (s, 1H), 7.21-7.29 (m, 2H), 7.29-7.36 (m, 2H), 7.40-7.52 (m, 1H), 8.08 (d, J=2.7 Hz, 1H), 8.30 (d, J=1.7 Hz, 1H); MS (DCI/NH$_3$) m/z 357 (M+H)$^+$; Anal (C$_{19}$H$_{21}$N$_4$OCl.0.5C$_4$H$_4$O$_4$.0.7H$_2$O)C, H, N.

Compounds and Pharmaceutical Compositions Thereof

Compounds of the invention can have the general formula (I) as described above.

Particular values of variable groups in compounds of formula (I) are as follows. Such values may be used where appropriate with any of the other values, definitions, claims or embodiments defined hereinbefore or hereinafter.

As described generally in the Summary for compounds of formula (I), m and q are each independently 1 or 2; and n and p are each independently 0, 1, or 2. In certain embodiments, m, n, p, and q are 1. Examples of compounds of the invention thus include, but are not limited to, those having formula (Ia)

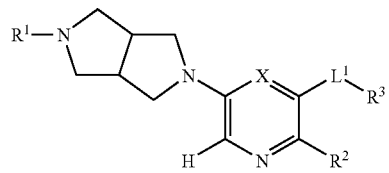
(Ia)

Wherein X, L$^1$, R$^1$, R$^2$ and R$^3$ are as described in the Summary.

In other embodiments, m and n are 1, q is 2, and p is 0. Examples of compounds of the invention thus include, but are not limited to, those having formula (Ib)

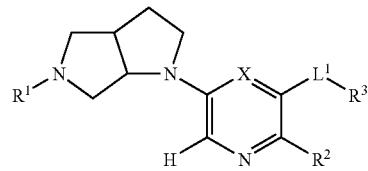
(Ib)

Wherein X, L$^1$, R$^1$, R$^2$ and R$^3$ are as described in the Summary.

In yet other embodiments, p and q are 1, m is 2, and n is 0. Examples of compounds of the invention thus include, but are not limited to, those having formula (Ic)

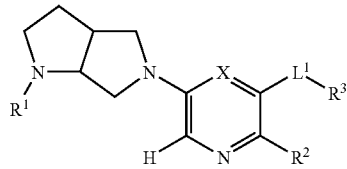
(Ic)

wherein X, L$^1$, R$^1$, R$^2$ and R$^3$ are as described in the Summary.

Included in this application are a group of compounds of formula (I), (Ia), (Ib), or (Ic) wherein X is CH. Other group of compounds that are contemplated include, but are not limited to, compounds of formula (I), (Ia), (Ib), or (Ic) wherein X is N.

Thus, one aspect of the invention is directed to a group of compounds having formula (I) wherein X is N and m, n, p, and q are 1, and, L$^1$, R$^1$, R$^2$ and R$^3$ are as described in the Summary.

Another aspect of the invention is directed to a group of compounds having formula (I) wherein X is N, m and n are 1, q is 2, and p is 0, and L$^1$, R$^1$, R$^2$, and R$^3$ are as described in the Summary.

Yet another aspect of the invention is directed to a group of compounds having formula (1) wherein X is N, p, and q are 1, m is 2, and n is 0, and L$^1$, R$^1$, R$^2$, and R$^3$ are as described in the Summary.

Yet another aspect of the invention is thus directed to a group of compounds having formula (I) wherein X is CH and m, n, p, and q are 1, and L$^1$, R$^1$, R$^2$, and R$^3$ are as described in the Summary.

Still other aspect of the invention is directed to a group of compounds having formula (I) wherein X is CH, m and n are 1, q is 2, and p is 0, and L$^1$, R$^1$, R$^2$, and R$^3$ are as described in the Summary.

A further aspect of the invention is directed to a group of compounds having formula (I) wherein X is CH, p, and q are 1, m is 2, and n is 0, and $L^1$, $R^1$, $R^2$, and $R^3$ are as described in the Summary.

For each of the foregoing groups of compounds of formula (I), (Ia), (Ib), and (Ic), examples include those wherein $L^1$ is —C(=Y)N($R^a$)—; Y is O; $R^a$ is hydrogen; and $R^3$ is $G^2$ wherein $G^2$ is aryl. Other examples include those wherein $L^1$ is —C(=Y)N($R^a$)—; Y is O; $R^a$ is hydrogen; $R^3$ is —(C$R^d R^e$)$_t$-$G^3$ or $G^2$; wherein $G^2$ and $G^3$ are each independently heteroaryl, and $R^d$ and $R^e$ are hydrogen. Other examples comprise those in which $L^1$ is —C(=Y)N($R^a$)—; Y is O; $R^a$ is hydrogen or alkyl; $R^3$ is —(C$R^d R^e$)$_t$-$G^3$ wherein $G^3$ is aryl; and $R^d$ and $R^e$, at each occurrence, are each independently hydrogen or alkyl. Yet other examples of each of the aforementioned groups included in the present application are those wherein $L^1$ is 0; $R^3$ is —(C$R^d R^e$)$_t$-$G^3$ wherein $G^3$ is aryl; and $R^d$ and $R^e$ at each occurrence, are each independently hydrogen, alkyl, or haloalkyl. Still other examples include those wherein $L^1$ is —N($R^a$)C(=Y)—; Y is O; $R^a$ is hydrogen; and $R^3$ is $G^2$ wherein $G^2$ is aryl. Still other examples include those wherein $L^1$ is a bond and $R^3$ is —$C_{2-4}$ alkenylenyl-$G^1$ wherein $G^1$ is aryl. Further included are examples in which $L^1$ is N($R^b$); $R^b$ is hydrogen; $R^3$ is —(C$R^d R^e$)$_t$-$G^3$ wherein $G^3$ is aryl; and $R^d$ and $R^e$ are hydrogen. Still other examples include those wherein $L^1$ is a bond and $R^3$ is —(C$R^d R^e$)$_t$-$G^3$ wherein $G^3$ is aryl; and $R^d$ and $R^e$ are hydrogen. Further examples include those wherein $L^1$ is —C(=Y)N($R^a$)—; Y is S, $R^a$ is hydrogen, and $R^3$ is $G^2$ wherein $G^2$ is aryl. Still other examples include those wherein $L^1$ is —C($R^c$)=N—O—; $R^c$ is hydrogen or alkyl; and $R^3$ is $G^2$ wherein $G^2$ is aryl. Still other examples include those wherein $L^1$ is —C($R^c$)=N—O—; $R^c$ is hydrogen; and $R^3$ is —(C$R^d R_e$)$_t$-$G^3$; wherein $G^3$ is aryl; and $R^d$ and $R^e$ are hydrogen. Still other examples include those wherein $L^1$ is C(=Y), Y is O, and $R^3$ is $G^2$ wherein $G^2$ is heterocycle.

For each of the aforementioned examples of compounds having formula (I), (Ia), (Ib), or (Ic), examples of $R^1$ include, but are not limited to, hydrogen, alkyl (e.g. methyl), and heteroarylalkyl (e.g. pyridinylmethyl) wherein the heteroaryl moiety is optionally substituted as disclosed in the Summary. Preferably, $R^1$ is hydrogen.

Embodiments of the present invention include any one of the compounds of formula (I), (Ia), (Ib), and (Ic) as described in the preceding paragraphs wherein $R^2$ is hydrogen.

The present compounds may exhibit the phenomena of tautomerism or structural isomerism. As the drawings within this specification can only represent one possible tautomeric or structural isomeric form, it should be understood that the invention encompasses any tautomeric or structural isomeric form, or mixtures thereof, which possess the ability to modulate α4β2 NNR activity, and is not limited to any one tautomeric or structural isomeric form utilized within the drawings.

Compounds comprising geometric isomers of carbon-carbon double bonds and carbon-nitrogen double are meant to be included in this invention. Substituents around a carbon-carbon or a carbon-nitrogen double bond are designated as being of Z or E configuration and substituents around a cycloalkyl or heterocycloalkyl are designated as being of cis or trans configuration.

Asymmetric centers exist in the present compounds. Individual stereoisomers of the compounds are prepared by synthesis from chiral starting materials or by preparation of racemic mixtures and separation by conversion to a mixture of diastereomers followed by separation or recrystallization, chromatographic techniques, or direct separation of the enantiomers on chiral chromatographic columns. Starting materials of particular stereochemistry are either commercially available or are made by the methods described herein and resolved by techniques well-known in the art.

Compounds of this invention contain at least one chiral stereogenic center and may exist as single stereoisomers (e.g. single enantiomer), mixtures of stereoisomers (e.g. any mixture of enantiomers or diastereomers) or racemic mixtures thereof. As a result, all stereoisomers of the compounds of the invention are meant to be included in the invention, including racemic mixtures, mixtures of diastereomers, mixtures of enantiomers, as well as individual optical isomers, including, enantiomers and single diastereomers of the compounds of the invention substantially free from their enantiomers or other diastereomers. By "substantially free" is meant greater than about 80% free of other enantiomers or diastereomers of the compound, more preferably greater than about 90% free of other enantiomers or diastereomers of the compound, even more preferably greater than about 95% free of other enantiomers or diastereomers of the compound, even more highly preferably greater than about 98% free of other enantiomers or diastereomers of the compound and most preferably greater than about 99% free of other enantiomers or diastereomers of the compound. Where the stereochemistry of the chiral stereogenic centers present in the chemical structures illustrated herein is not specified, the chemical structure is intended to encompass compounds containing either stereoisomer of each stereogenic center present in the compound.

Examples of some of the possible stereoisomeric form of the compounds of this invention include, but are not limited to compounds of formulae (I-i), (I-ii), (I-iii), and (I-iv):

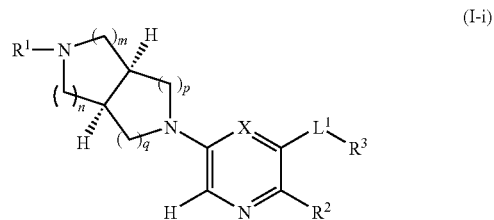

(I-i)

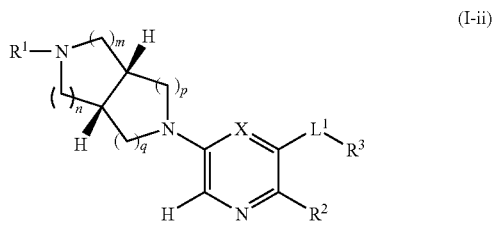

(I-ii)

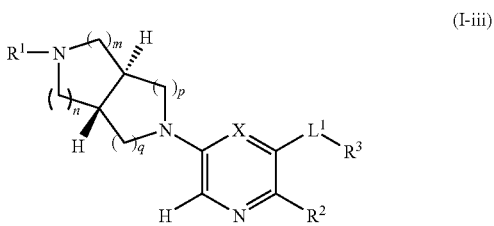

(I-iii)

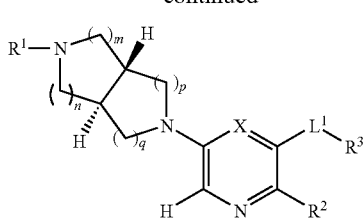
(I-iv)

It is understood that embodiments of $R^1$, $R^2$, $L^1$, m, n, p, q, and $R_3$ and combinations of embodiments, including preferred, more preferred, and most preferred embodiments as described in formula (I) are also contemplated for compounds of formula (I-i), (I-ii), (I-iii), and (I-iv).

Compounds of formula (I-i) and (I-ii) are designated as cis-isomers while compounds of formula (I-iii) and (I-iv) are designated as the trans-isomers. It is thus understood that within the scope of the invention that the cis-form of compounds of formula (I) generally comprises individual isomers or mixtures of formula (I-i) and (I-ii) when at least one of m, n, p, and q is not 1. The trans-form of compounds of formula (I) generally comprises individual isomers or mixtures of formula (I-iii) and (I-iv).

All cis, trans isomeric forms and various mixtures thereof of compounds of formula (I) of the compounds described herein are intended to be encompassed within the scope of the present invention.

The term "pharmaceutically acceptable carrier", as used herein, means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; cocoa butter and suppository waxes; oils such as peanut oil, cottonseed oil, safflower oil, sesame oil, olive oil, corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate. Coloring agents, releasing agents, coating agents, sweetening, flavoring and perfuming agents, preservatives and antioxidants can also be present in the composition, according to the judgment of one skilled in the art of formulations.

The pharmaceutical compositions of this invention can be administered to humans and other mammals by oral administration, by injection, including by intravenous, subcutaneous, intramuscular, intraperitoneal, intra-arterial, and intradermal injection. The pharmaceutical compositions of this invention can be administered to humans and other mammals topically (as by powders, lotions, ointments or drops applied to the skin), bucally, or inhaled, as an oral or nasal spray. The pharmaceutical compositions of this invention can be administered to humans and other mammals intrarectally, or intravaginally. The term "parenterally," as used herein, refers to modes of administration which include intravenous, intramuscular, intraperitoneal, intrasternal, subcutaneous and intraarticular.

Pharmaceutical compositions for parenteral injection comprise pharmaceutically acceptable sterile aqueous or non-aqueous solutions, dispersions, suspensions or emulsions and sterile powders for reconstitution into sterile injectable solutions or dispersions. Examples of suitable aqueous and non-aqueous carriers, diluents, solvents or vehicles include water, ethanol, polyols (propylene glycol, polyethylene glycol, glycerol, and the like, and suitable mixtures thereof), vegetable oils (such as olive oil) and injectable organic esters such as ethyl oleate, or suitable mixtures thereof. Suitable fluidity of the composition may be maintained, for example, by the use of a coating such as lecithin, by the maintenance of the required particle size in the case of dispersions, and by the use of surfactants.

These compositions may also contain adjuvants such as preservative agents, wetting agents, emulsifying agents, and dispersing agents. Prevention of the action of microorganisms may be ensured by various antibacterial and antifungal agents, for example, parabens, chlorobutanol, phenol, sorbic acid, and the like. It may also be desirable to include isotonic agents, for example, sugars, sodium chloride and the like. Prolonged absorption of the injectable pharmaceutical form may be brought about by the use of agents that delay absorption, for example, aluminum monostearate and gelatin.

In some cases, in order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Suspensions, in addition to the active compounds, may contain suspending agents, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

If desired, and for more effective distribution, the compounds of the invention can be incorporated into slow-release or targeted-delivery systems such as polymer matrices, liposomes, and microspheres. They may be sterilized, for example, by filtration through a bacteria-retaining filter or by incorporation of sterilizing agents in the form of sterile solid compositions, which may be dissolved in sterile water or some other sterile injectable medium immediately before use.

Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations also are prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic, parenterally acceptable diluent or solvent such as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Solid dosage forms for oral administration include capsules, tablets, pills, powders, and granules. In such solid dosage forms, one or more compounds of the invention is mixed with at least one inert pharmaceutically acceptable carrier such as sodium citrate or dicalcium phosphate and/or a) fillers or extenders such as starches, lactose, sucrose, glucose, mannitol, and salicylic acid; b) binders such as carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents. Solid compositions of a similar type may also be employed as fillers in soft and hard-filled gelatin capsules using lactose or milk sugar as well as high molecular weight polyethylene glycols.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract in a delayed manner. Examples of materials which can be useful for delaying release of the active agent can include polymeric substances and waxes. Compositions for rectal or vaginal administration are preferably suppositories which can be prepared by mixing the compounds of this invention with suitable non-irritating carriers such as cocoa butter, polyethylene glycol or a suppository wax which are solid at ambient temperature but liquid at body temperature and therefore melt in the rectum or vaginal cavity and release the active compound.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents. Dosage forms for topical or transdermal administration of a compound of this invention include ointments, pastes, creams, lotions, gels, powders, solutions, sprays, inhalants or patches. A desired compound of the invention is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, lactose, talc, silicic acid, aluminum hydroxide, calcium silicates and polyamide powder, or mixtures of these substances. Sprays can additionally contain customary propellants such as chlorofluorohydrocarbons.

Compounds of the invention may also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes may be used. The present compositions in liposome form may contain, in addition to the compounds of the invention, stabilizers, preservatives, and the like. The preferred lipids are the natural and synthetic phospholipids and phosphatidylcholines (lecithins) used separately or together.

Dosage forms for topical administration of a compound of this invention include powders, sprays, ointments and inhalants. The active compound is mixed under sterile conditions with a pharmaceutically acceptable carrier and any needed preservatives, buffers or propellants, which can be required. Ophthalmic formulations, eye ointments, powders and solutions are contemplated as being within the scope of this invention. Aqueous liquid compositions comprising compounds of the invention also are contemplated.

The compounds of the invention can be used in the form of pharmaceutically acceptable salts, esters, or amides derived from inorganic or organic acids. The term "pharmaceutically acceptable salts, esters and amides", as used herein, refer to carboxylate salts, amino acid addition salts, zwitterions, esters and amides of compounds of formula (I) which are, within the scope of sound medical judgment, suitable for use in contact with the tissues of humans and lower animals without undue toxicity, irritation, allergic response, and the like, are commensurate with a reasonable benefit/risk ratio, and are effective for their intended use.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well-known in the art. The salts can be prepared in situ during the final isolation and purification of the compounds of the invention or separately by reacting a free base function with a suitable organic acid.

Representative acids suitable for formation of addition salts by combination with the compounds of the invention include, but are not limited to, ascorbic acid, (D)-tartaric acid, (L)-tartaric acid, maleic acid, phosphoric acid, citric acid, hydrochloric acid, sulfuric acid and trifluoroacetic acid. Other acids include acetic, adipic, aspartic, glutamic, benzoic, benzenesulfonic, 4-methylbenzenesulfonic, camphorsulfonic, propionic, hydrobromic, glucuronic, methanesulfonic, ethanesulfonic, naphthylenesulfonic, lactic, fumaric, oxalic, and succinic acid.

Also, the basic nitrogen-containing groups can be quaternized with such agents as lower alkyl halides such as methyl, ethyl, propyl, and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; arylalkyl halides such as benzyl and phenethyl bromides and others. Water or oil-soluble or dispersible products are thereby obtained.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium, and aluminum salts, and the like, and nontoxic quaternary ammonia and amine cations including ammonium, tetramethylammonium, tetraethylammonium, methylamine, dimethylamine, trimethylamine, triethylamine, diethylamine, ethylamine and the such as. Other representative organic amines useful for the formation of base addition salts include ethylenediamine, ethanolamine, diethanolamine, piperidine, and piperazine.

The term "pharmaceutically acceptable ester", as used herein, refers to esters of compounds of the invention which hydrolyze in vivo and include those that break down readily in the human body to leave the parent compound or a salt thereof. Examples of pharmaceutically acceptable, non-toxic esters of the invention include $C_1$-to-$C_6$ alkyl esters and $C_5$-to-$C_7$ cycloalkyl esters, although $C_1$-to-$C_4$ alkyl esters are preferred. Esters of the compounds of formula (I) may be prepared according to conventional methods. For example, such esters may be appended onto hydroxy groups by reaction of the compound that contains the hydroxy group with acid and an alkylcarboxylic acid such as acetic acid, or with acid and an arylcarboxylic acid such as benzoic acid. In the case of compounds containing carboxylic acid groups, the pharmaceutically acceptable esters are prepared from compounds containing the carboxylic acid groups by reaction of the compound with base such as triethylamine and an alkyl halide, alkyl triflate, for example with methyl iodide, benzyl iodide, cyclopentyl iodide. They also may be prepared by reaction of the compound having a carboxylic acid moiety with an acid such as hydrochloric acid and an alcohol such as methanol, or ethanol.

The term "pharmaceutically acceptable amide", as used herein, refers to non-toxic amides of the invention derived from ammonia, primary $C_1$-to-$C_6$ alkyl amines and secondary $C_1$-to-$C_6$ dialkyl amines. In the case of secondary amines, the amine may also be in the form of a 5- or 6-membered heterocycle containing one nitrogen atom. Amides derived from ammonia, $C_1$-to-$C_3$ alkyl primary amides and $C_1$-to-$C_2$ dialkyl secondary amides are preferred. Amides of the compounds of formula (I) may be prepared according to conventional methods. Pharmaceutically acceptable amides are prepared from compounds containing primary or secondary amine groups by reaction of the compound that contains the amino group with an alkyl anhydride, aryl anhydride, acyl halide, or aryl acid chloride. In the case of compounds containing carboxylic acid groups, the pharmaceutically acceptable esters are prepared from compounds containing the carboxylic acid groups by reaction of the compound with base such as triethylamine, a dehydrating agent such as dicyclohexyl carbodiimide or carbonyl diimidazole, and an alkyl amine, dialkylamine, for example with methylamine, diethylamine, piperidine. They also may be prepared by reaction of the compound with an acid such as sulfuric acid and an alkylcarboxylic acid such as acetic acid, or with acid and an arylcarboxylic acid such as benzoic acid under dehydrating conditions as with molecular sieves added. The composition can contain a compound of the invention in the form of a pharmaceutically acceptable prodrug.

The term "pharmaceutically acceptable prodrug" or "prodrug", as used herein, represents those prodrugs of the compounds of the invention which are, within the scope of sound medical judgment, suitable for use in contact with the tissues of humans and lower animals without undue toxicity, irritation, allergic response, and the like, commensurate with a reasonable benefit/risk ratio, and effective for their intended use. Prodrugs of the invention may be rapidly transformed in vivo to a parent compound of formula (I), for example, by hydrolysis in blood. A thorough discussion is provided in T. Higuchi and V. Stella, Pro-drugs as Novel Delivery Systems, V. 14 of the A.C.S. Symposium Series, and in Edward B. Roche, ed., Bioreversible Carriers in Drug Design, American Pharmaceutical Association and Pergamon Press (1987), hereby incorporated by reference.

The invention contemplates pharmaceutically active compounds either chemically synthesized or formed by in vivo biotransformation to compounds of formula (I).

Biological Data

[$^3$H]-Cytisine Binding

Binding to α4β2 nAChRs subtype was determined according to the conditions which were modified from the procedures described in Pabreza L A, Dhawan, S, Kellar K J, [$^3$H]-Cytisine Binding to Nicotinic Cholinergic Receptors in Brain, Mol. Pharm. 39: 9-12, 1991. Membrane enriched fractions from rat brain minus cerebellum (ABS Inc., Wilmington, Del.) were slowly thawed at 4° C., washed and resuspended in 30 volumes of BSS-Tris buffer (120 mM NaCl/5 mM KCl/2 mM CaCl$_2$/2 mM MgCl$_2$/50 mM Tris-Cl, pH 7.4, 4° C.). Samples containing 100-200 μg of protein and 0.75 nM [$^3$H]-cytisine (30 C$_i$/mmol; Perkin Elmer/NEN Life Science Products, Boston, Mass.) were incubated in a final volume of 500 μL for 75 minutes at 4° C. Seven log-dilution concentrations of each compound were tested in duplicate. Non-specific binding was determined in the presence of 10 μM (−)-nicotine. Bound radioactivity was isolated by vacuum filtration onto prewetted glass fiber filter plates (Millipore, Bedford, Mass.) using a 96-well filtration apparatus (Packard Instruments, Meriden, Conn.) and were then rapidly rinsed with 2 mL of ice-cold BSS buffer (120 mM NaCl/5 mM KCl/2 mM CaCl$_2$/2 mM MgCl$_2$). Packard MicroScint-20® scintillation cocktail (40 μL) was added to each well and radioactivity determined using a Packard TopCount® instrument. The IC$_{50}$ values were determined by nonlinear regression in Microsoft Excels software. K$_i$ values were calculated from the IC$_{50}$s using the Cheng-Prusoff equation, where K$_i$=IC$_{50}$(1+[Ligand]/K$_D$).

Compounds comprised in the present application have Ki values ranging from 0.01 nM to 1.0 μM ($10^{-1}$ to $10^{-6}$ M).

The invention claimed is:

1. A compound having formula (I)

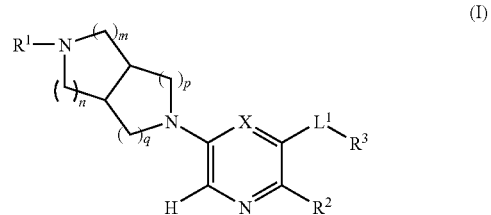

or a pharmaceutically acceptable salt, or a combination thereof, wherein

X is CH;

$R^1$ is hydrogen, alkyl, alkenyl, or heteroarylalkyl; wherein the heteroaryl moiety of the heteroarylalkyl is optionally substituted with 1, 2, 3, 4, or 5 substituents as represented by $R^x$;

m and q are each independently 1 or 2;

n and p are each independently 0, 1, or 2;

$R^2$ is hydrogen, halogen, $C_{1-3}$ haloalkyl, $C_{1-3}$ alkyl, CN, $NO_2$, C(O)H, $C_{1-3}$ alkoxy, $C_{1-3}$ haloalkoxy, or $NH_2$;

$L^1$ is a bond, —C(=Y)N($R^a$)—, —N($R^a$)C(=Y)—, N($R^b$), S, S(O), S(O)$_2$, C(=Y), —C($R^c$)=N—O—, —C($R^c$)=N—N($R^{c'}$), or —C($R^c$)=N—N($R^{c''}$)C(O)—; wherein each occurrence of Y is independently O or S;

$R^3$ is $C_{2-4}$ alkenylenyl-$G^1$, $G^2$, or —(CR$^d$R$^e$)$_t$-$G^3$; provided that when $R^3$ is $G^2$, then $L^1$ is other than a bond;

t is 1, 2, 3, or 4;

$R^d$ and $R^e$, at each occurrence, are independently hydrogen, alkyl, haloalkyl, halogen, OR$^f$, N(R$^f$)(R$^g$), —(C$_{1-6}$ alkylenyl)-OR$^f$, or —(C$_{1-6}$ alkylenyl)-N(R$^f$)(R$^g$);

$R^a$, $R^b$, $R^c$, $R^{c'}$, $R^{c''}$, $R^f$, and $R^g$, at each occurrence, are each independently hydrogen, alkyl, or haloalkyl;

$G^1$, $G^2$, and $G^3$, are each independently aryl, heteroaryl, heterocyclyl, cycloalkyl, or cycloalkenyl, wherein each ring as represented by $G^1$, $G^2$, and $G^3$, are each independently unsubstituted or substituted with 1, 2, 3, 4, or 5 substituents independently selected from the group consisting of alkyl, alkenyl, alkynyl, halogen, oxo, CN, $NO_2$, O(R$^4$), S(R$^4$), S(O)R$^5$, S(O)$_2$R$^5$, S(O)$_2$N(R$^6$)(R$^7$), OC(O)(R$^4$), C(O)R$^4$, C(O)O(R$^4$), C(O)N(R$^6$)(R$^7$), N(R$^6$)(R$^7$), N(R$^6$)S(O)$_2$(R$^5$), N(R$^6$)C(O)O(R$^4$), N(R$^6$)C(O)N(R$^6$)(R$^7$), N(R$^6$)S(O)$_2$N(R$^6$)(R$^7$), haloalkyl, —(C$_{1-6}$ alkylenyl)-CN, —(C$_{1-6}$ alkylenyl)-NO$_2$, —(C$_{1-6}$ alkylenyl)-O(R$^4$), —(C$_{1-6}$ alkylenyl)-S(R$^4$), —(C$_{1-6}$ alkylenyl)-S(O)R$^5$, —(C$_{1-6}$ alkylenyl)-S(O)$_2$R$^5$, —(C$_{1-6}$ alkylenyl)-S(O)$_2$N(R$^6$)(R$^7$), —(C$_{1-6}$ alkylenyl)-OC(O)(R$^4$), —(C$_{1-6}$ alkylenyl)-C(O)R$^4$, —(C$_{1-6}$ alkylenyl)-C(O)O(R$^4$), —(C$_{1-6}$ alkylenyl)-C(O)N(R$^6$)(R$^7$), —(C$_{1-6}$ alkylenyl)-N(R$^6$)(R$^7$), —(C$_{1-6}$ alkylenyl)-N(R$^6$)S(O)$_2$(R$^5$), —(C$_{1-6}$ alkylenyl)-N(R$^6$)C(O)O(R$^4$), —(C$_{1-6}$ alkylenyl)-N(R$^6$)C(O)N(R$^6$)(R$^7$), —(C$_{1-6}$ alkylenyl)-N(R$^6$)S(O)$_2$N(R$^6$)(R$^7$), $G^4$, or —(C$_{1-6}$ alkylenyl)-$G^4$;

$R^4$ and $R^7$, at each occurrence, are each independently hydrogen, alkyl, haloalkyl, $G^5$, or —(C$_{1-6}$ alkylenyl)-$G^5$;

$R^5$, at each occurrence, is independently alkyl, haloalkyl, $G^5$, or —(C$_{1-6}$ alkylenyl)-$G^5$;

$R^6$, at each occurrence, is independently hydrogen, alkyl, or haloalkyl;

$G^4$ and $G^5$, are each independently aryl, heteroaryl, heterocyclyl, cycloalkyl or cycloalkenyl;

each of which is independently unsubstituted or substituted by 1, 2, 3, 4, or 5 substituents as represented by $R^8$; and each occurrence of $R^8$ and $R^x$ are independently alkyl, alkenyl, alkynyl, halogen, oxo, CN, $NO_2$, O(R$^9$), S(R$^9$), S(O)R$^{10}$, S(O)$_2$R$^{10}$, S(O)$_2$N(R$^{11}$)(R$^{12}$), OC(O)(R$^9$), C(O)R$^9$, C(O)O(R$^9$), C(O)N(R$^{11}$)(R$^{12}$), N(R$^{11}$)(R$^{12}$), N(R$^{11}$)S(O)$_2$(R$^{10}$), N(R$^{11}$)C(O)O(R$^9$), N(R$^{11}$)C(O)N(R$^{11}$)(R$^{12}$), N(R$^{11}$)S(O)$_2$N(R$^{11}$)(R$^{12}$), haloalkyl, —(C$_{1-6}$ alkylenyl)-CN, —(C$_{1-6}$ alkylenyl)-NO$_2$, —(C$_{1-6}$ alkylenyl)-O(R$^9$), —(C$_{1-6}$ alkylenyl)-S(R$^9$), —(C$_{1-6}$ alkylenyl)-S(O)R$^{10}$, —(C$_{1-6}$ alkylenyl)-S(O)$_2$R$^{10}$, —(C$_{1-6}$ alkylenyl)-S(O)$_2$N(R$^{11}$)(R$^{12}$), —(C$_{1-6}$ alkylenyl)-OC(O)(R$^9$), —(C$_{1-6}$ alkylenyl)-C(O)R$^9$, —(C$_{1-6}$ alkylenyl)-C(O)O(R$^9$), —(C$_{1-6}$ alkylenyl)-C(O)N(R$^{11}$)(R$^{12}$), —(C$_{1-6}$ alkylenyl)-N(R$^{11}$)(R$^{12}$), —(C$_{1-6}$ alkylenyl)-N(R$^{11}$)S(O)$_2$)(R$^{10}$), —(C$_{1-6}$ alkylenyl)-N(R$^{11}$)C(O)O(R$^9$), —(C$_{1-6}$ alkylenyl)-N(R$^{11}$)C(O)N(R$^{11}$)(R$^{12}$), or —(C$_{1-6}$ alkylenyl)-N(R$^{11}$)S(O)$_2$N(R$^{11}$)(R$^{12}$); wherein R$^9$, R$^{11}$, and R$^{12}$, at each occurrence, are each independently hydrogen, alkyl, or haloalkyl; and R$^{10}$, at each occurrence, is independently alkyl or haloalkyl.

2. The compound of claim 1 or a pharmaceutically acceptable salt thereof wherein m and n are each independently 1;

q is 2;

p is 0;

$L^1$ is —C(=Y)N(R$^a$)—;

Y is O;

$R^a$ is hydrogen;

$R^3$ is $G^2$ or —(CR$^d$R$^e$)$_t$-$G^3$; wherein $G^2$ and $G^3$ are each independently aryl;

$R^d$ and $R^e$ are each independently hydrogen; and t is as described in claim 1.

3. The compound of claim 1 or a pharmaceutically acceptable salt thereof wherein m, n, p and q are each independently 1;

$L^1$ is —C(=Y)N(R$^a$)—;

Y is S;

$R^a$ is hydrogen; and $R^3$ is $G^2$; wherein $G^2$ is aryl.

4. The compound of claim 1 or a pharmaceutically acceptable salt thereof wherein m, n, p and q are each independently 1;

$L^1$ is —C(R$^c$)=N—O—;

$R^c$ is hydrogen or alkyl; and $R^3$ is $G^2$; wherein $G^2$ is aryl.

5. The compound of claim 1 or a pharmaceutically acceptable salt thereof wherein m, n, p and q are each independently 1;

$L^1$ is —C(R$^c$)=N—O—;

$R^c$ is hydrogen; $R^3$ is —(CR$^d$R$^e$), $G^3$ wherein $G^3$ is aryl;

$R^d$ and $R^e$ are each independently hydrogen; and t is as described in claim 1.

6. The compound according to claim 1 or a pharmaceutically acceptable salt thereof wherein m, n, p and q are each independently 1;

$L^1$ is C(=Y);

Y is O; and $R^3$ is $G^2$; wherein $G^2$ is heterocyclyl.

7. The compound of claim 1 or a pharmaceutically acceptable salt thereof wherein p and q are each independently 1;

m is 2;

n is 0;

$L^1$ is —C(=Y)N(R$^a$)—;

$R^a$ is hydrogen;

Y is O; and $R^3$ is $G^2$ wherein $G^2$ is aryl.

8. The compound of claim 1 or a pharmaceutically acceptable salt thereof wherein m, n, p and q are each independently 1.

9. The compound of claim 8 or a pharmaceutically acceptable salt thereof wherein $L^1$ is N(R$^b$);

$R^b$ is hydrogen;

$R^3$ is —(CR$^d$R$^e$)$_t$-$G^3$; wherein $G^3$ is aryl;

$R^d$ and $R^e$ are are each independently hydrogen; and t is as described in claim 1.

10. The compound of claim 8 or a pharmaceutically acceptable salt thereof wherein
   $L^1$ is a bond; and
   $R^3$ is —C, alkenylenyl-$G^1$; wherein $G^1$ is aryl.

11. The compound of claim 8 or a pharmaceutically acceptable salt thereof wherein
   $L^1$ is a bond;
   $R^3$ is —$(CR^dR^e)_t$-$G^3$; wherein $G^3$ is aryl;
   $R^d$ and $R^e$ are each independently hydrogen; and
   t is as described in claim 1.

12. The compound of claim 8 or a pharmaceutically acceptable salt thereof wherein
   $L^1$ is —C(=Y)N($R^a$)—;
   Y is O;
   $R^a$ is hydrogen or alkyl;
   $R^3$ is —$(CR^dR^e)_t$-$G^3$ wherein $G^3$ is aryl;
   $R^d$ and $R^e$, at each occurrence, are each independently hydrogen or alkyl; and
   t is as described in claim 1.

13. The compound of claim 8 or a pharmaceutically acceptable salt thereof wherein
   $L^1$ is —C(=Y)N($R^a$)—;
   Y is O;
   $R^a$ is hydrogen;
   $R^3$ is —$(CR^dR^e)$, $G^3$ or $G^2$; wherein $G^2$ and $G^3$ are each independently heteroaryl;
   $R^d$ and $R^e$ are each independently hydrogen; and
   t is as described in claim 1.

14. The compound of claim 8 or a pharmaceutically acceptable salt thereof wherein
   $L^1$ is —C(=Y)N($R^a$)—;
   Y is O;
   $R^a$ is hydrogen; and
   $R^3$ is $G^2$; wherein $G^2$ is aryl.

15. The compound according to claim 1, that is selected from the group consisting of
   N-benzyl-5-((3aR,6aS)-hexahydropyrrolo[3,4-c]pyrrol-2(1H)-yl)pyridin-3-amine;
   (3aR,6aS)-2-(5-styrylpyridin-3-yl)octahydropyrrolo[3,4-c]pyrrole;
   (3aR,6aS)-2-(5-(4-fluorostyryl)pyridin-3-yl)octahydropyrrolo[3,4-c]pyrrole;
   (3aR,6aS)-2-(5-phenethylpyridin-3-yl)octahydropyrrolo[3,4-c]pyrrole;
   (3aR,6aS)-2-(5-(4-fluorophenethyl)pyridin-3-yl)octahydropyrrolo[3,4-c]pyrrole;
   5-((3aR,6aS)-hexahydropyrrolo[3,4-c]pyrrol-2(1H)-yl)-N-(2-methylbenzyl)nicotinamide;
   5-((3aS,6aS)-hexahydropyrrolo[3,4-b]pyrrol-1(2H)-yl)-N-(2-methylbenzyl)nicotinamide;
   5-((3aR,6aS)-hexahydropyrrolo[3,4-c]pyrrol-2(1H)-yl)-N-(2-(trifluoromethyl)benzyl)nicotinamide;
   N-(2-fluorophenethyl)-5-((3aR,6aS)-hexahydropyrrolo[3,4-c]pyrrol-2(1H)-yl)nicotinamide;
   N-(3,5-dimethoxyphenyl)-5-((3aR,6aS)-hexahydropyrrolo[3,4-c]pyrrol-2(1H)-yl)nicotinamide;
   5-((3aR,6aS)-hexahydropyrrolo[3,4-c]pyrrol-2(1H)-yl)-N-(2-methoxybenzyl)nicotinamide;
   5-((3aR,6aS)-hexahydropyrrolo[3,4-c]pyrrol-2(1H)-yl)-N—((R)-1-phenylethyl)nicotinamide;
   5-((3aR,6aS)-hexahydropyrrolo[3,4-c]pyrrol-2(1H)-yl)-N—((S)-1-phenylethyl)nicotinamide;
   5-((3aR,6aS)-hexahydropyrrolo[3,4-c]pyrrol-2(1H)-yl)-N-m-tolylnicotinamide;
   N-(3,5-dimethylphenyl)-5-((3aR,6aS)-hexahydropyrrolo[3,4-c]pyrrol-2(1H)-yl)nicotinamide;
   5-((3aR,6aS)-hexahydropyrrolo[3,4-c]pyrrol-2(1H)-yl)-N-(2-(thiophen-2-yl)ethyl)nicotinamide;
   N-(3,5-difluorophenyl)-5-((3aR,6aS)-hexahydropyrrolo[3,4-c]pyrrol-2(1H)-yl)nicotinamide;
   N-(2,3-dihydro-1H-inden-1-yl)-5-((3aR,6aS)-hexahydropyrrolo[3,4-c]pyrrol-2(1H)-yl)nicotinamide;
   5-((3aR,6aS)-hexahydropyrrolo[3,4-c]pyrrol-2(1H)-yl)-N-(3-isopropoxyphenyl)nicotinamide;
   5-((3aR,6aS)-hexahydropyrrolo[3,4-c]pyrrol-2(1H)-yl)-N-(3-iodophenyl)nicotinamide;
   N-benzyl-5-((3aR,6aS)-hexahydropyrrolo[3,4-c]pyrrol-2(1H)-yl)-N-methylnicotinamide;
   N-(benzo[d]thiazol-6-yl)-5-((3aR,6aS)-hexahydropyrrolo[3,4-c]pyrrol-2(1H)-yl)nicotinamide;
   N-(3,5-bis(trifluoromethyl)phenyl)-5-((3aR,6aS)-hexahydropyrrolo[3,4-c]pyrrol-2(1H)-yl)nicotinamide;
   N-(4-chlorophenyl)-5-((3aR,6aS)-hexahydropyrrolo[3,4-c]pyrrol-2(1H)-yl)nicotinamide;
   5-((3aR,6aS)-hexahydropyrrolo[3,4-c]pyrrol-2(1H)-yl)-N-(4-phenoxyphenyl)nicotinamide;
   N-(3,4-dichlorophenethyl)-5-((3aR,6aS)-hexahydropyrrolo[3,4-c]pyrrol-2(1H)-yl)nicotinamide;
   N-(3-fluoro-5-(trifluoromethyl)benzyl)-5-((3aR,6aS)-hexahydropyrrolo[3,4-c]pyrrol-2(1H)-yl)nicotinamide;
   N-(3,5-difluorophenyl)-5-((3aR,6aR)-hexahydropyrrolo[3,4-b]pyrrol-1(2H)-yl)nicotinamide;
   N-(3,5-difluorophenyl)-5-((3aS,6aS)-hexahydropyrrolo[3,4-b]pyrrol-1(2H)-yl)nicotinamide;
   N-(3,5-difluorophenyl)-5-((3aS,6aS)-hexahydropyrrolo[3,4-b]pyrrol-5(1H)-yl)nicotinamide;
   (3,4-dihydroisoquinolin-2(1H)-yl)(5-((3aR,6aS)-hexahydropyrrolo[3,4-c]pyrrol-2(1H)-yl)pyridin-3-yl)methanone;
   N-(3,5-difluorophenyl)-5-((3aR,6aS)-5-(pyridin-3-ylmethyl)hexahydropyrrolo[3,4-c]pyrrol-2(1H)-yl)nicotinamide;
   N-(3,5-difluorophenyl)-5-((3aR,6aS)-hexahydropyrrolo[3,4-c]pyrrol-2(1H)-yl)pyridine-3-carbothioamide;
   (3aR,6aS)-5-(5-(4-Chlorophenoxyimino)methyl)pyridin-3-yl)hexahydropyrrolo[3,4-c]pyrrole;
   (3aR,6aS)-5-(5-(4-Benzyloxyimino)methyl)pyridin-3-yl)hexahydropyrrolo[3,4-c]pyrrole; and
   1-(5-((3aR,6aS)-hexahydropyrrolo[3,4-c]pyrrol-2(1H)-yl)pyridin-3-yl)ethanone O-4-chlorophenyl oxime;
   or a pharmaceutically acceptable salt thereof.

16. A pharmaceutical composition comprising a compound of claim 1 or a pharmaceutically acceptable salt thereof and one or more pharmaceutically acceptable carriers.

* * * * *